(12) United States Patent  (10) Patent No.: US 8,592,415 B2
Ma et al.                  (45) Date of Patent:   Nov. 26, 2013

(54) SELECTIVE KINASE INHIBITORS

(75) Inventors: Haiching Ma, Malvern, PA (US); Sorin Vasile Filip, Wadebridge (GB); Matthew Alexander Henry, Camelford (GB); James Alexander Dolan, Truro (GB); Bartosz Dietrich, Plymouth (GB)

(73) Assignees: Reaction Biology Corp., Woodbridge, CT (US); Synerga Limited, London (GB)

( * ) Notice: Subject to any disclaimer, the term of this patent is extended or adjusted under 35 U.S.C. 154(b) by 76 days.

(21) Appl. No.: 12/704,404

(22) Filed: Feb. 11, 2010

(65) Prior Publication Data

US 2011/0071149 A1   Mar. 24, 2011

Related U.S. Application Data

(60) Provisional application No. 61/151,660, filed on Feb. 11, 2009.

(51) Int. Cl.
| A61K 31/535 | (2006.01) |
| A01N 43/58 | (2006.01) |
| A01N 43/60 | (2006.01) |
| A61K 31/495 | (2006.01) |
| A61K 31/50 | (2006.01) |
| C07D 241/36 | (2006.01) |

(52) U.S. Cl.
USPC ........ 514/234.8; 544/353; 544/119; 514/249; 435/184

(58) Field of Classification Search
USPC ......... 514/234.8, 249; 544/353, 119; 435/184
See application file for complete search history.

(56) References Cited

U.S. PATENT DOCUMENTS

| 5,932,580 | A | 8/1999 | Levitzki et al. |
| 6,177,433 | B1 | 1/2001 | Uckun et al. |
| 6,452,005 | B1 | 9/2002 | Uckun et al. |
| 6,627,754 | B2 | 9/2003 | Blumenkopf et al. |
| 6,933,300 | B2 | 8/2005 | Uckun et al. |
| 7,084,147 | B2 | 8/2006 | Cockerill et al. |
| 7,091,208 | B2 | 8/2006 | Blumenkopf et al. |
| 7,112,594 | B2 | 9/2006 | Ushio et al. |
| 7,122,552 | B2 | 10/2006 | Ledford |
| 7,129,253 | B2 | 10/2006 | Glennon et al. |
| 7,189,734 | B2 | 3/2007 | Cockerill et al. |
| 7,192,963 | B2 | 3/2007 | Blumenkopf et al. |
| 7,244,735 | B2 | 7/2007 | Straub et al. |
| 7,262,200 | B2 | 8/2007 | Aronov et al. |
| 7,335,667 | B2 | 2/2008 | Rodgers et al. |
| 7,396,832 | B2 | 7/2008 | Lindsley et al. |
| 7,432,370 | B2 | 10/2008 | Wilcox et al. |
| 7,435,814 | B2 | 10/2008 | Singh et al. |
| 7,435,879 | B2 | 10/2008 | Streit et al. |
| 2005/0113395 | A1 | 5/2005 | Changelian |
| 2006/0183761 | A1 | 8/2006 | Ledeboer et al. |
| 2007/0004762 | A9 | 1/2007 | Ledeboer et al. |
| 2008/0009488 | A1 | 1/2008 | Anand et al. |

FOREIGN PATENT DOCUMENTS

| WO | WO 98/05335 | | 2/1998 |
| WO | WO 99/65909 | | 12/1999 |
| WO | WO 00/00202 | | 1/2000 |
| WO | WO 01/42246 | A2 | 6/2001 |
| WO | WO 02/00196 | A2 | 1/2002 |
| WO | WO 03/007959 | * | 1/2003 |
| WO | WO 2004/099205 | A1 | 11/2004 |
| WO | WO 2005/056547 | A2 | 6/2005 |
| WO | WO 2006/069080 | A2 | 6/2006 |
| WO | 2006/078283 | A2 | 7/2006 |
| WO | WO2006/078283 | A2 | 7/2006 |
| WO | WO 2007/053452 | A1 | 5/2007 |
| WO | WO 2007/089768 | A2 | 8/2007 |
| WO | WO 2008/047831 | A1 | 4/2008 |
| WO | WO2008/148867 | A2 | 12/2008 |
| WO | WO 2010/023924 | A1 | 8/2010 |

OTHER PUBLICATIONS

Abrams et al., A Clonal CD4-Positive T-Cell Line Established from the Blood of a Patient with Sézary Syndrome, *J Investig Dermatol* (Jan. 1991), 96(1):31-37.
Benekli, et al., Signal transducer and activator of transcription proteins in leukemias, *Blood* (Apr. 15, 2003), 101(8):2940-2954.
Berge, et al., Pharmaceutical Salts, *The Journal of Pharmaceutical Sciences* (Jan. 1977), 66(1):1-19.
Borie, et al., Immunosuppression by the JAK3 Inhibitor CP-690,550 Delays Rejection and Significantly Prolongs Kidney Allograft Survival in Nonhuman Primates, *Transplantation* (Apr. 15, 2005), 79(7):791-801.
Borie, et al., JAK3 inhibition, a viable new modality of immunosuppression for solid organ transplants, *Trends Mol. Med.* (Oct. 12, 2004), 10(11):532-541.

(Continued)

Primary Examiner — Sreeni Padmanabhan
Assistant Examiner — Uma Ramachandran
(74) Attorney, Agent, or Firm — Pepper Hamilton LLP

(57) ABSTRACT

The present invention relates to methods of modulating (for example, inhibiting) activity of JAK3, comprising contacting the JAK3 with a compound of Formula I:

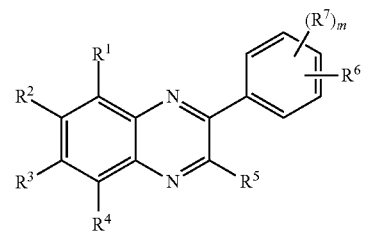

or pharmaceutically acceptable salt thereof, wherein constituent members are provided herewith. The present invention further provides novel compounds and compositions as well as their methods of preparation and use of the same as JAK3 inhibitors in the treatment of JAK3-associated diseases including, for example, inflammatory and autoimmune disorders.

15 Claims, No Drawings

(56) References Cited

OTHER PUBLICATIONS

Buckley, et al., Human severe combined immunodeficiency: Genetic, phenotypic, and functional diversity in one hundred eight infants, *J Pediatr* (Mar. 1997), 130(3):378-387.

Cetkovic-Cvrlje, et al., Targeting JAK3 with JANEX-1 for prevention of autoimmune type 1 diabetes in NOD mice, *Clinical Immunology* (2003), 106:213-225.

Cetkovic-Cvrlje, et al., Therapeutic Potential of Janus Kinase 3 (JAK3) Inhibitors, *Current Pharmaceutical Design* (2004), 10(15):1767-1784.

Changelian, et al., The specificity of JAK3 kinase inhibitors, *Blood* (Dec. 19, 2007), 111(4):2155-2157.

Changelian, et al., Prevention of Organ Allograft Rejection by a Specific Janus Kinase 3 Inhibitor, *Science* (Oct. 31, 2003), 302:875-878.

Conklyn, et al., The JAK3 inhibitor CP-690550 selectively reduces NK and CD8+ cell numbers in cynomolgus monkey blood following chronic oral dosing, *Journal of Leukocyte Biology* (Dec. 2004), 76:1248-1255.

Darnell, et al., Jak-STAT Pathways and Transcriptional Activation in Response to IFNs and Other Extracellular Signaling Proteins, *Science* (Jun. 3, 1994), 264(15640:1415-1421.

Demoulin, et al., A Single Tyrosine of the Interleukin-9 (IL-9) Receptor is Required for STAT Activation, Antiapoptotic Activity, and Growth Regulation by IL-9, *Mol. Cell. Biol.* (Sep. 1996), 16(9):4710-4716.

Deuse, et al., Novel Immunosuppression: R348, a JAK3- and Syk-Inhibitor Attenuates Acute Cardiac Allograft Rejection, *Transplantation* (Mar. 27, 2008), 85(6):885-892.

Fedorov, et al., A systematic interaction map of validated kinase inhibitors with Ser/Thr kinases, *PNAS* (Dec. 18, 2007), 104(51):20523-20528.

Ihle, et al., Jaks and Stats in signaling by the cytokine receptor superfamily, *TIG* (Feb. 1995), 11(2):69-74.

Ihle, Janus kinases in cytokine signalling, *Phil. Trans. R., Soc. Lond. B* (1996), 351:159-166.

Johnston, et al., Phosphorylation and activation of the Jak-3 Janus kinase in response to interleukin-2, *Nature* (Jul. 14, 1994), 370:151-153.

Jurlander, et al., Characterization of Interleukin-10 Receptor Expression on B-Cell Chronic Lymphocytic Leukemia Cells, *Blood* (Jun. 1, 1997), 89(11):4146-4152.

Kaneko, et al., Rescue by cytokines of apoptotic cell death induced by IL-2 deprivation of human antigen-specific T cell clones, *Clin. Exp. Immun.* (Jul. 1997) 109:185-193.

Karaman, et al., A quantitative analysis of kinase inhibitor selectivity, *Nature Biotechnology* (Jan. 8, 2008), 26(1):127-132.

Kiyoi, et al., JAK3 mutations occur in acute megakaryoblastic leukemia both in Down syndrome children and non-Down syndrome adults, *Leukemia* (Jan. 25, 2007), 21:574-576.

Leonard, STATs and cytokine specificity, *Nature Medicine* (Sep. 1996), 2(9):968-969.

Levy, The House that JAK/STAT Built, *Cytokine & Growth Factor Reviews* (1997), 8(1):81-90.

Lin, et al., Constitutive Activation of JAK3/STAT3 in Colon Carcinoma Tumors and Cell Lines, *AJP* (Oct. 2005), 167(4):969-980.

Lin, et al., Selective Itk inhibitors Block T-Cell Activation and Murine Lung Inflammation, *BioChemistry* (2004), 43:11056-11062.

Luo, et al., Inhibitors of JAKs/STATs and the kinases: a possible new cluster of drugs, *DDT* (Mar. 2004), 9(6):268-275.

Ma, et al., The challenge of selecting protein kinase assays for lead discovery optimization, *Expert Opin Drug Discov.* (Jun. 2008), 3(6):607-621.

Macchi, et al., Mutations of Jak-3 gene in patients with autosomal severe combined immune deficiency (SCID), *Nature* (Sep. 7, 1995), 377:65-68.

Malaviya, et. al., Targeting Janus Kinase 3 in Mast Cells Prevents Immediate Hypersensitivity Reactions and Anaphylaxis, *Journal of Biological Chemistry* (Sep. 17, 1999), 274(38):27028-27038.

Marzec, et al., Inhibition of ALK enzymatic activity in T-cell lymphoma cells induces apoptosis and suppresses proliferation and STAT3 phosphorylation independently of Jak3, *Laboratory Investigation* (Sep. 19, 2005) 85:1544-1554.

Milici, et al., Cartilage preservation by inhibition of Janus kinase 3 in two rodent models of rheumatoid arthritis, *Arthritis Research & Therapy* (Jan. 30, 2008), 10:R14.

Mosmann, Rapid Colorimetric Assay for Cellular Growth and Survival: Application to Proliferation and Cytotoxicity Assays, *J. Immunol. Methods* (1983), 65:55-63.

Nakamura, et al., An Epidermal Growth Factor Receptor/Jak2 Tyrosine Kinase Domain Chimera Induces Tyrosine Phosphorylation of Stat5 and Transduces a Growth Signal in Hematopoietic Cells, *J. Biol. Chem.* (Aug. 9, 1996), 271(32):19483-19488.

Nosaka, et al., Defective Lymphoid Development in Mice Lacking Jak3, *Science* (Nov. 3, 1995), 270(5237):800-802.

Notarangelo, et al., Of genes and phenotypes: the immunological and molecular spectrum of combined immune deficiency. Defects of the $\gamma_c$-JAK3 signaling pathway as a model, *Immunological Reviews* (2000), 178:39-48.

Olive, Quantitative methods for the analysis of protein phosphorylation in drug development, *Expert Rev. Proteomics* (2004), 1(3):327-341.

O'Shea, et al., New strategies for immunosuppression: interfering with cytokines by targeting the Jak/Stat pathway, *Current Opinion in Rheumatology* (2005), 17:305-311.

O'Shea, et al., Cytokine Signaling Modules in Inflammatory Responses, *Immunity* (Apr. 2008), 28:477-487.

O'Shea, et al., Cytokines and Autoimmunity, *Nature Reviews* (Jan. 2002), 2:37-45.

Papageorgiou, et al., Is JAK3 a new drug target for immunomodulation-based therapies?, *TRENDS in Pharmacological Sciences* (Sep. 24, 2004), 25(11): 558-562.

Pesu, et al., Therapeutic targeting of Janus kinases, *Immunol Rev.* (Jun. 2008), 223:132-142.

Ravin, Preformulation, Remington's Pharmaceutical Science, 17th ed., Mack Publishing Company, Easton, PA (1985), 1409-1423.

Readinger, et al., Selective targeting of ITK blocks multiple steps of HIV replication, *PNAS* (May 6, 2008), 105(18):6684-6689.

Säemann, et al., Prevention of CD40-Triggered Dendritic Cell Maturation and Induction of T-Cell Hyporeactivity by Targeting of Janus Kinase 3, *Am J Transplant* (2003), 3:1341-1349.

Scott, et al., Jaks, STATs, Cytokines and Sepsis, *Clin. Diagn. Lab. Immunol.* (Nov. 2002), 9(6):1153-1159.

Sills, et al., In Vitro and In Vivo Characterization of a Novel JAK3 Tyrosine Kinase Inhibitor, Inflammation Research Association Fourteenth International Conference (Oct. 15-19, 2006), Hyatt Regency Chesapeake Bay, Cambridge, Maryland, Poster A155.

Steinman, et al., Immune Therapy for Autoimmune Diseases, *Science* (Jul. 9, 2004), 305:212-216.

Suzuki, et al., Janus kinase 3 (Jak3) is essential for common cytokine receptor γ chain ($\gamma_c$)-dependent signaling: comparative analysis of $\gamma_c$, Jak3 and $\gamma_c$ and Jak3 double-deficient mice, *International Immunology* (2000), 12(2):123-132.

Thomis, et al., The role of Jak3 in lymphoid development, activation, and signaling, *Current Opinion in Immunology* (1997), 9:541-547.

Thomis, et al., Defects in B Lymphocyte Maturation and T Lymphocyte Activation in Mice Lacking Jak3, *Science* (Nov. 3, 1995), 270:794-797.

Tibbles, Role of a JAK3-dependent Biochemical Signaling Pathway in Platelet Activation and Aggregation, *J. Biol. Chem.* (May 25, 2001), 276(21):17815-17822.

Trieu, et al., A Specific Inhibitor of Janus Kinase-3 Increases Survival in a Transgenic Mouse Model of Amyotrophic Lateral Sclerosis, *Biochemical and Biophysical Research Communications* (2000), 267(1):22-25.

Verbsky, et al., Expression of Janus Kinase 3 in Human Endothelial and Other Non-lymphoid and Non-myeloid Cells, *J. Biol. Chem.* (Jun. 14, 1996), 271(24):13976-13980.

Walters, et al., Activating alleles of JAK3 in acute megakaryoblastic leukemia, *Cancer Cell* (Jul. 2006), 10:65-75.

(56) References Cited

OTHER PUBLICATIONS

Wuts, et al., *The Role of Protective Groups in Organic Synthesis*, in Greene's Protective Groups in Organic Synthesis, John Wiley & Sons, Inc., 4th Ed. (2007), pp. 1-15.

Zhong, et al., Stat3 and Stat4: Members of the family of signal transducers and activators of transcription, *Proc. Natl. Acad. Sci. USA* (May 1994), 91:4806-4810.

Supplementary European Search Report dated Jun. 6, 2012 for EP 10741733.

Wang et al., "Synthesis and Evaluation of Benzothiazole-Based Analogues as Novel, Potent, and Selective Fatty Acid Amide Hydrolase Inhibitors", *J. of Med. Chem.*, (Jan. 8, 2009), 52(1):170-180.

Database Abstract, Compound with Registry No. 692732-77-7, Retrieved from online database Jun. 14, 2004, XP-002677239.

Database Abstract, Compound with Registry No. 697238-78-1, Retrieved from online database Jun. 22, 2004, XP002677240.

Database Abstract, Compound with Registry No. 832679-46-6, Retrieved from online database Feb. 17, 2005, XP002677241.

Database Abstract, Compound with Registry No. 866131-45-5, Retrieved from online database Oct. 26, 2005, XP002677242.

* cited by examiner

SELECTIVE KINASE INHIBITORS

RELATED APPLICATIONS

This application claims benefit of priority to U.S. Provisional Patent Application Ser. No. 61/151,660 filed on Feb. 11, 2009, which is hereby incorporated by reference.

FIELD OF THE INVENTION

In some embodiments, the present invention relates to methods of modulating (for example inhibiting) activity of Janus Kinase-3 (JAK3) and/or treating JAK3-associated diseases including, for example, inflammatory disorders and autoimmune disorders. In some embodiments, the present invention also relates to novel compounds and compositions thereof, methods of preparation of the same, as well as methods of use the same for inhibition of JAK3 and/or treatment of JAK3-associated diseases.

BACKGROUND OF THE INVENTION

Cytokines are the key regulators of immunity and inflammation. Antagonism of cytokine function has emerged as an effective strategy for immunosuppression (Steinman L. Science 305:212-216 (2004)). Cytokines that bind type-1 receptors (such as interleukin-2, 3, 4, 5, 6, 7, and 9) and type-II receptors (such as INFα/β, IFNγ, IL-10, 19, and 20) are important in immunoregulation and inflammation, and critical for lymphoid development, homeostasis, and differentiation (O'Shea J J et al, Nat. Rev. Immunol. 2: 37-45 (2002); O'Shea J J et al, Curr Opin Rheumatol. 17:305-11 (2005); O'Shea J J et al Immunity. 28, 477-487 (2008)).

Signal transducers and activators of transcription (STAT) are pleiotropic transcription factors which mediate cytokine-stimulated gene expression in multiple cell populations (Levy D A, Cytokine Growth Factor Rev., 8:81 (1997)). All STAT proteins contain a DNA binding domain, a Src homology 2 (SH2) domain, and a transactivation domain necessary for transcriptional activation of target gene expression.

Janus kinases (JAK), including JAK1 (also known as Janus kinase-1), JAK2 (also known as Janus kinase-2), JAK3 (also known as Janus kinase, leukocyte; JAKL; L-JAK; and Janus kinase-3), and TYK2 (also known as protein-tyrosine kinase 2), are cytoplasmic protein tyrosine kinases (PTKs) which play pivotal roles in initiation of cytokine-triggered signaling events by activating the cytoplasmic latent forms of STAT proteins via tyrosine phosphorylation on a specific tyrosine residue near the SH2 domain (Ihle J N et al., Trends Genet., 11: 69 (1995); Darnell J E et al., Science, 265: 1415 (1994); Johnston J A et al., Nature, 370: 1513 (1994)).

Binding of the cytokines to the receptor brings JAKs together, resulting in JAK activation and autophosphorylation, with subsequent phosphorylation of tyrosine residues on the cytoplasmic portion of the receptor. The inactive STAT monomers are then recruited to the activated receptor complex via the interaction of the SH2 domains with phosphotyrosine docking sites. STATs are phosphorylated by the JAKs on a conserved tyrosine residue in the c-terminal domain to form STAT homodimers or heterodimers. STATs then dissociate from the receptor, dimerize, and translocate into the nucleus. In the nucleus, STATs bind to specific response elements and induce gene transcription (Benekli M, et al, 101, 2940-2954 (2003); Leonard W J, Nature Medicine, 2: 968 (1996); Leonard W J, Nature Medicine, 2: 968 (1996); Zhong Z et al., PNAS USA, 91:4806 (1994); Darnell Jr. J E et al., Science, 264:1415-1421 (1994); and Scott, M J et al, Clin Diagn Lab Immunol 9: 1153-1159 (2002)). The STATs control fundamental cellular processes, including survival, proliferation, and differentiation.

Different ligands employ specific JAK and STAT family members, thus utilization of this pathway mandates specificity in signaling cascades and contributes to a diverse array of cellular responses. Janus kinases, including JAK3, are abundantly expressed in primary leukemic cells from children with acute lymphoblastic leukemia (ALL), the most common form of childhood cancer, and recent studies have correlated STAT activation in ALL cells with signals regulating apoptosis (Demoulin J B, et al., Mol. Cell. Biol. 16: 4710-4716 (1996); Jurlander J., et al., Blood. 89: 4146-4152, (1997); Kaneko S, et al., Clin. Exp. Immun. 109: 185-193 (1997); and Nakamura N et al., J. Biol. Chem. 271: 19483-19488 (1996)). JAK3 mutations with continue activities are also found to express in acute megakaryoblastic leukemia (AMKL) patients, which implies the JAK3 mutants as potential therapeutic targets (Walters D K et al Cancer Cell, 10, 65-75 (2006); Kiyoi H et al Leukemia, 21, 574-576 (2007)).

Among the four members of the JAK family, JAK1, JAK2, and TYK2 are ubiquitously expressed. JAK3 is predominantly expressed in hematopoietic cells, such as Natural Killer cells and thymocytes, platelets, mast cells, and inducible T and B cells. JAK3 plays an important role in normal lymphocyte development and functions, as evidenced by qualitative and quantitative deficiencies in the B-cell as well as T-cell compartments of the immune system of JAK3-deficient mice (T. Nosaka et al., Science, 270:800 (1995): D. C. Thomas et al., Science, 270:794 (1995)); development of severe combined immunodeficiency in JAK3-deficient patients and development of severe combined immunodeficiency in JAK3-deficient patients (Buckley R H et al., J Pediatr., 130: 379 (1997)). JAK3 binds exclusively to the IL-2 cytokine receptor gamma chain and is activated by IL-2, IL-4, IL-7, IL-9, and IL-15. JAK3 is critical for lymphocyte survival, differentiation, and function. In humans, mutations in JAK3 have been associated with severe combined immunodeficiency (SCID) (Macchi P et al, Nature. 377: 65-68 (1995), Notarangelo L D Immunol Rev 178:39-48 (2000)), a disorder that is fatal in infancy unless treated by therapies such as hematopoetic stem cell transplantation. JAK3 knockout mice are found to display defects in T, B, and NK cell development and function (Nosaka T et al., Science, 270:800-802 (1995): Thomas D C et al., Science, 270:794-797 (1995); Suzuki K N et al Int Immunol 12:123-132 (2000)).

JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. An inhibitor of JAK3 will block the JAK3/STAT signaling pathway, and could be useful for treating or preventing diseases mentioned hereinabove (Cetkovic-Cvrlje et al Current Pharmaceutical Design, 10, 1767-1784 (2004); Luo C et al, 2004, Drug Discovery Today, 268-275 (2004); Pesu M et al Immunol. Rev. 223:132-42 (2008)).

Besides hematopoietic cells, JAK3 is also found to express in variety levels in endothelial cells and smooth muscle cells (Verbsky J et al, J. Biol. Chem. 271, 13976-13980 (1996)), cancers cells other than leukemia and lymphoma as described hereinabove. For example, JAK3 is constitutively phosphorylated and activated in colon carcinoma cells (Lin Q eta al Am. J. Pathol. 167, 969-980 (2005)). Information regarding the physiologic functions of JAK3 in these non-lymphoid cell populations also spurred much interest in research (Thomas D C et al., Curr. Opin. Immunol., 9: 541 (1997); Ihle J N, Philos. Trans. R. Soc. Lond B Biol. Sci., 351: 159-166 (1996); Verbsky J W et al. J. Biol. Chem., 271: 13976 (1996)).

Animal studies have suggested that JAK3 not only play a critical role in B- and T-lymphocyte maturation, but that JAK3 is constitutively required to maintain T-cell function. Modulation of immune activity through this novel mechanism can prove useful in the treatment of T-cell proliferative disorders such as transplant rejection (e.g. organ transplant rejection) (Borie D C et al, Trends Mol. Med. 10, 532-541 (2004); Borie D C et al, transplantation, 79, 791-801 (2005)) and autoimmune diseases (e.g. insulin-dependent diabetes) (Cetkovic-Cvrlje M. et al, Clinical immunology, 106, 213-225 (2003).

The role of JAK3 in mast cells has been described in knockout mice. Thus, IgE/antigen induced degranulation and mediator release were substantially reduced in mast cells generated from JAK3 deficient mice. JAK3 deficiency does not affect mast cell proliferation in vitro, and it has also been shown that IgE receptor levels and mediator contents are identical in JAK3−/− and JAK3+/+ mast cells. Therefore, JAK3 appears essential for the complete response of IgE challenged mast cells. The role of JAK3 in mast cell activation has been well established in murine system, and it was suggested that mast cells plays an important role in Autosomal Recessive-Severe Combined Immunodeficiency (AR-SCID) patients and that targeting JAK3 provides the basis for new and effective treatment of mast cell mediated allergic reactions. See e.g. WO/2004/099205. JAK3 inhibitors can be used to treat (including prevent) mast cell mediated immediate hypersensitivity reactions. See R. Malaviya, et. al, "Targeting Janus kinase 3 in mast cells prevents immediate hypersensitivity reactions and anaphylaxis"; Journal of Biological Chemistry, Vol. 274, No. 38, Issue of September 17, pp. 27028-27038, 1999.

The JAK3/STAT pathways play pivotal roles in diseases such as autoimmune diseases (e.g. rheumatoid arthritis (RA), psoriasis, multiple sclerosis, type I diabetes and complication from diabetes, lupus, autoimmune thyroid disorder, ulcerative colitis, Crohn's disease), cancer, leukemia, lymphoma, inflammatory diseases or disorders (e.g. asthma, rhinitis, and atopic dermatitis), Alzheimer's disease, and organ transplant rejection. See e.g. WO 2001042246. Pharmacological targeting of JAK3 has been employed successfully to control (treat and/or prevent) transplant complications (e.g. rejection of donor organs by the host immune system such as allograft rejection) and complications associated with bone marrow transplantation such as development of graft versus host disease (GVHD). In addition to its involvement in signaling of cytokine receptors, JAK3 is also engaged in the CD40 signaling pathway of peripheral blood monocytes. During CD40-induced maturation of myeloid dendritic cells (DCs), JAK3 activity is induced, and increases in costimulatory molecule expression, IL-12 production, and potent allogeneic stimulatory capacity are observed. A rationally designed JAK3 inhibitor WHI-P-154 prevented these effects arresting the DCs at an immature level, suggesting that immunosuppressive therapies targeting the tyrosine kinase JAK3 may also affect the function of myeloid cells (Saemann M D et al, Am J Transplant 3: 1341-1349 (2003)). In the mouse model system, JAK3 was also shown to be an important molecular target for treatment of autoimmune insulin-dependent (type 1) diabetes mellitus. The rationally designed JAK3 inhibitor JANEX-1 exhibited potent immunomodulatory activity and delayed the onset of diabetes in the NOD mouse model of autoimmune type I diabetes (Cetkovic-Cvrlje M et al, Clin Immunol 106: 213-25 (2003)). Moreover, JAK3 can be one of the regulators of platelet function, and JAK3 inhibitors can prevent platelet aggregation, inhibit thrombus formation, and thus can be anti-thrombotic agents. See e.g. Tibbles, H. E. "Role of a JAK3-dependent Biochemical Signaling Pathway in Platelet Activation and Aggregation" J. Biol. Chem., Vol. 276, Issue 21, 17815-17822, May 25, 2001; See also Cetkovic-Cvrlje, M. "Therapeutic Potential of Janus Kinase 3 (JAK3) Inhibitors" Current Pharmaceutical Design, Volume 10, Number 15, June 2004, pp. 1767-1784(18). Because of the importance of JAK3 inhibitors and the market for specific immunosuppressants, many pharmaceutical companies have established JAK3 drug development programs, including Pfizer, Vertex, Rigel, InCyte, and Pharmacopeia (Pesu et al. Immunological Reviews. 223, 132-142 (2008)). Pfizer has progressed CP-690550 (Changelian P S et al, Science, 302, 875-878 (2003)) into 19 clinical studies on ulcerative colitis; acute rejection in kidney transplantation; rheumatoid arthritis (RA); dry eye syndromes; Crohn's disease; and psoriasis. These clinical studies include Phase II clinical trials for RA and an expanded Phase I acute kidney transplant rejection trial. CP-690550 has therapeutic effects with both adjuvant-induced arthritis (AIA) and collagen-induced arthritis (CIA) rat models (Milici et al. Arthritis Research & Therapy 10:R14 (2008)). A new analog of CP-690550, PF-956980, was found to have improved JAK3 specificity (Changelian et al, Blood 111:2155-2157 (2008); WO 2001042246; U.S. Pat. No. 6,627,754; and U.S. Pat. No. 7,432,370).

Pharmacopeia (Ligand Pharmaceuticals Inc) developed a JAK3 inhibitor, PS020613, for RA, psoriasis, and other immunological conditions. PS020613 has an IC50 value of 3.4 nM for Jak3 kinase. It inhibits IL2-induced cell proliferation in mouse F7 cells with an IC50 value of 64 nM, and demonstrates 31-fold cell selectivity over Jak2. When administered orally to BALB/c mice, PS020613 inhibits $IL^2$-induced IFNg production with an ED50 value of 3 mg/kg, is efficacious in an oxazolone-induced model of delayed hypersensitivity and demonstrates good oral bioavailability (116%) (Sills M et al, Fourteenth international conference, Poster A 155 (2006)).

Rigel Pharmaceuticals Inc. is testing the compound R348 (an inhibitor for Jak3 and Syk) for Psoriasis/RA and transplant rejection (Deuse T et al, Transplantation, 85,885-892 (2008); U.S. Pat. No. 7,435,814; and U.S. Pat. No. 7,435,879).

Vertex Pharmaceuticals Inc. is testing compound VX-509 (a JAK3 inhibitor) in Phase 1a clinical development for the potential treatment of multiple immune-mediated inflammatory diseases. See e.g. U.S. Pat. No. 7,122,552.

Parker-Hughes Institute had developed a group of compounds, such as WHI-P131 and WPI-P154, as potent inhibitors for PDGFR and EGFR, and also capable to inhibit JAK3 with IC50s in low μM ranges. These compounds have been studied for their immunosuppression (Marzec M et al, Lab Invest 85: 1544-1554 (2005); Papageorgiou A C et al. Trends Pharmacol Sci. 25: 558-562 (2004); Changelian P S et al, Blood 111(4):2155-2157 (2008)). It was also reported that WHI-P131, as a JAK3 inhibitor, increased survival in a transgenic mouse model of amyotrophic lateral sclerosis (ALS) and can be useful for treatment of ALS such as FALS (Trieu V N, et. al, Biochem Biophys Res Commu., 267, 22-25 (2000)).

A JAK3-selective inhibitor (selective over other Kinases such as JAK1, JAK2, and TYK2) would not interfere with (or interfere insignificantly with) the signaling pathways mediated/controlled by other members of Kinases such as JAK1, JAK2, and TYK2. However, one draw back of some of the current JAK3 inhibitors is that they also have activities toward other kinases such as JAK1 and JAK2, which also play critical roles to the signaling of many hematopoietic cytokine and growth factor receptors. For example, a binding assay performed by Ambit has revealed that CP-690550 had very similar Ki for JAK3 (Kd=2.5 nM) and JAK2 (Kd=5 nM) (Karaman M W et al, Nat. Biotech. 26, 127-132 (2008)), although one Pfizer's publication (Changelian P S et al, *Science,* 302, 875-878 (2003)) indicated that with ELISA assays, CP-690550 inhibited JAK3 with an IC50 value of 1.5 nM, which is 20 fold more selective than toward JAK2. However low selectivity (about 2.5 fold more selective to JAK3 over JAK1) of CP-690550 was also reported according to Pharmacopeia's internal test (2nd Protein Kinases in Drug Discovery Conference, 2007). JAK3-selective inhibitors, such as compounds in the present invention, are useful in treating (and/or preventing) rheumatoid arthritis (RA), psoriasis, organ transplant rejection, allergic or type I hypersensitivity reaction such as urticaria and eczema, conjunctivitis, rhinorrhea, rhinitis, asthma and gastroenteritis, familial amyotrophic lateral sclerosis (FALS), lupus, multiple sclerosis, dry eye disease, Type I diabetes and complications from diabetes, cancer, asthma, rhinitis, atopic dermatitis, autoimmune thyroid disorders, ulcerative colitis, Crohn's disease, Alzheimer's disease, leukemia, thrombus, and other autoimmune disease.

New or improved agents which specifically inhibit JAK3 are continually needed for developing new and more effective pharmaceuticals to treat, autoimmune diseases and inflammatory diseases, to name a few. The compounds, compositions and methods described herein are directed toward these needs and other ends.

SUMMARY OF THE INVENTION

The present invention provides, inter alia, methods of modulating an activity of JAK3, comprising contacting the JAK3 with a compound of Formula I:

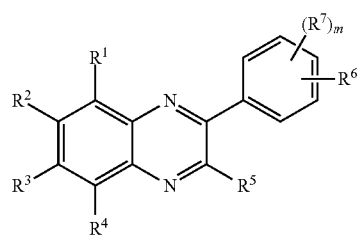

or pharmaceutically acceptable salt of the same, wherein constituent members are provided below.

In some embodiments, the present invention further provides methods of inhibiting an activity of JAK3, comprising contacting the kinases with a compound of Formula I, or pharmaceutically acceptable salt of the same.

In some embodiments, the present invention further provides methods of treating one or more of the various JAK3-associated conditions, diseases and disorders named herein by administering to a patient a therapeutically effective amount of a compound of Formula I, or pharmaceutically acceptable salt of the same.

In some embodiments, the present invention further provides compounds of Formula I, or pharmaceutically acceptable salts thereof, for use in therapy.

In some embodiments, the present invention further provides use of the compounds of Formula I, or pharmaceutically acceptable salts thereof, for the manufacture/preparation of a medicament for use in therapy.

In some embodiments, the present invention further provides novel compounds and novel pharmaceutical compositions comprising the same and at least one pharmaceutically acceptable carrier.

In some embodiments, the present invention further provides methods of use and preparation of the novel compounds and pharmaceutical compositions provided herein.

DETAILED DESCRIPTION

The present invention provides, inter alia, methods of modulating an activity of JAK3, comprising contacting the JAK3 with a compound of Formula I:

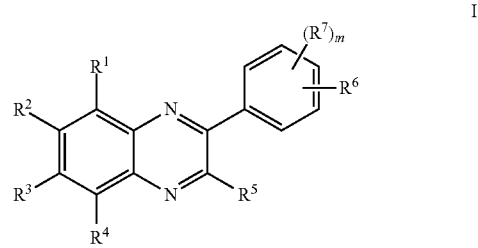

or pharmaceutically acceptable salt thereof, wherein:

$R^1$, $R^2$, $R^3$, and $R^4$ are each, independently, selected from H, halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$;

$R^5$ is selected from H, halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$;

$R^6$ is $-NR^8-W^1-(CR^9R^{10})_nR^{11}$;

each $R^7$ is independently selected from halo, CN, $NO_2$, $-NR^8-W^1-(CR^9R^{10})_nR^{11}$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$;

each $R^8$ is independently selected from H, $C_{1-4}$ alkyl, and $C_{1-4}$ haloalkyl; $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl, wherein each of the $C_{1-4}$ alkyl, $C_{1-4}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $S(O)_2R^b$, and $S(O)_2NR^cR^d$;

$R^9$ and $R^{10}$ are each, independently, selected from H, $C_{1-4}$ alkyl, and $C_{1-4}$ haloalkyl;

each $R^{11}$ is independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl, halo, CN, $NO_2$, $OR^{a11}$, $NR^{c11}R^{d11}$, $NR^{c11}C(O)R^{d11}$, $NR^{c11}C(O)OR^{a11}$, $NC(O)NR^{c11}R^{d11}$, $NR^{c11}S(O)R^{b11}$, $S(O)_2R^{b11}$, $NR^{c11}S(O)NR^{c11}R^{d11}$, and $NR^{c11}S(O)_2NR^{c11}R^{d11}$, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R_b$, $S(O)_2NR^cR^d$, $SC(O)R^b$, $-S(O)-C_{1-6}$ alkyl, $-S-C_{1-6}$ alkyl, and $-O-S(O)_2-C_{1-6}$ alkyl;

$R^{12}$ and $R^{13}$ are each, independently, selected from H, $C_{1-4}$ alkyl, and $C_{1-4}$ haloalkyl;

$R^{14}$ and $R^{15}$ are each, independently, selected from H, $C_{1-4}$ alkyl, and $C_{1-4}$ haloalkyl;

each W1 is independently selected from $-C(R12)(R13)-$, $-C(R12)=C(R16)-$, $-C(O)-$, $-S(O)-$, $-S(O)_2-$, and $-C(S)-$;

each $R^{a11}$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl is optionally substituted with 1, 2, 3, 4, or 5 substituents each independently selected from OH, CN, amino, halo, $C_{1-6}$ alkyl, $C_{1-6}$ haloalkyl, $C_{1-6}$ alkoxy, $C_{1-6}$ haloalkyl, aryl, arylalkyl, heteroaryl, heteroarylalkyl, cycloalkyl and heterocycloalkyl;

each $R^{b11}$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents each independently selected from OH, CN, amino, halo, $C_{1-6}$ alkyl, $C_{1-6}$ haloalkyl, $C_{1-6}$ alkoxy, $C_{1-6}$ haloalkyl, aryl, arylalkyl, heteroaryl, heteroarylalkyl, cycloalkyl and heterocycloalkyl;

$R^{c11}$ and $R^{d11}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, and heterocycloalkyl is optionally substituted with 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $-Y^1-Z^1$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$;

or $R^{c11}$ and $R^{d11}$ together with the N atom to which they are attached form a 4-, 5-, 6- or 7-membered heterocycloalkyl group or heteroaryl group, each optionally substituted with 1, 2, 3, 4, or 5 substituents each independently selected from halo, CN, $NO_2$, $C_{1-6}$ alkyl, $C_{2-6}$ alkenyl, $C_{2-6}$ alkynyl, $C_{1-6}$ haloalkyl, $-Y^1-Z^1$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$;

each $Y^1$ is independently selected from absent, $C_{1-6}$ alkylenyl, $C_{2-6}$ alkenylenyl, $C_{2-6}$ alkynylenyl, $-(CR^{14}R^{15})_{p1}-O-(CR^{14}R^{15})_{p2}-$, $-(CR^{14}R^{15})_{p1}-S-(CR^{14}R^{15})_{p2}-$, $-(CR^{14}R^{15})_{p1}-NR^e-(CR^{14}R^{15})_{p2}-$, $-(CR^{14}R^{15})_{p1}-C(O)-(CR^{14}R^{15})_{p2}-$, $-(CR^{14}R^{15})_{p1}-C(O)O-(CR^{14}R^{15})_{p2}-$, $-(CR^{14}R^{15})_{p1}-C(O)NR^e-(CR^{14}R^{15})_{p2}-$, $-(CR^{14}R^{15})_{p1}-$, $-S(O)_2(CR^{14}R^{15})_{p2}-$, $-(CR^{14}R^{15})_{p1}-S(O)NR^e-(CR^{14}R^{15})_{p2}-$, $-(CR^{14}R^{15})_{p1}-S(O)_2NR^e-(CR^{14}R^{15})_{p2}-$, and $-(CR^{14}R^{15})_{p1}-NR^eC(O)NR^f-(CR^{14}R^{15})_{p2}-$, wherein each of the $C_{1-6}$ alkylenyl, $C_{2-6}$ alkenylenyl and $C_{2-6}$ alkynylenyl is optionally substituted by 1, 2, or 3 substituents independently selected from halo, OH, CN, amino, $C_{1-6}$ alkylamino, $C_{2-8}$ dialkylamino, $C_{1-6}$ alkyl, $C_{1-6}$ haloalkyl, $C_{1-6}$ alkoxy, $C_{1-6}$ haloalkyl, aryl, arylalkyl, heteroaryl, heteroarylalkyl, cycloalkyl and heterocycloalkyl;

each $Z^1$ is independently selected from $C_{1-6}$ alkyl, $C_{1-6}$ haloalkyl, $C_{2-6}$ alkenyl, $C_{2-6}$ alkynyl, arylalkyl, cycloalkylalkyl, heteroarylalkyl, heterocycloalkylalkyl, aryl, cycloalkyl, heteroaryl, and heterocycloalkyl, each optionally substituted by 1, 2, 3, 4, or 5 substituents independently selected from $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$;

each $R^8$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents each independently selected from OH, CN, amino, $C_{1-6}$ alkylamino, $C_{2-8}$ dialkylamino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

each $R^b$ is independently selected from H, $NH_2$, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents each independently selected from OH, $C_{1-6}$ alkoxy, $C_{1-6}$ haloalkoxy, amino, $C_{1-6}$ alkylamino, $C_{2-8}$ dialkylamino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^c$ and $R^d$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents each independently selected from OH, $C_{1-6}$ alkoxy, $C_{1-6}$ haloalkoxy, amino, $C_{1-6}$ alkylamino, $C_{2-8}$ dialkylamino, halo, $C_{1-6}$ alkyl, $C_{1-6}$ haloalkyl, aryl, arylalkyl, heteroaryl, heteroarylalkyl, cycloalkyl and heterocycloalkyl;

or $R^c$ and $R^d$ together with the N atom to which they are attached form a 4-, 5-, 6- or 7-membered heterocycloalkyl group that is optionally substituted with 1, 2, 3, 4, or 5 substituents each independently selected from OH, $C_{1-6}$ alkoxy, $C_{1-6}$ haloalkoxy, amino, $C_{1-6}$ alkylamino, $C_{2-8}$ dialkylamino, halo, $C_{1-6}$ alkyl, $C_{1-6}$ haloalkyl, aryl, arylalkyl, heteroaryl, heteroarylalkyl, cycloalkyl or heterocycloalkyl;

$R^e$ and $R^f$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, and heterocycloalkyl is optionally substituted with 1, 2, 3, 4, or 5 substituents each independently selected from OH, $C_{1-6}$ alkoxy, $C_{1-6}$ haloalkoxy, amino, $C_{1-6}$ alkylamino, $C_{2-8}$ dialkylamino, halo, $C_{1-6}$ alkyl, $C_{1-6}$ haloalkyl, aryl, arylalkyl, heteroaryl, heteroarylalkyl, cycloalkyl, and heterocycloalkyl;

m is 0, 1, 2, 3, or 4;

each n is independently 0, 1, 2, 3, or 4;

each p1 is independently 0, 1, 2, or 3; and each p2 is independently 0, 1, 2, or 3.

In some embodiments, $R^1$, $R^2$, $R^3$, and $R^4$ are each, independently, selected from H, halo, $C_{1-6}$ alkyl, $C_{1-6}$ haloalkyl, CN, $NO_2$, OH, $C_{1-6}$ alkoxy, $C_{1-6}$ haloalkoxy, amino, $C_{1-6}$ alkylamino, and $C_{2-8}$ dialkylamino.

In some embodiments, $R^1$, $R^2$, $R^3$, and $R^4$ are each, independently, selected from H, halo, $C_{1-6}$ alkyl, $C_{1-6}$ haloalkyl, CN, $NO_2$, OH, $C_{1-6}$ alkoxy, and $C_{1-6}$ haloalkoxy.

In some embodiments, $R^1$, $R^2$, $R^3$, and $R^4$ are each, independently, selected from H, halo, $C_{1-6}$ alkyl, and $C_{1-6}$ haloalkyl.

In some embodiments, $R^1$, $R^2$, $R^3$, and $R^4$ are each, independently, selected from H and $C_{1-6}$ alkyl. In some further embodiments, $R^1$, $R^2$, $R^3$, and $R^4$ are each, independently, selected from H and $C_{1-4}$ alkyl. In yet further embodiments, $R^1$, $R^2$, $R^3$, and $R^4$ are each, independently, selected from H and methyl. In still further embodiments, $R^1$, $R^2$, $R^3$, and $R^4$ are each, H.

In some embodiments, $R^5$ is selected from H, halo, $C_{1-6}$ alkyl, $C_{1-6}$ haloalkyl, CN, $NO_2$, $C_{1-6}$ alkoxy, and $C_{1-6}$ haloalkoxy.

In some embodiments, $R^5$ is selected from H, halo, $C_{1-6}$ alkyl, and $C_{1-6}$ haloalkyl. In some further embodiments, $R^5$ is selected from H and $C_{1-6}$ alkyl. In yet further embodiments, $R^5$ is selected from H and $C_{1-4}$ alkyl. In still further embodiments, $R^5$ is selected from H and methyl. In further embodiments, $R^5$ is H.

In some embodiments, each $W^1$ is independently selected from —C($R^{12}$)($R^{13}$)—, —C(O)—, —S(O)—, —S(O)$_2$—, and —C(S)—.

In some embodiments, each $W^1$ is independently selected from —C(O)—, —S(O)—, —S(O)$_2$—, and —C(S)—. In some further embodiments, each $W^1$ is independently selected from —C(O)—, —S(O)$_2$— and —C(S)—.

In some embodiments, each $W^1$ is independently selected from —C(O)—, —S(O)$_2$—, and —C(S)—.

In some embodiments, each $W^1$ is —S(O)$_2$—.

In some embodiments, each $W^1$ is independently selected from —C($R^{12}$)($R^{13}$)—, —C(O)—, and —C(S)—; and $R^{12}$ and $R^{13}$ are each, independently, selected from H, and $C_{1-4}$ alkyl. In some further embodiments, $R^{12}$ and $R^{13}$ are each, independently, selected from H, and methyl. In yet further embodiments, $R^{12}$ and $R^{13}$ are both H.

In some embodiments, each $W^1$ is independently selected from —C(O)— and —C(S)—.

In some further embodiments, each $W^1$ is —C(O)—.

In some embodiments, each $W^1$ is —C(S)—.

In some embodiments, $R^{16}$ and —($CR^9R^{10}$)$_n R^{11}$ together with the C atom to which they are attached form a 4-, 5-, 6- or 7-membered heterocycloalkyl group that is optionally substituted with 1, 2, 3, 4, or 5 substituents each independently selected from OH, $C_{1-6}$ alkoxy, oxo (i.e. =O), $C_{1-6}$ haloalkoxy, amino, $C_{1-6}$ alkylamino, $C_{2-8}$ dialkylamino, halo, $C_{1-6}$ alkyl, $C_{1-6}$ haloalkyl, aryl, arylalkyl, heteroaryl, heteroarylalkyl, cycloalkyl or heterocycloalkyl. In some further embodiments, $R^{16}$ and —($CR^9R^{10}$)$_n R^{11}$ together with the C atom to which they are attached form tetrahydrofuranyl, tetrahydropyranyl, pyrrolindinyl, piperidinyl, or piperazinyl, each optionally substituted with 1, 2, 3, 4, or 5 substituents each independently selected from OH, $C_{1-6}$ alkoxy, oxo (i.e. =O), $C_{1-6}$ haloalkoxy, amino, $C_{1-6}$ alkylamino, $C_{2-8}$ dialkylamino, halo, $C_{1-6}$ alkyl, $C_{1-6}$ haloalkyl, aryl, arylalkyl, heteroaryl, heteroarylalkyl, cycloalkyl or heterocycloalkyl.

In some embodiments, $R^6$ is —$NR^8$—C(O)—($CR^9R^{10}$)$_n R^{11}$. In some further embodiments, n is 1, 2, or 3.

In some embodiments, $R^6$ is —$NR^8$—C(O)—$R^{11}$. In some further embodiments, $R^{11}$ is selected from $C_{1-6}$ alkyl, $C_{1-6}$ haloalkyl, aryl, cycloalkyl, heteroaryl, and heterocycloalkyl, each optionally substituted by 1, 2, 3, 4, or 5 substituents independently selected from halo, CN, $NO_2$, $C_{1-6}$ alkyl, $C_{1-6}$ haloalkyl, OH, $C_{1-6}$ alkoxy, and $C_{1-6}$ haloalkoxy.

In some embodiments, $R^6$ is —$NR^8$—C(S)—$R^{11}$. In some further embodiments, $R^{11}$ is selected from $C_{1-6}$ alkyl, $C_{1-6}$ haloalkyl, aryl, cycloalkyl, heteroaryl, and heterocycloalkyl, each optionally substituted by 1, 2, 3, 4, or 5 substituents independently selected from halo, CN, $NO_2$, $C_{1-6}$ alkyl, $C_{1-6}$ haloalkyl, OH, $C_{1-6}$ alkoxy, and $C_{1-6}$ haloalkoxy.

In some embodiments, $R^6$ is $-NR^8-S(O)_2-R^{11}$. In some further embodiments, $R^{11}$ is selected from $C_{1-6}$ alkyl, $C_{1-6}$ haloalkyl, aryl, cycloalkyl, heteroaryl, and heterocycloalkyl, each optionally substituted by 1, 2, 3, 4, or 5 substituents independently selected from halo, CN, $NO_2$, $C_{1-6}$ alkyl, $C_{1-6}$ haloalkyl, OH, $C_{1-6}$ alkoxy, and $C_{1-6}$ haloalkoxy.

In some embodiments, $R^6$ is $-NR^8-C(O)-(CR^9R^{10})_n NHR^{d11}$. In some further embodiments, n is 1, 2, or 3. In yet further embodiments, $R^{d11}$ is selected from $C_{1-6}$ alkyl, aryl, and heteroaryl, each optionally substituted with 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $-Y^1-Z^1$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $S(O)_2R^b$, and $S(O)_2NR^cR^d$. In yet further embodiments, $R^{d11}$ is selected from $C_{1-6}$ alkyl, aryl, and heteroaryl, each optionally substituted with 1, 2, 3, 4, or 5 substituents independently selected from OH, CN, halo, $C_{1-6}$ alkyl, $C_{1-6}$ haloalkyl, $C_{1-6}$ alkoxy, and $C_{1-6}$ haloalkyl.

In some embodiments, $R^6$ is $-NR^8-C(O)-NHR^{d11}$. In some further embodiments, $R^{d11}$ is selected from $C_{1-6}$ alkyl, aryl, and heteroaryl, each optionally substituted with 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $-Y^1-Z^1$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$. In yet further embodiments, $R^{d11}$ is selected from $C_{1-6}$ alkyl, aryl, and heteroaryl, each optionally substituted with 1, 2, 3, 4, or 5 substituents independently selected from OH, CN, halo, $C_{1-6}$ alkyl, $C_{1-6}$ haloalkyl, $C_{1-6}$ alkoxy, and $C_{1-6}$ haloalkyl.

In some embodiments, $R^6$ is $-NR^8-C(S)-(CR^9R^{10})_n R^{11}$.

In some embodiments, $R^6$ is $-NR^8-C(S)-NHR^{d11}$. In some further embodiments, $R^{d11}$ is selected from $C_{1-6}$ alkyl, aryl, and heteroaryl, each optionally substituted with 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $-Y^1-Z^1$, $OR^a$, $OC(O)R^d$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$. In yet further embodiments, $R^{d11}$ is selected from $C_{1-6}$ alkyl, aryl, and heteroaryl, each optionally substituted with 1, 2, 3, 4, or 5 substituents independently selected from OH, CN, halo, $C_{1-6}$ alkyl, $C_{1-6}$ haloalkyl, $C_{1-6}$ alkoxy, and $C_{1-6}$ haloalkyl.

In some embodiments, $R^6$ is $-NR^8-C(R^{12})(R^{13})-(CR^9R^{10})_n R^{11}$; and $R^{12}$ and $R^{13}$ are each, independently, selected from H, and $C_{1-4}$ alkyl. In some further embodiments, $R^{12}$ and $R^{13}$ are each, independently, selected from H, and methyl. In yet further embodiments, $R^{12}$ and $R^{13}$ are both H.

In some embodiments, $R^{11}$ is $S(O)_2R^b$ where $R^b$ is $NH_2$.

In some embodiments, each $R^7$ is independently selected from halo, $C_{1-6}$ alkyl, $C_{1-6}$ haloalkyl, CN, $NO_2$, $-NR^8-C(O)-(CR^9R^{10})_n R^{11}$, OH, $C_{1-6}$ alkoxy, $C_{1-6}$ haloalkoxy, amino, $C_{1-6}$ alkylamino, and $C_{2-8}$ dialkylamino. In some further embodiments, each $R^7$ is independently selected from halo, $C_{1-6}$ alkyl, $C_{1-6}$ haloalkyl, CN, $NO_2$, OH, $C_{1-6}$ alkoxy, $C_{1-6}$ haloalkoxy, amino, $C_{1-6}$ alkylamino, and $C_{2-8}$ dialkylamino. In yet further embodiments, each $R^7$ is independently selected from halo, $C_{1-4}$ alkyl, $C_{1-4}$ haloalkyl, CN, $NO_2$, OH, $C_{1-4}$ alkoxy, $C_{1-4}$ haloalkoxy, amino, $C_{1-4}$ alkylamino, and $C_{2-8}$ dialkylamino.

In some embodiments, each $R^7$ is independently selected from halo, $C_{1-4}$ alkyl, and $C_{1-4}$ haloalkyl.

In some embodiments, each $R^8$ is H or methyl.

In some embodiments, each $R^8$ is H.

In some embodiments, $R^9$ and $R^{10}$ are each, independently, selected from H and methyl.

In some embodiments, $R^9$ and $R^{10}$ are each H.

In some embodiments, each $R^{11}$ is independently selected from H, halo, CN, $NO_2$, $OR^{a11}$, $NR^{c11}R^{d11}$, $NR^{c11}C(O)R^{d11}$, $NR^{c11}C(O)OR^{a11}$, $NR^{c11}C(O)NR^{c11}R^{d11}$, $NR^{c11}S(O)R^{b11}$, $NR^{c11}S(O)_2R^{b11}$, $NR^{c11}S(O)NR^{c11}R^{d11}$, and $NR^{c11}S(O)_2NR^{d11}$.

In some embodiments, each $R^{11}$ is independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, each optionally substituted by 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, $S(O)_2NR^cR^d$, $-S(O)-C_{1-6}$ alkyl, $-S-C_{1-6}$ alkyl, and $-O-S(O)_2-C_{1-6}$ alkyl.

In some embodiments, the compound of Formula I is a compound of Formula II:

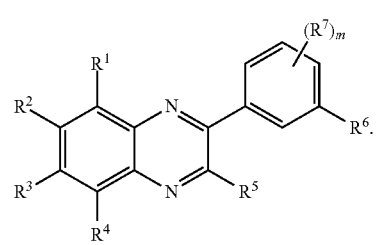

II

In some embodiments, the compound of Formula I is a compound of Formula IIIa:

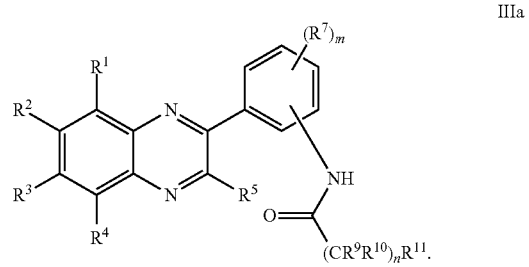

IIIa

In some embodiments, the compound of Formula I is a compound of Formula III:

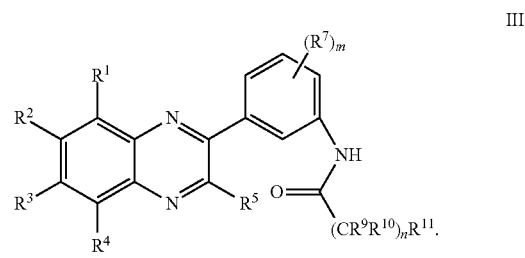

III

In some embodiments, the compound of Formula I is a compound of Formula IVa:

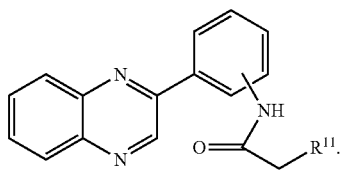

IVa

In some embodiments, the compound of Formula I is a compound of Formula IV:

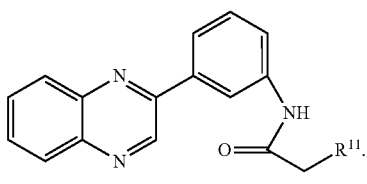

IV

In some embodiments, the compound of Formula I is a compound of Formula Va:

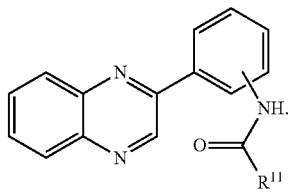

Va

In some embodiments, the compound of Formula I is a compound of Formula V:

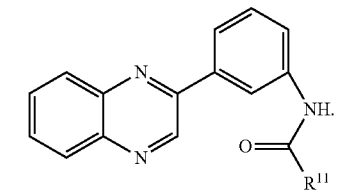

V

In some embodiments, the compound of Formula I is a compound of Formula VI:

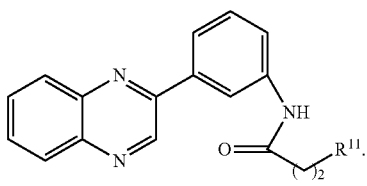

VI

In some embodiments, the compound of Formula I is a compound of Formula VII:

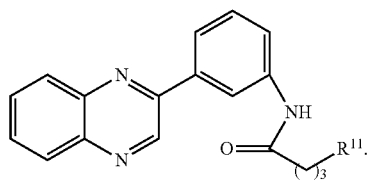

VII

In some embodiments, the compound of Formula I is a compound of Formula VIII:

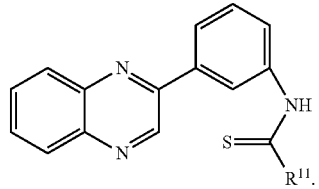

VIII

In some embodiments, the compound of Formula I is a compound of Formula IX:

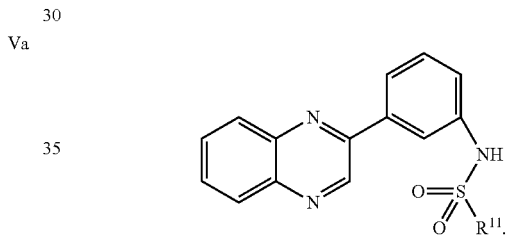

IX

In some embodiments, each $R^{11}$ is independently selected from $C_{1-6}$ alkyl, $C_{1-6}$ haloalkyl, aryl, cycloalkyl, heteroaryl, heterocycloalkyl, halo, CN, $OR^{a11}$, and $NR^{c11}R^{d11}$, wherein each of the $C_{1-6}$ alkyl, $C_{1-6}$ haloalkyl, aryl, cycloalkyl, heteroaryl, and heterocycloalkyl is optionally substituted by 1, 2, 3, 4, or 5 substituents independently selected from halo, CN, $NO_2$, $C_{1-6}$ alkyl, $C_{1-6}$ haloalkyl, OH, $C_{1-6}$ alkoxy, and $C_{1-6}$ haloalkoxy.

In some embodiments, each $R^{11}$ is independently selected from $C_{1-6}$ alkyl, $C_{1-6}$ haloalkyl, aryl, cycloalkyl, heteroaryl, and heterocycloalkyl, each optionally substituted by 1, 2, 3, 4, or 5 substituents independently selected from halo, CN, $NO_2$, $C_{1-6}$ alkyl, $C_{1-6}$ haloalkyl, OH, $C_{1-6}$ alkoxy, and $C_{1-6}$ haloalkoxy.

In some embodiments, each $R^{11}$ is independently selected from halo, CN, $OR^{a11}$, and $NR^{c11}R^{d11}$.

In some embodiments, each $R^{11}$ is independently selected from halo and $NR^{c11}R^{d11}$.

In some embodiments, each $R^{11}$ is independently $NR^{c11}R^{d11}$.

In some embodiments, $R^{c11}$ and $R^{d11}$ are independently selected from H, $C_{1-6}$ alkyl, $C_{1-6}$ haloalkyl, arylalkyl, heteroarylalkyl, cycloalkylalkyl, heterocycloalkylalkyl, aryl, heteroaryl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents each independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, —Y$^1$—Z$^1$, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$.

In some embodiments, R$^{c11}$ and R$^{d11}$ are independently selected from H, C$_{1-6}$ alkyl, C$_{1-6}$ haloalkyl, aryl, heteroaryl, cycloalkyl, and heterocycloalkyl, wherein each of the C$_{1-6}$ alkyl, C$_{1-4}$ haloalkyl, aryl, heteroaryl, cycloalkyl, and heterocycloalkyl is optionally substituted with 1, 2, 3, 4, or 5 substituents independently selected from halo, CN, NO$_2$, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, —Y$^1$—Z$^1$, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$.

In some embodiments, R$^{c11}$ and R$^{d11}$ are independently selected from H and C$_{1-6}$ alkyl.

In some embodiments, one of R$^{c11}$ and R$^{d11}$ is H, and the other of R$^{c11}$ and R$^{d11}$ is selected from C$_{1-6}$ alkyl, C$_{1-6}$ haloalkyl, aryl, heteroaryl, cycloalkyl, and heterocycloalkyl, wherein each of the C$_{1-6}$ alkyl, C$_{1-6}$ haloalkyl, aryl, heteroaryl, cycloalkyl, and heterocycloalkyl is optionally substituted with 1, 2, 3, 4, or 5 substituents independently selected from halo, CN, NO$_2$, C$_{1-6}$ alkyl, C$_{2-6}$ alkenyl, C$_{2-4}$ alkynyl, C$_{1-6}$ haloalkyl, aryl, cycloalkyl, heteroaryl, heterocycloalkyl, —Y$^1$—Z$^1$, OR$^a$, OC(O)R$^b$, OC(O)NR$^c$R$^d$, C(O)R$^b$, C(O)NR$^c$R$^d$, C(O)OR$^a$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$.

In some embodiments, one of R$^{c11}$ and R$^{d11}$ is H, and the other of R$^{c11}$ and R$^{d11}$ is selected from C$_{1-6}$ alkyl, aryl, and heteroaryl, each optionally substituted with 1, 2, 3, 4, or 5 substituents independently selected from halo, CN, NO$_2$, C$_{1-6}$ alkyl, C$_{2-6}$ alkenyl, C$_{2-4}$ alkynyl, C$_{1-6}$ haloalkyl, aryl, cycloalkyl, heteroaryl, heterocycloalkyl, —Y$^1$—Z$^1$, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$. In yet further embodiments, R$^{d11}$ is selected from C$_{1-6}$ alkyl, aryl, and heteroaryl, each optionally substituted with 1, 2, 3, 4, or 5 substituents independently selected from OH, CN, halo, C$_{1-6}$ alkyl, C$_{1-6}$ haloalkyl, C$_{1-6}$ alkoxy, and C$_{1-6}$ haloalkyl.

In some embodiments, one of R$^{c11}$ and R$^{d11}$ is H, and the other of R$^{c11}$ and R$^{d11}$ is selected from C$_{1-6}$ alkyl.

In some embodiments, R$^{c11}$ and R$^{d11}$ together with the N atom to which they are attached form a 4-, 5-, 6- or 7-membered heterocycloalkyl group, each optionally substituted with 1, 2, 3, 4, or 5 substituents each independently selected from halo, CN, NO$_2$, C$_{1-6}$ alkyl, C$_{2-6}$ alkenyl, C$_{2-6}$ alkynyl, C$_{1-6}$ haloalkyl, —Y$^1$—Z$^1$, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$.

In some embodiments, R$^{c11}$ and R$^{d11}$ together with the N atom to which they are attached form an azetidinyl, pyrrolidinyl, piperidinyl, piperazinyl, or morpholinyl group, each optionally substituted with 1, 2, 3, 4, or 5 substituents independently selected from halo, CN, NO$_2$, C$_{1-6}$ alkyl, C$_{2-6}$ alkenyl, C$_{2-6}$ alkynyl, C$_{1-6}$ haloalkyl, —Y$^1$—Z$^1$, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$.

In some embodiments, R$^{c11}$ and R$^{d11}$ together with the N atom to which they are attached form a pyrrolidinyl, piperidinyl, piperazinyl, or morpholinyl group, each optionally substituted with 1, 2, 3, 4, or 5 substituents independently selected from halo, CN, NO$_2$, C$_{1-6}$ alkyl, C$_{2-6}$ alkenyl, C$_{2-6}$ alkynyl, C$_{1-4}$ haloalkyl, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$.

In some embodiments, R$^{c11}$ and R$^{d11}$ together with the N atom to which they are attached form a pyrrolidinyl or piperidinyl group, each optionally substituted with 1, 2, 3, 4, or 5 substituents each independently selected from halo, CN, NO$_2$, C$_{1-6}$ alkyl, C$_{2-6}$ alkenyl, C$_{2-6}$ alkynyl, C$_{1-6}$ haloalkyl, —Y$^1$—Z$^1$, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$.

In some embodiments, R$^{c11}$ and R$^{d11}$ together with the N atom to which they are attached form a piperazinyl group optionally substituted with 1, 2, 3, 4, or 5 substituents independently selected from halo, CN, NO$_2$, C$_{1-6}$ alkyl, C$_{2-6}$ alkenyl, C$_{2-6}$ alkynyl, C$_{1-6}$ haloalkyl, —Y$^1$—Z$^1$, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$.

In some embodiments, each Y$^1$ is independently selected from absent, C$_{1-6}$ alkylenyl, —(CR$^{14}$R$^{15}$)$_{p1}$—C(O)—(CR$^{14}$R$^{15}$)$_{p2}$—, —(CR$^{14}$R$^{15}$)$_{p1}$—C(O)O—(CR$^{14}$R$^{15}$)$_{p2}$—, —(CR$^{14}$R$^{15}$)$_{p1}$—C(O)NR$^e$—(CR$^{14}$R$^{15}$)$_{p2}$—, —(CR$^{14}$R$^{15}$)$_{p1}$—S(O)$_2$—(CR$^{14}$R$^{15}$)$_{p2}$—, and —(CR$^{14}$R$^{15}$)$_{p1}$—S(O)$_2$NR$^e$—(CR$^{14}$R$^{15}$)$_{p2}$—; and each Z$^1$ is independently selected from C$_{1-6}$ alkyl, C$_{1-6}$ haloalkyl, arylalkyl, heteroarylalkyl, aryl, and heteroaryl, each optionally substituted by 1, 2, 3, 4, or 5 substituents independently selected from C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, halo, CN, NO$_2$, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$.

In some embodiments, R$^{c11}$ and R$^{d11}$ together with the N atom to which they are attached form a moiety of structure QQ1:

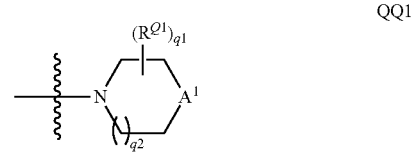

wherein:
each R$^{Q1}$ is independently selected from halo, CN, NO$_2$, C$_{1-6}$ alkyl, C$_{2-6}$ alkenyl, C$_{2-6}$ alkynyl, C$_{1-6}$ haloalkyl, —Y$^1$—Z$^1$, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$;
A$^1$ is CH$_2$, O, NH, S, S(O), S(O)$_2$;
q1 is 0, 1, or 2; and
q2 is 0 or 1.

In some further embodiments wherein R$^{c11}$ and R$^{d11}$ together with the N atom to which they are attached form a moiety of structure QQ1, q2 is 1. In yet further embodiments, A$^1$ is CH$_2$ or NH.

In some embodiments, $R^{c11}$ and $R^{d11}$ together with the N atom to which they are attached form a moiety of structure QQ2:

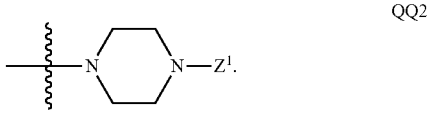

QQ2

In some further embodiments wherein $R^{c11}$ and $R^{d11}$ together with the N atom to which they are attached form a moiety of structure QQ2, $Y^1$ is absent and $Z^1$ is selected from $C_{1-6}$ alkyl, $C_{1-6}$ haloalkyl, arylalkyl, heteroarylalkyl, aryl, and heteroaryl, each optionally substituted by 1, 2, 3, 4, or 5 substituents independently selected from $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$. In yet further embodiments, $Z^1$ is selected from $C_{1-6}$ alkyl, aryl, and heteroaryl, each optionally substituted by 1, 2, 3, 4, or 5 substituents independently selected from $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$. In still further embodiments, $Z^1$ is selected from aryl and heteroaryl, each optionally substituted by 1, 2, 3, 4, or 5 substituents independently selected from $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$.

In some further embodiments wherein $R^{c11}$ and $R^{d11}$ together with the N atom to which they are attached form a moiety of structure QQ2, $Y^1$ is absent and $Z^1$ is selected from phenyl and pyridinyl, each optionally substituted by 1, 2, 3, 4, or 5 substituents independently selected from $C_{1-6}$ alkyl, $C_{2-6}$ alkenyl, $C_{2-6}$ alkynyl, $C_{1-6}$ haloalkyl, aryl, cycloalkyl, heteroaryl, halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$.

In some embodiments, n is 0.
In some embodiments, n is 1.
In some embodiments, n is 2.
In some embodiments, n is 3.
In some embodiments, m is 0.
In some embodiments, m is 1.
In some embodiments, m is 2.

In a further aspect, the present invention provides novel compounds of Formula III:

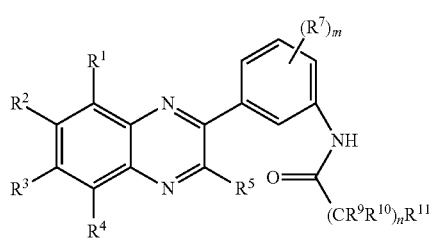

III or pharmaceutically acceptable salts thereof, wherein:

$R^1$, $R^2$, $R^3$, and $R^4$ are each, independently, selected from H, halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$, $C_{1-6}$ alkyl, $C_1$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$;

$R^5$ is selected from H, halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$, $C_{1-6}$ alkyl, haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^c-C(O)NR^cR^d$, $NR^cS(O)_2R^b$, $NR^cS(O)_2NR^cR^d$, $SR^a$, $S(O)_2R^b$, and $S(O)_2NR^cR^d$;

each $R^7$ is independently selected from halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)R^b$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$;

$R^9$ and $R^{10}$ are each, independently, selected from H, $C_{1-4}$ alkyl, and $C_{1-4}$ haloalkyl;

$R^{11}$ is selected from CN and $NR^{c11}R^{d11}$;

$R^{c11}$ and $R^{d11}$ together with the N atom to which they are attached form a moiety of structure QQ:

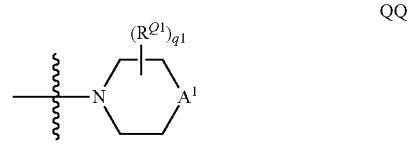

QQ wherein:

each $R^{Q1}$ is independently selected from halo, CN, $NO_2$, $C_{1-6}$ alkyl, $C_{2-6}$ alkenyl, $C_{2-6}$ alkynyl, $C_{1-6}$ haloalkyl, —$Y^1$—$Z^1$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$;

$A^1$ is $CH_2$, NH, S, S(O), $S(O)_2$;

q1 is 0, 1, or 2.

each $Y^1$ is independently selected from absent, $C_{1-6}$ alkylenyl, $C_{2-6}$ alkenylenyl, $C_{2-6}$ alkynylenyl, —$(CR^{14}R^{15})_{p1}$—O—$(CR^{14}R^{15})_{p2}$—, —$(CR^{14}R^{15})_{p1}$—S—$(CR^{14}R^{15})_{p2}$—, —$(CR^{14}R^{15})_{p1}$—$NR^e$—$(CR^{14}R^{15})_{p2}$—, —$(CR^{14}R^{15})_{p1}$—C(O)—$(CR^{14}R^{15})_{p2}$—, —$(CR^{14}R^{15})_{p1}$—C(O)O—$(CR^{14}R^{15})_{p2}$—, —$(CR^{14}R^{15})_{p1}$—$C(O)NR^e$—$(CR^{14}R^{15})_{p2}$—, —$(CR^{14}R^{15})_{p1}$—$S(O)_2$—$(CR^{14}R^{15})_{p2}$—, —$(CR^{14}R^{15})_{p1}$—$S(O)NR^e$—$(CR^{14}R^{15})_{p2}$—, —$(CR^{14}R^{15})_{p1}$—$S(O)_2NR^e$—$(CR^{14}R^{15})_{p2}$—, and —$(CR^{14}R^{15})_{p1}$—$NR^eC(O)NR^f$—$(CR^{14}R^{15})_{p2}$—, wherein each of the $C_{1-6}$ alkylenyl, $C_{2-6}$ alkenylenyl and $C_{2-6}$ alkynylenyl is optionally substituted by 1, 2, or 3 substituents independently selected from halo, OH, CN, amino, $C_{1-6}$ alkylamino, $C_{2-8}$ dialkylamino, $C_{1-6}$ alkyl, $C_{1-6}$ haloalkyl, $C_{1-6}$ alkoxy, $C_{1-6}$ haloalkyl, aryl, arylalkyl, heteroaryl, heteroarylalkyl, cycloalkyl and heterocycloalkyl;

each $Z^1$ is independently selected from $C_{1-6}$ alkyl, $C_{1-6}$ haloalkyl, $C_{2-6}$ alkenyl, $C_{2-6}$ alkynyl, arylalkyl, cycloalkylalkyl, heteroarylalkyl, heterocycloalkylalkyl, aryl, cycloalkyl, heteroaryl, and heterocycloalkyl, each optionally substituted by 1, 2, 3, 4, or 5 substituents independently selected from $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$;

each $R^a$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents each independently selected from OH, CN, amino, $C_{1-6}$ alkylamino, $C_{2-8}$ dialkylamino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

each $R^b$ is independently selected from H, $NH_2$, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents each independently selected from OH, $C_{1-6}$ alkoxy, $C_{1-6}$ haloalkoxy, amino, $C_{1-6}$ alkylamino, $C_{2-8}$ dialkylamino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^c$ and $R^d$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents each independently selected from OH, $C_{1-6}$ alkoxy, $C_{1-6}$ haloalkoxy, amino, $C_{1-6}$ alkylamino, $C_{2-8}$ dialkylamino, halo, $C_{1-6}$ alkyl, $C_{1-6}$ haloalkyl, aryl, arylalkyl, heteroaryl, heteroarylalkyl, cycloalkyl and heterocycloalkyl;

or $R^c$ and $R^d$ together with the N atom to which they are attached form a 4-, 5-, 6- or 7-membered heterocycloalkyl group that is optionally substituted with 1, 2, 3, 4, or 5 substituents each independently selected from OH, $C_{1-6}$ alkoxy, $C_{1-6}$ haloalkoxy, amino, $C_{1-6}$ alkylamino, $C_{2-8}$ dialkylamino, halo, $C_{1-6}$ alkyl, $C_{1-6}$ haloalkyl, aryl, arylalkyl, heteroaryl, heteroarylalkyl, cycloalkyl or heterocycloalkyl;

$R^e$ and $R^f$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, and heterocycloalkyl is optionally substituted with 1, 2, 3, 4, or 5 substituents each independently selected from OH, $C_{1-6}$ alkoxy, $C_{1-6}$ haloalkoxy, amino, $C_{1-6}$ alkylamino, $C_{2-8}$ dialkylamino, halo, $C_{1-6}$ alkyl, $C_{1-6}$ haloalkyl, aryl, arylalkyl, heteroaryl, heteroarylalkyl, cycloalkyl, and heterocycloalkyl;

m is 0, 1, 2, 3, or 4;

n is 1;

each p1 is independently 0, 1, 2, or 3; and each p2 is independently 0, 1, 2, or 3.

In some embodiments of the novel compounds of Formula III or pharmaceutically acceptable salts thereof:

$R^1$, $R^2$, $R^3$, and $R^4$ are each, independently, selected from H, halo, CN, $NO_2$, $C_{1-6}$ alkyl, $C_{1-6}$ haloalkyl, OH, $C_{1-6}$ alkoxy, and $C_{1-6}$ haloalkoxy;

$R^5$ is selected from H, halo, CN, $NO_2$, $C_{1-6}$ alkyl, $C_{1-6}$ haloalkyl, OH, $C_{1-6}$ alkoxy, and $C_{1-6}$ haloalkoxy; and each $R^7$ is independently selected from H, halo, CN, $NO_2$, $C_{1-6}$ alkyl, $C_{1-6}$ haloalkyl, OH, $C_{1-6}$ alkoxy, and $C_{1-6}$ haloalkoxy.

In some embodiments of novel compounds of Formula III or pharmaceutically acceptable salts thereof, $R^1$, $R^2$, $R^3$, $R^4$, $R^5$, and $R^7$ are each, independently, selected from H, halo, $C_{1-6}$ alkyl, and $C_{1-6}$ haloalkyl.

In some embodiments of novel compounds of Formula III or pharmaceutically acceptable salts thereof, $R^9$ and $R^{10}$ are each, independently, selected from H and $C_{1-4}$ alkyl.

In some embodiments of novel compounds of Formula III or pharmaceutically acceptable salts thereof, $R^9$ and $R^{10}$ are both H.

In some embodiments of novel compounds of Formula III or pharmaceutically acceptable salts thereof, $R^{11}$ is CN.

In some embodiments the compounds of Formula II or pharmaceutically acceptable salts thereof, $R^{11}$ is —S(O)—$C_{1-6}$ alkyl.

In some embodiments the compounds of Formula III pharmaceutically acceptable salts thereof, $R^{11}$ is —O—$S(O)_2$—$C_{1-6}$ alkyl.

In some embodiments of novel compounds of Formula III or pharmaceutically acceptable salts thereof:

$R^{11}$ is $NR^{c11}R^{d11}$;

$R^{c11}$ and $R^{d11}$ together with the N atom to which they are attached form a moiety of structure QQ:

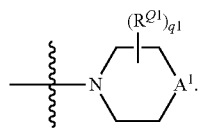

QQ

In some further embodiments of novel compounds of Formula III or pharmaceutically acceptable salts thereof, the moiety of structure QQ is a moiety of structure QQ3:

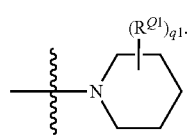

QQ3

In some other embodiments of novel compounds of Formula III or pharmaceutically acceptable salts thereof, the moiety of structure QQ is a moiety of structure QQ2:

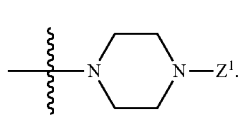

QQ2

In some further embodiments, $Z^1$ is selected from aryl and heteroaryl, each optionally substituted by 1, 2, 3, 4, or 5 substituents independently selected from $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, each of $R^1$, $R^2$, $R^3$, $R^4$, $R^5$, $R^6$, $R^7$, $R^8$, and —$Y^1$—$Z^1$ can be a different moiety selected from the Markush group defining the variable. For another example, where a structure is described having two R groups that are simultaneously present on the same compound; the two R groups can represent different moieties selected from the Markush group defined for R. In another example, when an optionally multiple substituent is designated in the form:

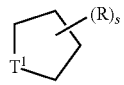

then it is understood that substituent R can occur s number of times on the ring, and R can be a different moiety at each occurrence. Further, in the above example, should the variable $T^1$ be defined to include hydrogens, such as when $T^1$ is said to be $CH_2$, NH, etc., any floating substituent such as R in the above example, can replace a hydrogen of the $T^1$ variable as well as a hydrogen in any other non-variable component of the ring.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

As used herein, the term "alkyl" is meant to refer to a saturated hydrocarbon group which is straight-chained or branched. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylene" refers to a divalent alkyl linking group. An example of alkylene is methylene ($CH_2$).

As used herein, "alkenyl" refers to an alkyl group having one or more double carbon-carbon bonds. Example alkenyl groups include, but are not limited to, ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include, but are not limited to, ethynyl, propynyl, and the like. The term "alkynylenyl" refers to a divalent linking alkynyl group.

As used herein, "haloalkyl" refers to an alkyl group having one or more halogen substituents. Example haloalkyl groups include, but are not limited to CF3, $C_2F_5$, $CHF_2$, $CCl_3$, $CHCl_2$, $C_2Cl_5$, $CH_2CF_3$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms. In some embodiments, aryl groups have from 6 to about 10 carbon atoms.

As used herein, "cycloalkyl" refers to non-aromatic cyclic hydrocarbons including cyclized alkyl, alkenyl, and alkynyl groups that contain up to 20 ring-forming carbon atoms. Cycloalkyl groups can include mono- or polycyclic (e.g., having 2, 3 or 4 fused rings) ring systems as well as spiro ring systems. A cycloalkyl group can contain from 3 to about 15, from 3 to about 10, from 3 to about 8, from 3 to about 6, from 4 to about 6, from 3 to about 5, or from 5 to about 6 ring-forming carbon atoms. Ring-forming carbon atoms of a cycloalkyl group can be optionally substituted by oxo or sulfido. Example cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl).

As used herein, "heteroaryl" groups refer to an aromatic heterocycle having up to 20 ring-forming atoms and having at least one heteroatom ring member (ring-forming atom) such as sulfur, oxygen, or nitrogen. In some embodiments, the heteroaryl group has at least one or more heteroatom ring-forming atoms each independently selected from sulfur, oxygen, and nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 1 to about 5, from about 1 to about 4, from about 1 to about 3, from about 1 to about 2, carbon atoms as ring-forming atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles having up to 20 ring-forming atoms including cyclized alkyl, alkenyl, and alkynyl groups where one or more of the ring-forming carbon atoms is replaced by a heteroatom such as an O, N, or S atom. Hetercycloalkyl groups can be mono or polycyclic (e.g., both fused and spiro systems). Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, pyrrolidin-2-one-3-yl, and the like. Ring-forming carbon atoms and heteroatoms of a heterocycloalkyl group can be optionally substituted by oxo or sulfido. For example, a ring-forming S atom can be substituted by 1 or 2 oxo [i.e., form a S(O) or S(O)$_2$]. For another example, a ring-forming C atom can be substituted by oxo (i.e., form carbonyl). Also included in the definition of heterocycloalkyl are moieties that have one or more aromatic rings fused (i.e., having a bond in common with) to the nonaromatic heterocyclic ring, for example pyridinyl, thiophenyl, phthalimidyl, naphthalimidyl, and benzo derivatives of heterocycles such as indolene, isoindolene, isoindolin-1-one-3-yl, 4,5,6,7-tetrahydrothieno[2,3-c]pyridine-5-yl, 5,6-dihydrothieno[2,3-c]pyridin-7(4H)-one-5-yl, and 3,4-dihydroisoquinolin-1(2H)-one-3yl groups. Ring-forming carbon atoms and heteroatoms of the heterocycloalkyl group can be optionally substituted by oxo or sulfido. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-haloalkyl group. An example haloalkoxy group is OCF$_3$.

As used herein, "arylalkyl" refers to a C$_{1-6}$ alkyl substituted by aryl and "cycloalkylalkyl" refers to C$_{1-6}$ alkyl substituted by cycloalkyl.

As used herein, "heteroarylalkyl" refers to a C$_{1-6}$ alkyl group substituted by a heteroaryl group, and "heterocycloalkylalkyl" refers to a C$_{1-6}$ alkyl substituted by heterocycloalkyl.

As used herein, "amino" refers to NH$_2$.

As used herein, "alkylamino" refers to an amino group substituted by an alkyl group.

As used herein, "dialkylamino" refers to an amino group substituted by two alkyl groups.

As used here, C(O) refers to C(=O).

As used here, C(S) refers to C(=S).

As used here, S(O) refers to S(=O).

As used here, S(O)$_2$ refers to S(=O)$_2$.

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound. For example, if a methyl group (i.e., CH$_3$) is optionally substituted, then up to 3 hydrogen atoms on the carbon atom can be replaced with substituent groups.

Some compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as □-camphorsulfonic acid. Other resolving agents suitable for fractional crystallization methods include stereoisomerically pure forms of □-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Some compounds of the invention may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Some compounds of the invention further include hydrates and solvates, as well as anhydrous and non-solvated forms.

The term, "compound," as used herein is meant to include all stereoisomers, geometric iosomers, tautomers, and isotopes of the structures depicted.

All compounds and pharmaceutically acceptable salts thereof, can be prepared or present together with other substances such as water and solvents (e.g. hydrates and solvates) or can be isolated.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, or salts thereof, are substantially isolated. By "substantially isolated" is meant that the compound is at least partially or substantially separated from the environment in which is formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

In some embodiments, compounds of the invention are intended to include compounds with stable structures. As used herein, "stable compound" and "stable structure" are meant to indicate a compound that is sufficiently robust to survive isolation to a useful degree of purity from a reaction mixture, and formulation into an efficacious therapeutic agent.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

In some embodiments, the present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

In some embodiments, the present invention also includes quaternary ammonium salts of the compounds described herein, where the compounds are primary amines, secondary amines, or tertiary amines. As used herein, "quaternary ammonium salts" refers to derivatives of the disclosed primary amine, secondary amine, or tertiary amine compounds wherein the parent amine compounds are modified by converting the amines to quaternary ammonium cations via alkylation (and the cations are balanced by anions such as $Cl^-$, $CH_3COO^-$, or $CF_3COO^-$), for example methylation or ethylation.

Synthesis

In some embodiments, compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3r$^d$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

The compounds of invention can be prepared according to the synthetic procedures described below and in the Example section.

As shown in Scheme 1, compound 1-2 can be obtained by reacting compound 1-1 [wherein $Lg^1$ is a leaving group such as halo (e.g., chloro or bromo)] with amine $HNR^{c11}R^{d11}$ under suitable conditions, for example, in the presence of a suitable base [such as an organic base e.g. a tertiary amine such as triethylamine (TEA), diisopropylethylamine (DIPEA), N-methylmorpholine (NMM), or pyridine].

Scheme 1

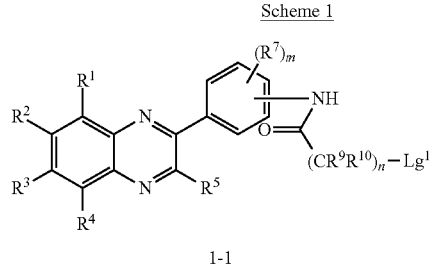

1-1

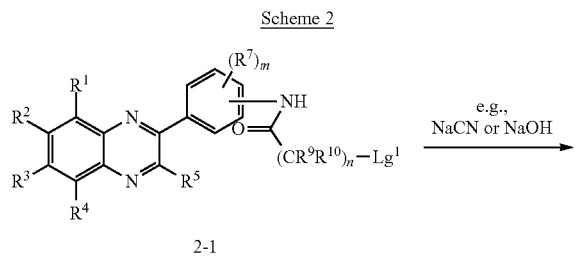

1-2

As shown in Scheme 2, compound 1-1 [wherein $Lg^1$ is a leaving group such as halo (e.g., chloro or bromo)] can undergo nucleophilic substitution reaction with a suitable nucleophile such as OH⁻, CN⁻, or $(OR^{d11})^-$ under suitable conditions to give compound 2-2.

Scheme 2

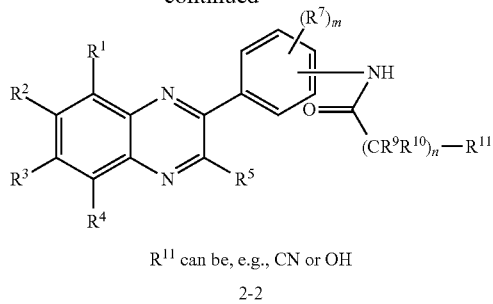

2-1

$R^{11}$ can be, e.g., CN or OH 2-2

As shown in Scheme 3, amine 3-1 can be reacted with a suitable isocyanate $R^{d11}NCO$ (where $R^{d11}$ can be alkyl, phenyl, or the like) to give urea 3-2. Thiourea 3-3 can be made by reacting amine 3-1 with a suitable thioisocyanate $R^{d11}NCS$.

Scheme 3

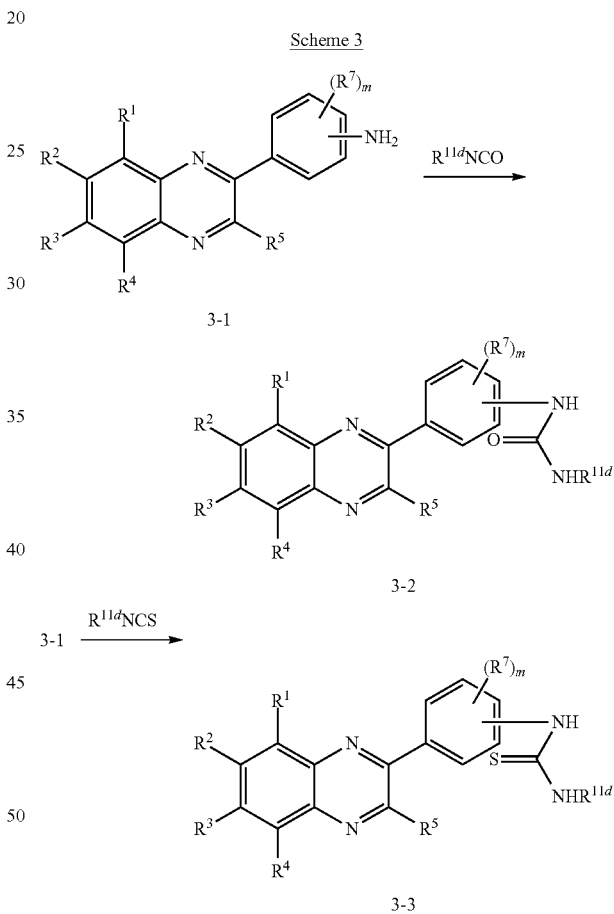

As shown in Scheme 4, ketone 4-1 can be halogened (for example, reacted with bromine) under suitable conditions to afford a halogenated ketone such as brominated compound 4-2. Compound 4-2 can be reacted with benzene-diamine 4-3 to give the quinoxaline compound 4-4. Reduction of the nitro group of compound 4-4 under suitable conditions (for example, in the presence of $SnCl_2$) affords amine compound 4-5. The amine compound 4-5 can undergo further chemical modification such as those shown in Scheme 1. For another example, the amine compound 4-5 can be converted to amide by reacting compound 4-5 with a carbonyl halide compound such as compound 4-6 to afford amide compound 4-7. For yet another example, the amine compound 4-5 can be converted to amide by reacting compound 4-5 with a thionyl halide compound such as compound 4-8 to afford compound 4-9.

Scheme 4

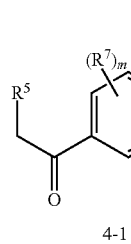

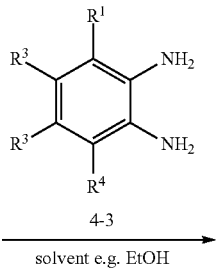

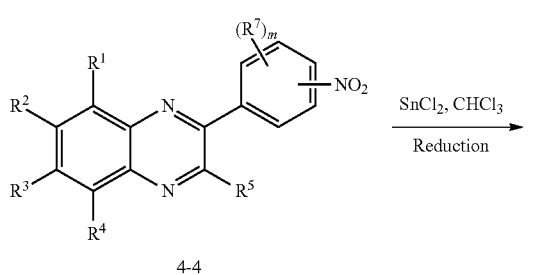

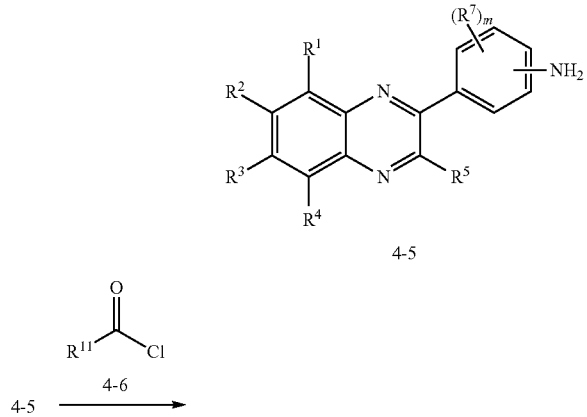

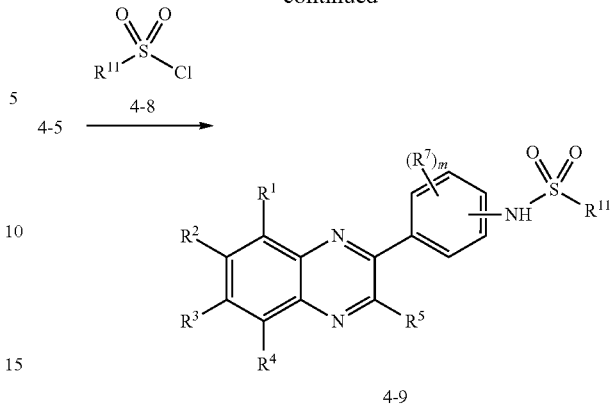

Those skilled in the art can recognize that in all of the schemes described herein, if there are functional (reactive) groups present on a substituent group such as $R^1$, $R^2$, $R^3$, $R^4$, $R^5$, $R^6$, $R^7$, $R^8$, $R^9$, $R^{10}$, $Y^1$, $Z^1$, etc., further modification can be made if appropriate and/or desired. For example, a CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as mesylate, which in turn is suitable for nucleophilic substitution, such as by CN. For another example, an —S— can be oxidized to —S(O)— and/or —S(O)$_2$—. For yet another example, unsaturated bond such as C≡C or C≡C can be reduced to saturated bond by hydrogenation. In some embodiments, a primary amine or a secondary amine moiety (present on a substituent group such as $R^1$, $R^2$, $R^3$, $R^4$, $R^5$, $R^6$, $R^7$, $R^8$, $R^9$, $R^{10}$, $Y^1$, $Z^1$, etc.) can be converted to amide, sulfonamide, urea, or thiourea moiety by reacting it with an appropriate reagent such as an acid chloride, a sulfonyl chloride, an isocyanate, or a thioisocyanate compound. In some embodiments, a primary amine, a secondary amine, or a tertiary amine moiety (present on a substituent group such as $R^1$, $R^2$, $R^3$, $R^4$, $R^5$, $R^6$, $R^7$, $R^8$, $R^9$, $R^{10}$, $L^1$, $L^2$, etc.) can be alkylated to form a quaternary ammonium salt. One skilled in the art will recognize further such modifications. Thus, a compound of Formula I (such as compound 1-2 of Scheme 1) having a substituent which contains a functional group can be converted to another compound of Formula I having a different substituent group.

As used herein, the term "reacting" refers to the bringing together of designated chemical reactants such that a chemical transformation takes place generating a compound different from any initially introduced into the system. Reacting can take place in the presence or absence of solvent.

Methods

Certain compounds of the invention have an IC$_{50}$ with respect to JAK3 less than about 1000 nM, 500 nM, 200 nM, 100 nM, 50 nM, 20 nM, 10 nM, 5 nM, 2 nM, or 1 nM. Accordingly, compounds of the invention can modulate activity of JAK3. The term "modulate" is meant to refer to an ability to increase or decrease the activity of JAK3. Accordingly, compounds of the invention can be used in methods of modulating a JAK3 by contacting the JAK3 with any one or more of the compounds or compositions described herein. In some embodiments, compounds of the present invention can act as inhibitors of JAK3. In further embodiments, the compounds of the invention can be used to modulate (e.g. inhibiting) activity of a JAK3 in an individual in need of modulation (e.g. inhibition) of the enzyme by administering a modulating (e.g. inhibiting) amount of a compound of the invention.

In some embodiments, the modulating (e.g. inhibiting) JAK3 is selective over other members of the JAK family [i.e., JAK1, JAK2, and TYK2]. In some embodiments, the compounds used in the invention show 25% or more of binding to JAK3 comparing to other members of the JAK family. In some embodiments, the IC50 of compounds of the invention with respect to JAK1, JAK2, or TYK2 is greater than 1 µM, 5 µM, 10 µM, 20 µM, 50 µM, 100 µM, or 200 µM. In some embodiments, the relative ratio of IC50 of the compounds of invention with respect to JAK1, JAK2, or TYK2 to that with respect to JAK3 is greater than about 5:1, 10:1, 20:1, 50:1, 100:1, 200:1, 500:1, 1000:1, 2000:1, 5000:1, or 10000:1.

Another aspect of the present invention pertains to methods of treating a JAK3-associated disease or disorder in an individual (e.g., patient) by administering to the individual a therapeutically effective amount or dose of a compound of the present invention or a pharmaceutical composition thereof. In some embodiments, the individual has been diagnosed to have a JAK3-associated disease or disorder and is in need of treatment for the disease or disorder. A JAK3-associated disease can include any disease, disorder, or condition that is directly or indirectly linked to expression or activity of the JAK3, including over expression and/or abnormal activity levels. A JAK3-associated disease can also include any disease, disorder or condition that can be prevented, ameliorated, or cured by modulating JAK activity.

Examples of JAK3-associated diseases include diseases involving the immune system including, for example, organ transplant rejection [e.g., allograft rejection and graft versus host disease (GVHD)]. Some other examples of JAK3-associated diseases include a mast cell mediated immediate hypersensitivity reaction, platelet aggregation, and thrombus formation.

Further examples of JAK3-associated diseases include autoimmune diseases such as multiple sclerosis, rheumatoid arthritis, juvenile arthritis, psoriatic arthritis, type I diabetes, lupus, psoriasis, inflammatory bowel disease (e.g, ulcerative colitis and Crohn's disease), ankylosing spondylitis, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP). In some embodiments, JAK-associated diseases include rheumatoid arthritis.

Further examples of JAK3-associated diseases include allergic or type I hypersensitivity reaction such as urticaria and eczema, conjunctivitis, rhinorrhea, rhinitis asthma, gastroenteritis, familial amyotrophic lateral sclerosis, lupus, multiple sclerosis, Type I diabetes and complications from diabetes, cancer, asthma, rhinitis, atopic dermatitis, autoimmune thyroid disorders, Alzheimer's disease, leukemia, thrombus and other autoimmune disease.

Further examples of JAK3-associated diseases or conditions include skin disorders such as psoriasis (for example, psoriasis vulgaris), atopic dermatitis, alopecia areata, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK3 inhibitor of the invention together with the agent causing unwanted sensitization can be helpful in treating such unwanted sensitization or dermatitis. In some embodiments, the skin disorder is treated by topical administration of at least one JAK inhibitor of the invention.

The JAK3 antagonists/inhibitors described herein can be used to treat any of the JAK3-associated diseases, disorders or conditions, or any combination thereof.

Treatment of the diseases/disorders herein includes treating one or more symptoms associated with the diseases/disorders. For example, symptoms of a JAK3-associated skin disorder (such as psoriasis, atopic dermatitis, skin rash, skin irritation, or skin sensitization) include itching (prutius).

As used herein, the term "contacting" refers to the bringing together of indicated moieties in an in vitro system or an in vivo system. For example, "contacting" a JAK3 with a compound of the invention includes the administration of a compound of the present invention to an individual or patient, such as a human, having a JAK3, as well as, for example, introducing a compound of the invention into a sample containing a cellular or purified preparation containing the JAK3.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting/retarding the disease; for example, inhibiting/retarding a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or completely eliminating/curing the disease. As used herein, treating a disease further includes treating one or more symptoms associated with the disease.

Combination Therapies

One or more additional pharmaceutical agents such as, for example, anti-inflammatory agents, steroids, immunosuppressants, as well as another JAK3 and/or other kinase inhibitors, such as BTK kinase and JAK2 kinase such as, for example, those described in WO 99/65909, WO 00/00202, and/or WO/2004/099205, or other agents can be used in combination with the compounds of the present invention for treatment of JAK3-associated diseases, disorders or conditions. The one or more additional pharmaceutical agents can be administered to a patient simultaneously or sequentially.

In some embodiments, one or more JAK3 inhibitors/antagonists of the invention can be used in combination with one or more other therapeutics used in the treatment of JAK3-mediated/associated conditions/diseases/disorders, and may improve the treatment response as compared to the response to the other therapeutics alone, without exacerbation of its toxic effects. Additive or synergistic effects are desirable outcomes of combining a JAK3 inhibitor/antagonist of the present invention with one or more additional agent. The additional agents can be combined with the present compounds in a single or continuous dosage form, or the agents can be administered simultaneously or sequentially as separate dosage forms. In some embodiments, one or more additional agents can be administered to a patient in combination with at least one JAK3 inhibitor/antagonist described herein where the additional agents are administered intermittently as opposed to continuously.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nano particulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and can be generally administered in a pharmaceutically effective amount. For example, the dosage of the active compounds of the invention as employed for the treatment of a patient in need thereof (such as an adult human) may range from 0.1 to 3000 mg per day, depending on the route and frequency of administration. Such a dosage corresponds to 0.001 to 50 mg/kg per day. In some embodiments, the dosage of the active compounds of the invention as employed for the treatment of a patient in need thereof (such as an adult human) may range from 1 to 2000 mg per day, from 1 to 1000 mg per day, from 10 to 1000 mg per day, or from 10 to 500 mg per day. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 □g/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in radio-imaging but also in assays, both in vitro and in vivo, for localizing and quantitating the enzyme in tissue samples, including human, and for identifying ligands by inhibition binding of a labeled compound. Accordingly, the present invention includes enzyme assays that contain such labeled compounds.

In some embodiments, the present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$ and $^{131}$I. The radionuclide that is incorporated labeled compounds will depend on the specific application of that radio-labeled compound. For example, for in vitro receptor labeling and competition assays, compounds that incorporate $^{3}$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from $^{3}$H, $^{14}$C, $^{125}$I, $^{35}$S and $^{82}$Br.

In some embodiments, the labeled compounds of the present invention contain a fluorescent label.

Synthetic methods for incorporating radio-isotopes and fluorescent labels into organic compounds are well known in the art.

A labeled compound of the invention (radio-labeled, fluorescent-labeled, etc.) can be used in a screening assay to identify/evaluate compounds. For example, a newly synthesized or identified compound (i.e., test compound) which is labeled can be evaluated for its ability to bind a JAK3 by monitoring its concentration variation when contacting with the JAK3, through tracking the labeling. For another example, a test compound (labeled) can be evaluated for its ability to reduce binding of another compound which is known to bind to JAK3 (i.e., standard compound). Accordingly, the ability of a test compound to compete with the standard compound for binding to the JAK3 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

In some embodiments, the present invention also includes pharmaceutical kits useful, for example, in the treatment or prevention of JAK3-associated diseases or disorders such as allergies, asthma, autoimmune diseases such as transplant rejection, rheumatoid arthritis, amyotrophic lateral sclerosis and multiple sclerosis as well as in solid and hematologic malignancies such as leukemias and lymphomas, and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those, skilled in the art. Instructions, either as inserts or as labels, indicating quantities of the components to be administered, guidelines for administration, and/or guidelines for mixing the components, can also be included in the kit.

Some embodiments of the invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. In some instances where the compounds of the examples were isolated by preparative HPLC in the presence of trifluoroacetic acid (TFA) or other acid, the compound may have been obtained as the corresponding salt. Certain compounds of the Examples were found to be inhibitors of JAK3 according to one or more of the assays provided herein. In some embodiments, the $IC_{50}$ value for the compound of invention with respect JAK3 is less than about 100, 80, 50, 20, 10, 8, 5, 2, or 1 μM. In some embodiments, the $IC_{50}$ value for the compound of invention with respect to JAK3 is less than about 1000, 800, 500, 200, 100, 80, 50, 20, 10, 5, 2, or 1 nM. Certain compounds described in Tables 1 and in the Example section were tested for inhibitory activity of JAK3 targets according to assays such as those described herein or those known in the art (e.g., Ma H et al, Expert Opin. Drug Discov. 3, 607-621 (2008); Olive D M, Expert Rev Proteomics, 1, 327-341 (2004)). For instance, Examples 1, 8, 9, and 16 were found to have $IC_{50}$ values less than 1000 nM, 800 nM, 500 nM, 200 nM, or 100 nM with respect to JAK3. Examples 1, 8, 9, and 16 were found to be JAK3 selective: they have $IC_{50}$ values greater than 10 μM, 15 μM, or 20 μM with respect to JAK1, JAK2, and/or TYK2, Some exemplary data of the compounds of the invention are shown in Table 1 in the experimental section.

EXAMPLES

Example 1

2-chloro-N-(3-quinoxalin-2-ylphenyl)acetamide

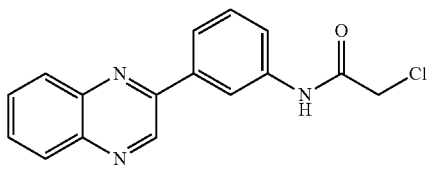 [SMILES: O=C(CCl)Nc1cccc(-c2cnc3ccccc3n2)c1]

Step 1. 2-(3-nitrophenyl)quinoxaline

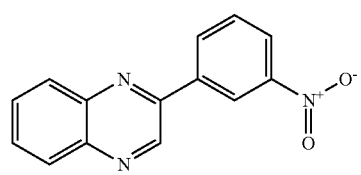 [SMILES: O=[N+]([O-])c1cccc(-c2cnc3ccccc3n2)c1]

A mixture of 2-bromo-1-(3-nitrophenyl)ethanone (20.5 g, 84 mmol), 1,2-phenylenediamine (8.6 g, 80 mmol) and sodium acetate (12.2 g, 90 mmol) in ethanol (EtOH) (250 mL) was heated at reflux for 5 hrs. The reaction mixture was cooled to room temperature, filtered, washed with EtOH and water, and dried to afford 2-(3-nitrophenyl)quinoxaline (11.9 g, 59% yield). LCMS calculated for $C_{14}H_9N_3O_2$ (M+H): 252.25. found 252; (M+H+MeCN): 293.10. found 293. $^1$H-NMR (400 MHz, DMSO-d6) $\delta_H$: 9.62 (1H, s), 9.12 (1H, m), 8.81 (1H, m), 7.42 (1H, m), 8.30-8.10 (2H, m), 8.00-7.82 (3H, m).

Step 2. (3-quinoxalin-2-ylphenyl)amine

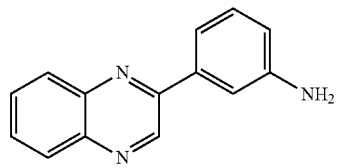 [SMILES: Nc1cccc(-c2cnc3ccccc3n2)c1]

A solution of 2-(3-nitrophenyl)quinoxaline (9.4 g, 37.4 mmol), $SnCl_2.H_2O$ (28 g, 13.48 mmol) in $CHCl_3$ (95 mL) was heated to 90° C. for 15 minutes, cooled to room temperature, added to ice water (190 mL), and basified to pH 10 with 50% aqueous NaOH, adding ice as necessary to maintain the temperature below 10° C. The mixture was extracted with ethyl acetate (500 mL), and the organic phase was filtered through a Celite pad, which was washed once with ethyl acetate (150 mL). The combined organics phases were washed with brine and dried, and then solvent was evaporated in vacuo. The resulting solid was recrystallized from toluene to afford (3-quinoxalin-2-ylphenyl)amine (5.6 g, 68% yield). LCMS calculated for $C_{14}H_{11}N_3$ (M+H): 222.26. found 222. $^1$H-NMR (400 MHz, DMSO-$d_6$) $\delta_H$: 9.42 (1H, s), 8.11-8.00 (2H, m), 7.94-7.75 (2H, m), 7.55 (1H, s), 7.42 (1H, d, J=7 Hz), 7.22 (1H, m), 6.72 (1H, m), 5.42 (2H, br. s).

Step 3.
2-chloro-N-(3-quinoxalin-2-ylphenyl)acetamide

To a solution of (3-quinoxalin-2-ylphenyl)amine (4.43 g, 20 mmol) and $Et_3N$ (3 mL, 22 mmol) in THF (100 mL), chloroacetyl chloride (1.6 mL, 20 mmol) was added dropwise with stirring. The solvent was evaporated in vacuo. The residue was slurred with water, filtered, and dried. The solid was dissolved in hot toluene (300 mL), treated with silica gel, filtered and left to recrystallize to afford 2-chloro-N-(3-quinoxalin-2-ylphenyl)acetamide (4.5 g, 76% yield). LCMS calculated for $C_{16}H_{12}ClN_3O$ (M+H): 298.75. found 298.06. $^1$H-NMR (400 MHz, DMSO-d6) $\delta_H$: 10.6 (1H, br. s), 9.52 (1H, s), 8.54 (1H, m), 8.20-8.05 (3H, m), 7.90-7.70 (3H, m), 7.62-7.51 (1H, m), 4.31 (2H, s).

Example 2

$N^2,N^2$-dimethyl-$N^1$-(3-quinoxalin-2-ylphenyl)glycinamide

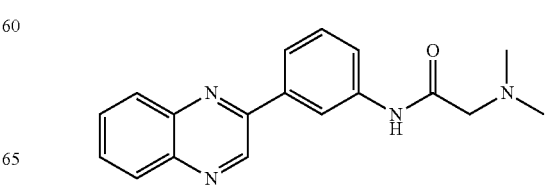

To a solution of 2-chloro-N-(3-quinoxalin-2-ylphenyl)acetamide (67 mg, 0.225 mmol) in THF (3 mL), a 2 M solution of dimethylamine in THF (0.562 mL, 1.152 mmol) was added and the reaction mixture was stirred at room temperature for 48 hrs. The reaction mixture was diluted with dichloromethane (DCM, 5 mL) and solvents evaporated to afford $N^2,N^2$-dimethyl-$N^1$-(3-quinoxalin-2-ylphenyl)glycinamide (25 mg, 36% yield). LCMS calculated for $C_{18}H_{18}N_4O$ (M+H): 307.37. found 307.20. $^1$H-NMR (MeOD, 400 Mhz) $\delta_H$: 9.50 (1H, s), 8.65 (m, 1H), 8.30-8.15 (m, 3H), 8.00-7.87 (m, 3H), 7.60-7.55 (m, 1H), 4.30 (s, 2H), 3.15 (s, 6H).

Example 3

2-pyrrolidin-1-yl-N-(3-quinoxalin-2-ylphenyl)acetamide

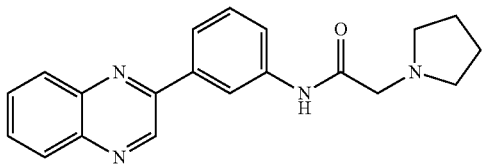 [SMILES: O=C(CN1CCCC1)Nc1cccc(-c2cnc3ccccc3n2)c1]

A solution of 2-chloro-N-(3-quinoxalin-2-ylphenyl)acetamide (100 mg, 0.336 mmol), pyrrolidine (34 µL, 0.403 mmol) and $K_2CO_3$ (112 mg, 0.806 mmol) in MeCN (5 mL) was stirred at 50° C. for 18 hrs. HPLC analysis still showed starting material and therefore, the reaction mixture was further stirred at 100° C. for 1 h to afford completion. The mixture was cooled to room temperature and ethyl acetate (20 mL) was added, the organic phase was washed with water (20 mL) and then brine (20 mL), and dried over $MgSO_4$, and solvent evaporated. The resulting oily solid was dissolved in DCM (5 mL) and stirred overnight with polystyrene methylisocyanate ("PS-isocyanate" 276 mg, 0.4 mmol, 1.46 mmol/g) to remove any excess pyrrolidine. The polymer was filtered and the organic phase was remove in vacuo, to afford 2-pyrrolidin-1-yl-N-(3-quinoxalin-2-ylphenyl)acetamide (45 mg, 40% yield). LCMS calculated for $C_{20}H_{20}N_4O$ (M+H): 333.41. found 333.21. $^1$H-NMR (DMSO-d6, 400 Mhz) $\delta_H$: 9.95 (s, 1H), 9.51 (s, 1H), 8.55 (s, 1H), 8.20-8.14 (m, 2H), 8.08-8.02 (m, 1H), 7.95-7.82 (m, 3H), 7.58-7.50 (m, 1H), 3.40 (s, 2H), 2.65-2.55 (m, 4H), 1.85-1.75 (m, 4H).

Example 4

2-[4-(4-chlorophenyl)piperazin-1-yl]-N-(3-(quinoxalin-2-yl)phenyl)acetamide

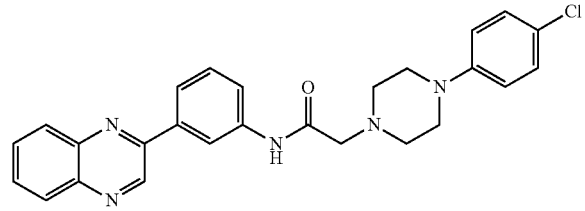 [SMILES: O=C(CN1CCN(c2ccc(Cl)cc2)CC1)Nc1cccc(-c2cnc3ccccc3n2)c1]

A slurry of 2-chloro-N-(3-quinoxalin-2-ylphenyl)acetamide (100 mg, 0.336 mmol), 1-(4-chlorophenyl)piperazine dihydrochloride (100 mg, 0.367 mmol) and $K_2CO_3$ (149 mg, 1.075 mmol) in MeCN (5 mL) was heated at reflux for 24 hrs. The reaction mixture was diluted with ethyl acetate (20 mL), and the organic phase washed with water (20 mL) and then brine (20 mL), dried over $MgSO_4$ and evaporated in vacuo. The residue was triturated with diethyl ether and dried in vacuo at 50° C. to afford 2-[4-(4-chlorophenyl)piperazin-1-yl]-N-(3-(quinoxalin-2-yl)phenyl)acetamide (56 mg, 36% yield). LCMS calculated for $C_{26}H_{24}ClN_5O$ (M+H): 458.17. found 458.21. $^1$H-NMR (DMSO-d6, 400 Mhz) $\delta_H$: 10.00 (1H, br. s), 9.51 (1H, s), 8.55 (1H, m), 8.15-8.10 (2H, m), 8.05 (1H, d, 1=7.5 Hz), 7.95-7.80 (3H, m), 7.55 (1H, m), 7.21 (2H, d, J=7.5 Hz), 6.90 (2H, d, J=7.5 Hz), 3.21 (4H, m), 2.61 (4H, m).

Example 5

4-chloro-N-[3-(quinoxalin-2-yl)phenyl]butanamide

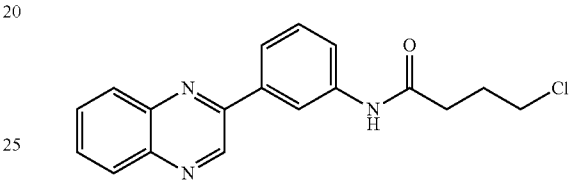

To a solution of (3-quinoxalin-2-ylphenyl)amine (128 mg, 0.578 mmol) and DIEA (115 µL, 0.694 mmol) in THF (5 mL), 3-chloropropionyl chloride (61 µL, 0.636 mmol) was added and the mixture was stirred at room temperature for 48 hrs. The reaction mixture was diluted with ethyl acetate (20 mL), the organic phase was washed with water (10 mL) and then brine (10 mL), dried over $MgSO_4$, and the solvent evaporated in vacuo to afford a light yellow solid. The light yellow solid was triturated with diethyl ether, dried and submitted to preparative LCMS for further purification, to afford 4-chloro-N-[3-(quinoxalin-2-yl)phenyl]butanamide (50 mg, 26% yield). LCMS calculated for $C_{18}H_{16}ClN_3O$ (M+H): 326.79. found 326.00. $^1$H-NMR (DMSO-d6, 400 Mhz) $\delta_H$: 10.20 (1H, br. S), 9.50 (1H, s), 8.55 (1H, m), 8.20-8.15 (2H, m), 8.04 (1H, m), 7.95-7.85 (m, 3H), 7.54 (1H, m), 3.62 (2H, t, 0.1=7 Hz), 2.60 (2H, m), 2.1 (2H, m).

Example 6

N-[3-(quinoxalin-2-yl)phenyl]propionamide

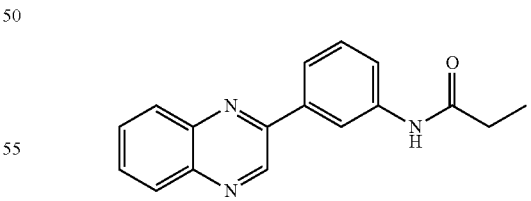

To a solution of (3-quinoxalin-2-ylphenyl)amine (200 mg, 0.904 mmol) and DIEA (180 µL, 1.09 mmol) in THF (5 mL), propionyl chloride (87 µL, 1.0 mmol) was added and the mixture was stirred at room temperature for 3 days. The reaction mixture was diluted with ethyl acetate (20 mL), the organic phase was washed with water (10 mL), brine (10 mL), dried over $MgSO_4$, and the solvent evaporated in vacuo. The resulting solid was triturated with diethyl ether and dried to afford 170 mg (67%) N-[3-(quinoxalin-2-yl)phenyl]propionamide. LCMS calculated for $C_{17}H_{15}N_3O$ (M+H): 278.12. found 276.00. $^1$H-NMR (CDCl$_3$, 400 Mhz) $\delta_H$: 9.44 (1H, br. s), 8.32 (1H, s), 8.14 (m, 2H), 7.41 (1H, d, J=7.5 Hz), 7.88-7.55 (4H, m), 7.52 (m, 1H), 7.40 (1H, br. S), 2.45 (2H, q, J=7 Hz), 1.28 (3H, t, J=7 Hz).

Example 7

N-[3-(quinoxalin-2-yl)phenyl]-2-(1H-1,2,4-triazol-1-yl)acetamide

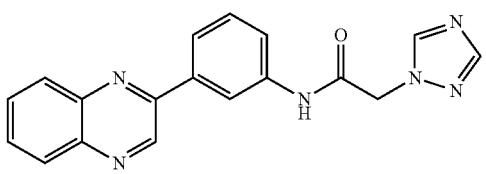 [SMILES: O=C(Cn1cncn1)Nc1cccc(-c2cnc3ccccc3n2)c1]

To a solution of 1,2,4-triazole (18 mg, 0.258 mmol) in DMF (1 mL), NaH (11.5 mg 60% in mineral oil, 0.282 mmol) was added and the slurry was stirred at room temperature for 5 min. To the slurry, 2-chloro-N-(3-quinoxalin-2-ylphenyl)acetamide (70 mg, 0.235 mmol) in DMF (2 mL) was added at room temperature at stirred for 2 days. Water (5 mL) was added and the reaction mixture was extracted with ethyl acetate (25 mL). The organic phase was dried over MgSO$_4$, the solvent evaporate in vacuo, and the resulting solid was purified by preparative LCMS to afford N-[3-(quinoxalin-2-yl)phenyl]-2-(1H-1,2,4-triazol-1-yl)acetamide (56 mg, 72% yield). LCMS calculated for $C_{18}H_{14}N_6O$ (M+H): 331.34. found 331.11. $^1$H-NMR (DMSO-d6, 400 Mhz) $\delta_H$: 10.65 (1H, br. s), 9.52 (1H, s), 8.58 (1H, s), 8.55 (1H, m), 8.12 (1H, m), 8.10 (1H, d, J=7 Hz), 8.04 (1H, s), 7.98-7.80 (3H, m), 7.58 (1H, m), 5.21 (2H, s).

Example 8

2-cyano-N-[3-(quinoxalin-2-yl)phenyl]acetamide

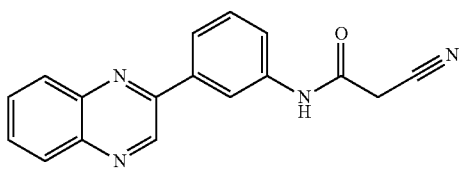 [SMILES: N#CCC(=O)Nc1cccc(-c2cnc3ccccc3n2)c1]

To a solution of 2-chloro-N-(3-quinoxalin-2-ylphenyl)acetamide (276 mg, 0.93 mmol) in EtOH (8 mL), NaCN (50 mg, 1.02 mmol) was added and the reaction mixture was heated at reflux for 21 hrs. After cooling to room temperature, water (10 mL) was added and the reaction mixture was extracted with ethyl acetate (20 mL). The organic phase was washed with brine (20 mL), dried over MgSO$_4$, and the residue was purified by flash chromatography (Flash Master, 5 g Isolute Silica column, gradient 0 to 5 min hexane, then ethyl acetate up to 50% over 20 min). The isolated solid was triturated with Et$_2$O (10 mL) and filtered to afford 2-cyano-N-[3-(quinoxalin-2-yl)phenyl]acetamide as a light-yellow solid (27 mg, 10% yield). LCMS calculated for $C_{17}H_{12}N_4O$ (M+H): 289.30. found 289.00. $^1$H-NMR (DMSO-d6, 400 Mhz) $\delta_H$: 10.55 (1H, br. S), 9.52 (1H, s), 8.48 (1H, m), 8.20-8.12 (2H, m), 8.10 (1H, d, J=7 Hz), 7.98-7.80 (3H, m), 7.58 (1H, m), 3.95 (2H, s).

Example 9

2-(piperidin-1-yl)-N-[3-(quinoxalin-2-yl)phenyl]acetamide

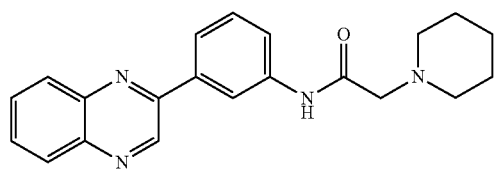 [SMILES: O=C(CN1CCCCC1)Nc1cccc(-c2cnc3ccccc3n2)c1]

To a slurry of 2-chloro-N-(3-quinoxalin-2-ylphenyl)acetamide (100 mg, 0.336 mmol) and K$_2$CO$_3$ (56 mg, 0.403 mmol) in MeCN (5 mL), piperidine (35 μL, 0.353 mmol) was added and the reaction mixture was stirred at reflux for 18 hrs. The solvent was evaporated in vacuo and the residue was purified by flash chromatography (Flash Master, Isolute 5 g silica, gradient 0-5 min, 100% hexane and then 0-100% ethyl acetate over 40 min) to afford 2-(piperidin-1-yl)-N-[3-(quinoxalin-2-yl)phenyl]acetamide (50 mg, 42% yield). LCMS calculated for $C_{21}H_{22}N_4O$ (M+H): 347.18. found 347. $^1$H-NMR (DMSO-d6, 400 Mhz) $\delta_H$: 9.88 (1H, br. s), 9.48 (1H, s), 8.54 (1H, m), 8.12-8.10 (2H, m), 7.98 (1H, d, J=7 Hz), 7.91-7.81 (3H, m), 7.52 (1H, m), 3.12 (2H, s), 2.55-2.53 (4H, m), 1.61-1.55 (4H, m), 1.42-1.36 (2H, m).

Example 10

1-(4-methoxyphenyl)-3-[3-(quinoxalin-2-yl)phenyl]urea

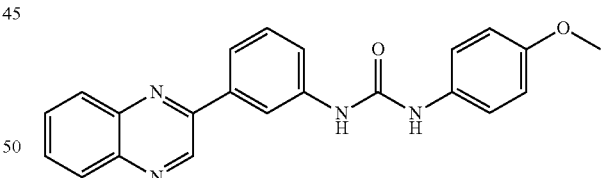

To a solution of (3-quinoxalin-2-ylphenyl)amine (2.21 g, 10 mmol) in hot toluene, 4-methoxyphenyl isocyanate (1.42 g, 10 mmol) was added and the reaction mixture was heated at reflux for 2 hrs. The mixture was cooled to room temperature, the resulting precipitate was filtered, washed with hexane and dried to afford 1-(4-methoxyphenyl)-3-[3-(quinoxalin-2-yl)phenyl]urea (2.3 g, 62% yield). LCMS calculated for $C_{22}H_{18}N_4O_2$ (M+H): 370.41. found 371. $^1$H-NMR (DMSO-d6, 250 Mhz) $\delta_H$: 9.52 (1H, s), 8.95 (1H, br. s), 8.55 (1H, br. s), 8.42 (1H, m), 8.20-8.10 (2H, m), 7.96-7.80 (3H, m), 7.75-7.65 (1H, m), 7.55-7.46 (1H, m), 7.45-7.35 (2H, m), 6.92-6.85 (2H, m), 3.72 (3H, s).

Example 11

1-methyl-3-[3-(quinoxalin-2-yl)phenyl]thiourea

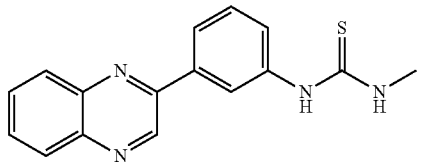

To a solution of (3-quinoxalin-2-ylphenyl)amine (2.21 g, 10 mmol) in hot toluene (80 mL), methyl isothiocyanate (0.73 g, 10 mmol) was added and the reaction mixture was heated overnight at reflux. The mixture was cooled to room temperature, the resulting precipitate was filtered to afford 1-methyl-3-[3-(quinoxalin-2-yl)phenyl]thiourea (2.0 g, 68% yield). LCMS calculated for $C_{16}H_{14}N_4S$ (M+H): 295.38. found 295. $^1$H-NMR (DMSO-d6, 250 Mhz) $\delta_H$: 9.85 (1H, br. s), 9.55 (1H, s), 8.40-8.30 (1H, m), 8.20-8.00 (3H, m), 7.98-7.80 (3H, m), 7.70-7.60 (1H, m), 7.60-7.45 (1H, m).

Example 12

N-[3-(quinoxalin-2-yl)phenyl]furan-2-carboxamide

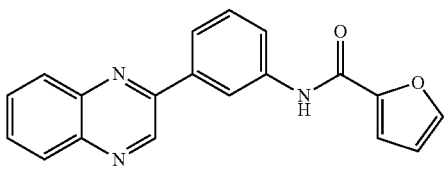 [SMILES: O=C(Nc1cccc(-c2cnc3ccccc3n2)c1)c1ccco1]

A solution of (3-quinoxalin-2-ylphenyl)amine (2.21 g, 0.01 mol) in pyridine (10 mL) was cooled to 0° C. and 2-furoyl chloride (1 mL, 0.01 mol) was added dropwise over 10 min. The reaction mixture was stirred overnight at room temperature, diluted with water (50 mL), and stirred until precipitate formed. The solid was filtered, dried, and recrystallized from toluene to afford N-[3-(quinoxalin-2-yl)phenyl]furan-2-carboxamide (2.4 g, 76%). LCMS calculated for $C_{19}H_{13}N_3O_2$ (M+H): 316.10. found 316. $^1$H-NMR (DMSO-d6, 250 Mhz) $\delta_H$: 10.45 (1H, s), 9.51 (1H, s), 8.68 (1H, s), 8.22-7.80 (7H, m), 7.61 (1H, m), 7.40 (1H, m), 6.81 (1H, m).

Example 13

N-[3-(quinoxalin-2-yl)phenyl]thiophene-2-sulfonamide

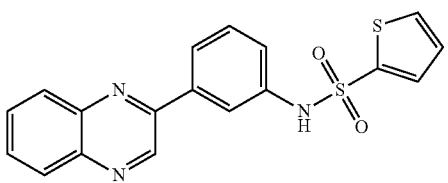

A solution of (3-quinoxalin-2-ylphenyl)amine (2.21 g, 0.01 mol) in pyridine (10 mL) was cooled to 0° C. and 2-thiophenecarbonyl chloride (1.86 g, 0.01 mol) was added in small portions over 15 min. The reaction mixture was stirred overnight at room temperature, diluted with water (50 mL), and stirred until precipitate formed. The solid was filtered, dried and recrystallized from toluene (75 mL), filtered through a plug of silica to afford N-[3-(quinoxalin-2-yl)phenyl]thiophene-2-sulfonamide (2.6 g, 71% yield). LCMS calculated for $C_{18}H_{13}N_3O_2S_2$ (M+H): 368.04. found 368. $^1$H-NMR (DMSO-d6, 250 Mhz) $\delta_H$: 10.70 (1H, br. s), 9.45 (1H, s), 8.20-7.80 (7H, m), 7.60 (1H, m), 7.50 (1H, m), 7.35 (1H, m), 7.10 (1H, m).

Example 14

N-[3-(quinoxalin-2-yl)phenyl]cyclopropanecarboxamide

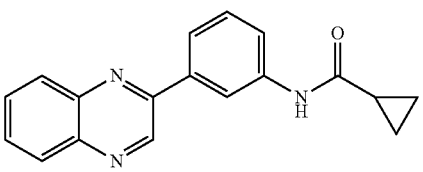

A solution of (3-quinoxalin-2-ylphenyl)amine (2.21 g, 0.01 mol) in pyridine (10 mL) was cooled to 0° C. and cyclopropanecarbonyl chloride (0.91 mL, 0.01 mol) was added dropwise over 10 min. The reaction mixture was stirred overnight at room temperature, diluted with water (50 mL) and stirred for 30 min. The resulting solid was filtered, dried, and recrystallized from toluene to afford N-[3-(quinoxalin-2-yl)phenyl]cyclopropanecarboxamide (2.0 g, 69% yield). LCMS calculated for $C_{18}H_{15}N_3O$ (M+H): 290.34. found 290. $^1$H-NMR (DMSO-d6, 250 Mhz) $\delta_H$: 10.45 (1H, br. s), 9.48 (1H, s), 8.52 (1H, s), 8.20-8.05 (2H, m), 8.05-7.80 (4H, m), 7.50 (1H, m), 1.90-1.75 (1H, m), 1.40-1.32 (4H, m).

Example 15

N-[3-(quinoxalin-2-yl)phenyl]methanesulfonamide

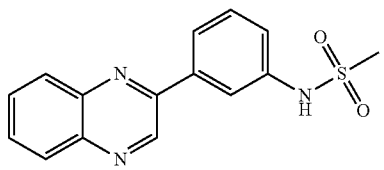

To a solution of (3-quinoxalin-2-ylphenyl)amine (2.21 g, 0.01 mol) in pyridine (10 mL), methanesulfonyl chloride (0.77 mL, 0.01 mol) was added dropwise at 0-5° C. with stirring. The reaction mixture was stirred overnight at room temperature, and then diluted with water. The resulting solid was filtered and dried to afford N-[3-(quinoxalin-2-yl)phenyl]methanesulfonamide (2.6 g, 87% yield). LCMS calculated for $C_{15}H_{13}N_3O_2S$ (M+H): 300.07. found 300. $^1$H-NMR (DMSO-d6, 250 Mhz) $\delta_H$: 10.01 (1H, br. s), 9.50 (1H, s), 8.20-8.00 (4H, m), 7.95-7.70 (2H, m), 7.60-7.52 (1H, m), 7.48-7.40 (1H, m), 3.04 (3H, s).

Example 16

2-(4-phenylpiperazin-1-yl)-N-[3-(quinoxalin-2-yl)phenyl]acetamide

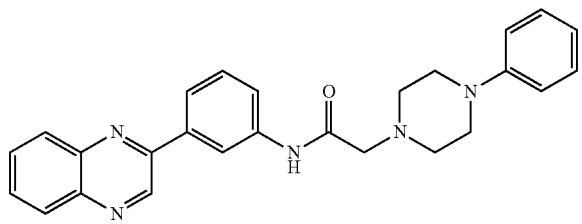 [SMILES: O=C(CN1CCN(c2ccccc2)CC1)Nc1cccc(-c2cnc3ccccc3n2)c1]

A slurry of 2-chloro-N-(3-quinoxalin-2-ylphenyl)acetamide (1.64 g, 5.5 mmol), $K_2CO_3$ (0.92 g, 6.87 mmol), 1-phenylpiperazine (1.05 mL, 5.5 mmol) and a catalytical amount of 18-crown-6 in MeCN (20 mL) was refluxed for 7 hrs, cooled to room temperature, and diluted with water. The resulting solid was filtered, washed with water, and dried to afford 2-(4-phenylpiperazin-1-yl)-N-[3-(quinoxalin-2-yl)phenyl]acetamide (2.1 g, 90% yield). LCMS calculated for $C_{26}H_{25}N_{5}O$ (M+H): 424.52. found 424. $^1$H-NMR (DMSO-d6, 250 Mhz) $\delta_H$: 10.5 (1H, br. s), 9.52 (1H, s), 8.58 (1H, br. s), 8.20-7.80 (6H, m), 7.55 (1H, m), 7.25-7.15 (2H, m), 6.98-6.90 (2H, m), 6.80-6.72 (1H, m), 3.28-3.25 (6H, m), 2.75-2.65 (4H, m).

Example 17

2-(4-methylpiperazin-1-yl)-N-[3-(quinoxalin-2-yl)phenyl]acetamide

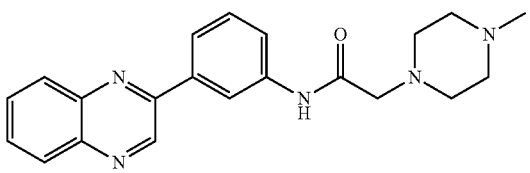 [SMILES: CN1CCN(CC(=O)Nc2cccc(-c3cnc4ccccc4n3)c2)CC1]

A solution of 2-chloro-N-(3-quinoxalin-2-ylphenyl)acetamide (100 mg, 0.336 mmol) and N-methylpiperazine (79 µL, 0.706 mmol) in ethanol (5 mL) was heated at 100° C. for 18 hrs. The solvent was evaporated and the oily residue was submitted to preparative LCMS to afford 2-(4-methylpiperazin-1-yl)-N-[3-(quinoxalin-2-yl)phenyl]acetamide (42 mg, 34%). LCMS calculated for $C_{21}H_{23}N_{5}O$ (M+H): 362.19. found 362.16. $^1$H-NMR (DMSO-d6, 400 Mhz) $\delta_H$: 9.90 (1H, br. s), 9.51 (1H, s), 8.54 (1H, m), 8.19-8.12 (2H, m), 8.08 (1H, d, J=7 Hz), 7.94-7.82 (3H, m), 7.55 (1H, m), 3.18 (2H, s), 2.60-2.53 (4H, br), 2.48-2.40 (4H, br), 2.20 (3H, s).

Example 18

2,2-dichloro-N-[3-(quinoxalin-2-yl)phenyl]acetamide

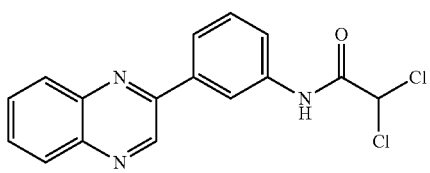 [SMILES: O=C(Nc1cccc(-c2cnc3ccccc3n2)c1)C(Cl)Cl]

To a solution of (3-quinoxalin-2-ylphenyl)amine (135 mg, 0.610 mmol) and diisopropylethylamine (DIEA, 121 µL, 0.732 mmol) in THF (5 mL), dichloroacetyl chloride (65 µL, 0.673 mmol) was added at room temperature. The reaction mixture was stirred at room temperature for 24 hrs and then diluted with ethyl acetate (25 mL). The organic phase was washed with water (25 mL) and then brine (25 mL), dried over $MgSO_4$, and the solvent was evaporated in vacuo to afford 2,2-dichloro-N-[3-(quinoxalin-2-yl)phenyl]acetamide (82 mg, 40% yield). LCMS calculated for $C_{16}H_{11}Cl_2N_3O$ (M+H): 332.03. found 332.09. $^1$H-NMR (DMSO-d6, 400, Mhz) $\delta_H$: 10.60 (1H, br. s), 9.55 (1H, s), 8.53 (1H, s), 8.18-8.05 (3H, m), 7.95-7.85 (3H, m), 7.62 (1H, m), 6.65 (1H, s).

Example 19

3-chloro-N-[3-(quinoxalin-2-yl)phenyl]propanamide

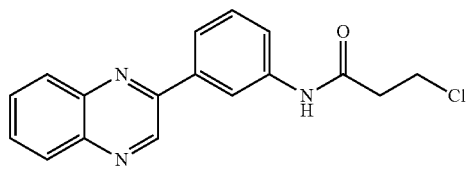 [SMILES: O=C(CCCl)Nc1cccc(-c2cnc3ccccc3n2)c1]

To a solution of (3-quinoxalin-2-ylphenyl)amine (128 mg, 0.578 mmol) and DIEA (115 µL, 0.694 mmol) in THF (5 mL), dichloroacetyl chloride (61 µL, 0.636 mmol) was added at room temperature. The reaction mixture was stirred at room temperature for 48 hrs, diluted with ethyl acetate (20 mL). The organic phase was washed with water (10 mL) and then brine (10 mL), dried over $MgSO_4$, and the solvent was evaporated in vacuo to afford a light-yellow solid. The solid was triturated with $Et_2O$, filtered, and submitted to preparative LCMS to afford 3-chloro-N-[3-(quinoxalin-2-yl)phenyl]propanamide (50 mg, 28% yield). LCMS calculated for $C_{17}H_{14}ClN_3O$ (M+H): 312.08. found 312.14. $^1$H-NMR (DMSO-d6, 400 Mhz) $\delta_H$: 10.30 (1H, br. s), 9.50 (1H, s), 8.52 (1H, m), 6.65-8.60 (2H, m), 8.58 (1H, d, J=7 Hz), 7.95-7.84 (3H, m), 7.55 (1H, m), 3.91 (2H, t, J=7.1 Hz), 2.88 (2H, t, J=7.1 Hz).

Example 20

2-morpholino-N-(3-(quinoxalin-2-yl)phenyl)acetamide

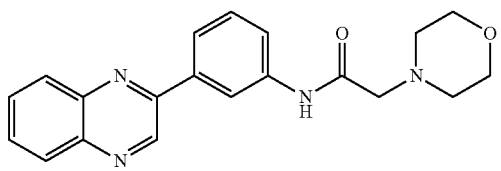 [SMILES: O=C(CN1CCOCC1)Nc1cccc(-c2cnc3ccccc3n2)c1]

To a solution of 2-chloro-N-(3-quinoxalin-2-ylphenyl)acetamide (100 mg, 0.336 mmol) in EtOH (5 mL), morpholine (63 µL, 0.706 mmol) was added and the reaction mixture was heated at 100° C. for 20 hrs. Upon completion, the solvent was removed in vacuo and the crude oily residue was purified by preparative LCMS to afford 2-morpholino-N-(3-(quinoxalin-2-yl)phenyl)acetamide (35 mg, 30% yield). LCMS calculated for C$_{20}$H$_{20}$N$_4$O2 (M+H): 349.40. found 349. $^1$H-NMR (DMSO-d6, 400 Mhz) δ$_H$: 9.98 (1H, br.), 9.53 (1H, s), 8.55 (1H, m), 8.13-8.20 (2H, m), 8.05-8.08 (1H, m), 7.82-7.98 (3H, m), 7.55-7.60 (1H, m), 3.70 (4H, m), 3.20 (2H, s), 2.58 (4H, m).

Example 21

2-chloro-N-(3-(quinoxalin-2-yl)phenyl)propanamide

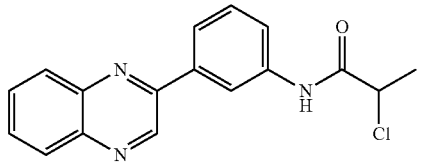 [SMILES: CC(Cl)C(=O)Nc1cccc(-c2cnc3ccccc3n2)c1]

To a solution of (3-quinoxalin-2-ylphenyl)amine (124 mg, 0.560 mmol) and diisopropylethylamine (DIEA, 111 μL, 0.672 mmol) in THF (5 mL), 2-chloropropionyl chloride (60 μL, 0.620 mmol) was added at room temperature. The reaction mixture was stirred at room temperature for 24 hrs and then diluted with ethyl acetate (20 mL). The organic phase was washed with water (20 mL), dried over MgSO$_4$ and the solvent was evaporated in vacuo to afford 2-chloro-N-(3-(quinoxalin-2-yl)phenyl)propanamide (92 mg, 52% yield). LCMS calculated for C$_{17}$H$_{14}$ClN$_3$O (M+H): 312.77. found 313. $^1$H-NMR (DMSO-d6, 400 Mhz) δ$_H$: 10.52 (1H, br.), 9.53 (1H, s), 8.55 m), 8.12-8.18 (2H, m), 8.05-8.08 (1H, m), 7.82-7.95 (3H, m), 7.55-7.60 (1H, m), 4.75 (1H, q, J=6.8 Hz), 1.68 (3H, d, J=6.8 Hz).

Example 22

N-(3-(quinoxalin-2-yl)phenyl)acrylamide

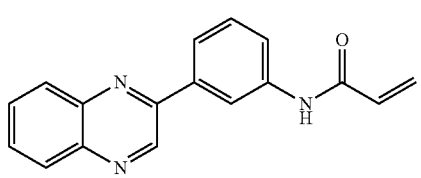 [SMILES: C=CC(=O)Nc1cccc(-c2cnc3ccccc3n2)c1]

To a solution of (3-quinoxalin-2-ylphenyl)amine (100 mg, 0.452 mmol) and diisopropylethylamine (DIEA, 90 μL, 0.542 mmol) in THF (5 mL), acryloyl chloride (41 μL, 0.497 mmol) was added at room temperature and the reaction mixture was stirred for 24 hrs. Upon diluted with ethyl acetate (25 mL), the organic phase was washed with water (25 mL), dried over MgSO$_4$, filtered and the solvent evaporated in vacuo to afford N-(3-(quinoxalin-2-yl)phenyl)acrylamide (109 mg, 87% yield). LCMS calculated for C$_{17}$H$_{13}$N$_3$O (M+H): 276.31. found 276.17. $^1$H-NMR (DMSO-d6, 400 Mhz) δ$_H$: 10.49 (1H, br.), 9.52 (1H, s), 8.60 (1H, m), 8.13-8.16 (2H, m), 8.05-8.08 (1H, m), 7.80-7.95 (3H, m), 7.55-7.60 (1H, m), 6.48-6.58 (1H, dd, J=10 Hz and 16.5 Hz), 6.32 (1H, d, J=16.5 Hz), 5.80 (1H, d, J=10 Hz).

Example 23

N-(3-(quinoxalin-2-yl)phenyl)but-3-enamide

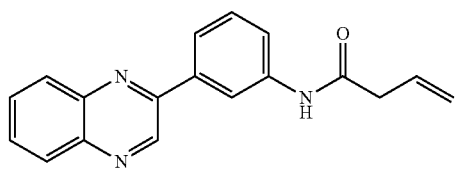 [SMILES: C=CCC(=O)Nc1cccc(-c2cnc3ccccc3n2)c1]

To a solution of vinylacetic acid (43 μL, 0.497 mmol) and oxalyl chloride (48 μL, 0.542 mmol) in DCM (5 mL), a drop of DMF was added using a Pasteur pipette. The colourless solution was stirred at room temperature for 15 min, and a solution of (3-quinoxalin-2-ylphenyl)amine (100 mg, 0.452 mmol) and diisopropylethylamine (DIEA, 90 μL, 0.542 mmol) in THF (5 mL) was added. The resulting slurry was stirred at room temperature for 24 hrs, the reaction mixture was then diluted with ethyl acetate (30 mL) and washed with water (2×25 mL), the organic phase dried over sodium sulphate and the solvent evaporated in vacuo. The resulting crude solid was purified by preparative LCMS to afford N-(3-(quinoxalin-2-yl)phenyl)but-3-enamide (35 mg, 22% yield). LCMS calculated for C$_{18}$H$_{15}$N$_3$O (M+H): 290.33. found 290.24. $^1$H-NMR (DMSO-d6, 400 Mhz) δ$_H$: 10.59 (1H, br.), 9.52 (1H, s), 8.52 (1H, m), 8.12-8.16 (2H, m), 8.05-8.08 (1H, m), 7.80-7.95 (3H, m), 7.55-7.60 (1H, m), 5.95-6.07 (1H, m), 5.25-5.12 (2H, m), 3.18 (2H, d, J=6.2 Hz).

Example 24

2-bromo-N-(3-(quinoxalin-2-yl)phenyl)acetamide

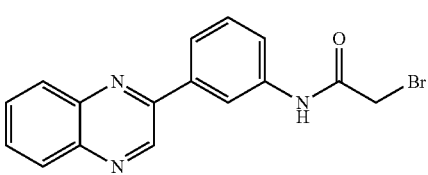 [SMILES: O=C(CBr)Nc1cccc(-c2cnc3ccccc3n2)c1]

To a solution of (3-quinoxalin-2-ylphenyl)amine (2 g, 9.04 mmol) in THF (50 mL), bromoacetyl bromide (0.83 mL, 9.5 mmol) was added, followed by diisopropylethylamine (DIEA, 1.8 mL, 10.85 mmol), at room temperature. The reaction mixture was stirred at room temperature for 24 hrs, the slurry was diluted with ethyl acetate and the organic phase was washed with water (50 mL). The insoluble solid was filtered and analysed to afford 2-bromo-N-(3-(quinoxalin-2-yl)phenyl)acetamide (700 mg, 22% yield). The mother liquer was evaporated in vacuo to afford a second batch of 2-bromo-N-(3-(quinoxalin-2-yl)phenyl)acetamide (1.8 g, 58% yield). LCMS calculated for C$_{18}$H$_{15}$N$_3$O (M+H): 290.33. found 290.24. $^1$H-NMR (DMSO-d6, 400 Mhz) δ$_H$: 10.62 (1H, br.), 9.52 (1H, s), 8.55 (1H, m), 8.12-8.18 (2H, m), 8.05-8.08 (1H, m), 7.80-7.95 (3H, m), 7.55-7.60 (1H, m), 4.12 (2H, s).

Example 25

2-(methylthio)-N-(3-(quinoxalin-2-yl)phenyl)acetamide

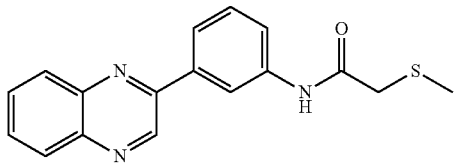

A slurry of 2-bromo-N-(3-(quinoxalin-2-yl)phenyl)acetamide (207 mg, 0.605 mmol) and sodium thiomethoxide (127 mg, 1.82 mmol) in ethanol (10 mL) was stirred at room temperature for 18 hrs. The reaction mixture was diluted with water (10 mL) and ethyl acetate (50 mL), the organic phase was separated, dried over sodium sulphate and evaporated in vacuo to afford 2-(methylthio)-N-(3-(quinoxalin-2-yl)phenyl)acetamide (140 mg, 75% yield). LCMS calculated for $C_{17}H_{15}N_3OS$ (M+H): 310.39. found 310. $^1$H-NMR (DMSO-d6, 400 Mhz) $\delta_H$: 10.30 (1H, br.), 9.53 (1H, s), 8.53 (1H, m), 8.12-8.18 (2H, m), 8.05-8.08 (1H, m), 7.84-7.95 (3H, m), 7.55-7.60 (1H, m), 3.35 (2H, s), 2.22 (3H, s).

Example 26

4,4,4-trifluoro-3-oxo-N-(3-(quinoxalin-2-yl)phenyl)butanamide

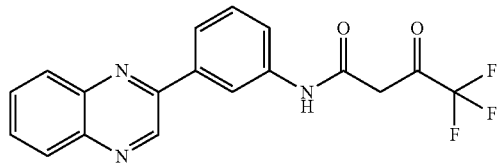 [SMILES: O=C(CC(=O)C(F)(F)F)Nc1cccc(-c2cnc3ccccc3n2)c1]

A mixture of 3-quinoxalin-2-ylphenyl)amine (200 mg, 0.904 mmol) and ethyl 4,4,4-trifluoroacetoacetate (140 µL, 0.95 mmol) in dry toluene (10 mL) was heated at reflux for 4 hrs. A light yellow precipitate resulted on cooling. The solid was filtered, washed with cold diethyl ether and dried to afford 4,4,4-trifluoro-3-oxo-N-(3-(quinoxalin-2-yl)phenyl)butanamide (21 mg, 6% yield). LCMS calculated for $C_{18}H_{12}F_3N_3O_2$ (M+H): 360.30. found 360 (2 peaks with the same m/e due to tautomers). $^1$H-NMR (DMSO-d6, 400 Mhz) $\delta_H$: 10.42 (1H, br.), 9.52 (1H, s), 8.55 (1H, m), 8.15-8.20 (2H, m), 8.08-8.12 (1H, m), 7.82-7.95 (3H, m), 7.55-7.60 (1H, m), 2.88 (2H, s).

Example 27

2-oxo-2-(3-(quinoxalin-2-yl)phenylamino)ethyl methanesulfonate

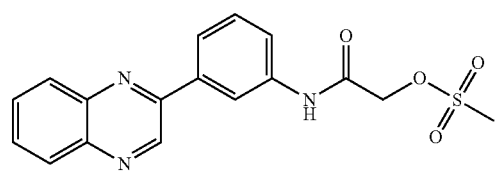 [SMILES: CS(=O)(=O)OCC(=O)Nc1cccc(-c2cnc3ccccc3n2)c1]

A slurry of 2-bromo-N-(3-(quinoxalin-2-yl)phenyl)acetamide (165 mg, 0.482 mmol) and silver methanesulphonate (250 mg, 1.23 mmol) in acetonitrile (5 mL) was heated at reflux for 20 hrs. The resulting purple solution was diluted with DCM (5 mL) and the solvent evaporated in vacuo. The residue was triturated with ethyl acetate (5×10 mL) and the collected volumes of solvent were filtered through a small plug of silica (Isolute Si 2 g), further eluted with ethyl acetate (50 mL) and the solvent evaporated in vacuo to afford 2-oxo-2-(3-(quinoxalin-2-yl)phenylamino)ethyl methanesulfonate (8 mg, 5% yield). LCMS calculated for $C_{17}H_{15}N_3O_4S$ (M+H): 358.39. found 358. $^1$H-NMR (DMSO-d6, 400 Mhz) $\delta_H$: 10.4 (br., 1H), 9.53 (s, 1H), 8.54 (s, 1H), 8.10-8.20 (m, 3H), 7.85-7.95 (m, 3H), 7.55-7.62 (m, 1H), 4.96 (s, 2H), 3.35 (s, 3H).

Example 28

2-oxo-2-(3-(quinoxalin-2-yl)phenylamino)ethyl acetate

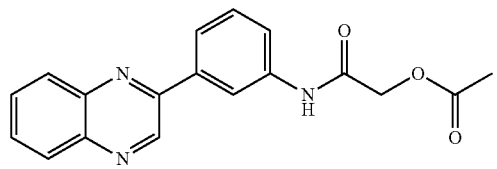

A solution of 2-bromo-N-(3-(quinoxalin-2-yl)phenyl)acetamide (100 mg, 0.292 mmol) and sodium acetate (159 mg, 1.168 mmol) in acetonitrile (5 mL) was heated in microwave at 140° C. for 7.5 min. The dark-yellow solution was diluted with ethyl acetate (25 mL), washed with water (20 mL), dried over sodium sulphate and the solvent evaporated to afford 2-oxo-2-(3-(quinoxalin-2-yl)phenylamino)ethyl acetate (70 mg, 74% yield). LCMS calculated for $C_{18}H_{15}N_3O_3$ (M+H): 322.33. found 322. $^1$H-NMR (DMSO-d6, 400 Mhz) $\delta_H$: 10.3 (1H, br.), 9.51 (1H, s), 8.52 (1H, m), 8.15-8.20 (2H, m), 8.08-8.10 (1H, m), 7.82-8.00 (3H, m), 7.55-7.60 (1H, m), 4.70 (2H, s), 2.15 (3H, s).

Example 29

2-hydroxy-N-(3-(quinoxalin-2-yl)phenyl)acetamide

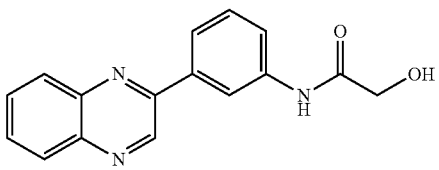 [SMILES: O=C(CO)Nc1cccc(-c2cnc3ccccc3n2)c1]

To a solution of (3-quinoxalin-2-ylphenyl)amine (200 mg, 0.904 mol) and glycolic acid (83 mg, 1.085 mmol) in dry DMF (6 mL), EDC (191 mg, 1 mmol) and HOBt hydrate (154 mg, 1 mmol) were added and the reaction mixture was heated at 60° C. for 18 hrs. The solvent was evaporated in vacuo (45° C., 0.1 mbar) and the residue was dissolved in ethyl acetate (50 mL) and washed with water (2×25 mL). The organic phase was washed dried over sodium sulphate, filtered, the solvent evaporated in vacuo, the residue was triturated with DCM and further purified by preparative LCMS to afford 2-hydroxy-N-(3-(quinoxalin-2-yl)phenyl)acetamide (60 mg, 23% yield). LCMS calculated for $C_{16}H_{13}N_3O_2$ (M+H): 280.29. found 280. ¹H-NMR (DMSO-d6, 400 Mhz) $\delta_H$: 10.38 (1H, br.), 9.52 (1H, s), 8.62 (1H, m), 8.14-8.20 (2H, m), 8.05-8.08 (1H, m), 7.80-7.95 (3H, m), 7.55-7.60 (1H, m), 5.64 (1H, br), 4.08 (2H, s).

Example 30

S-2-oxo-2-(3-(quinoxalin-2-yl)phenylamino)ethyl ethanethioate

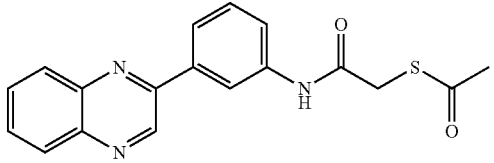

A mixture of 2-bromo-N-(3-(quinoxalin-2-yl)phenyl)acetamide (300 mg, 0.876 mmol) and potassium thioacetate (400 mg, 3.5 mmol) in acetonitrile (15 mL) was heated in microwave at 140° C. for 10 min. The dark red solution was diluted with ethylacetate (50 mL), washed with brine (2×50 mL), dried over sodium sulphate, the solvent was evaporated in vacuo and the residue was purified by flash column chromatography (Flash Master, 20 g Isolute Silica column, gradient 0 to 5 min hexane, then ethyl acetate up to 50% over 20 min) to afford S-2-oxo-2-(3-(quinoxalin-2-yl)phenylamino) ethyl ethanethioate (40 mg, 13% yield). LCMS calculated for $C_{18}H_{15}N_3O_2S$ (M+H): 338.40. found 338. ¹H-NMR (DMSO-d6, 400 Mhz) $\delta_H$: 10.45 (1H, br.), 9.50 (1H, s), 8.51 (1H, m), 8.11-8.18 (2H, m), 8.05-8.08 (1H, m), 7.80-7.95 (3H, m), 7.55-7.60 (1H, m), 3.90 (2H, s), 2.41 (3H, s).

Example 31

(E/Z)-3-(1-(3-(quinoxalin-2-yl)phenylamino)ethylidene)dihydrofuran-2(3H)-one

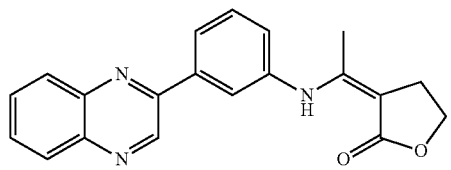 [SMILES: C/C(Nc1cccc(-c2cnc3ccccc3n2)c1)=C1\CCOC1=O]

A mixture of (3-quinoxalin-2-ylphenyl)amine (300 mg, 1.36 mmol) and □-acetyl-□-butyrolactone (175 mg, 1.36 mmol) in ethanol (5 mL) was refluxed for 2 days. LCMS analysis showed produce and unreacted starting material. An additional amount of □-acetyl-□-butyrolactone (175 mg, 1.36 mmol) was added and the reaction mixture was refluxed for further 3 days. A precipitate resulted on cooling. This was filtered, washed with ethanol (10 mL), triturated with diethyl ether (10 mL), filtered and dried to afford (E/Z)-3-(1-(3-(quinoxalin-2-yl)phenylamino)ethylidene)dihydrofuran-2 (3H)-one (266 mg, 56% yield). LCMS calculated for $C_{20}H_{17}N_3O_2$ (M+H): 332.37. found 332. ¹H-NMR (DMSO-d6, 400 Mhz) $\delta_H$: 10.03 (1H, br.), 9.60 (1H, s), 8.08-8.20 (4H, m), 7.85-7.92 (2H, m), 7.60 (1H, m), 7.48 (1H, m), 4.32 (2H, t, J=7 Hz), 2.62 (2H, t, J=7 Hz), 2.14 (3H, s).

Example 32 ethyl 3-oxo-3-(3-(quinoxalin-2-yl)phenylamino)propanoate

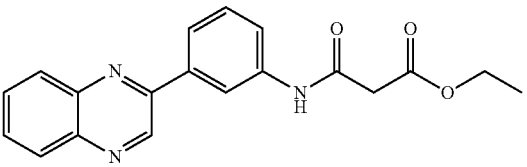 [SMILES: CCOC(=O)CC(=O)Nc1cccc(-c2cnc3ccccc3n2)c1]

A slurry of (3-quinoxalin-2-ylphenyl)amine (200 mg, 0.904 mmol) and diethyl malonate (1.4 mL, 9.04 mmol) was heated at 160° C. in a Dean-Stark vial (Glass Solutions) for 5 hrs. The reaction mixture was diluted with ethyl acetate (25 mL), the organic phase was washed with water (20 mL) and brine (20 mL), dried over sodium sulphate, the solvent evaporated in vacuo and the residue dissolved in DCM (2 mL). The solution was loaded on a Isolute 20 g silica gel column and purified by flash chromatography (Flash Master, 5 g Isolute Silica column, gradient 0 to 5 min hexane, then ethyl acetate up to 50% over 20 min) to afford ethyl 3-oxo-3-(3-(quinoxalin-2-yl)phenylamino)propanoate (60 mg, 20% yield). LCMS calculated for $C_{19}H_{17}N_3O_3$ (M+H): 336.35. found 336. ¹H-NMR (DMSO-d6, 400 Mhz) $\delta_H$: 10.41 (1H, br.), 9.52 (1H, s), 8.52 (1H, m), 8.15-8.10 (2H, m), 8.05-8.08 (1H, m), 7.82-7.95 (3H, m), 7.55-7.60 (1H, m), 4.16 (2H, q, J=8 Hz), 3.54 (2H, s), 1.23 (3H, t, J=8 Hz).

Example 33

2-(4-(pyridin-4-yl)piperazin-1-yl)-N-(3-(quinoxalin-2-yl)phenyl)acetamide

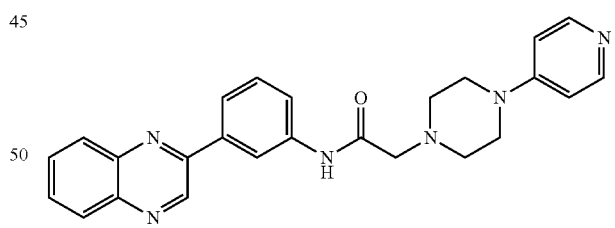

A mixture of 2-bromo-N-(3-(quinoxalin-2-yl)phenyl)acetamide (100 mg, 0.292 mmol), potassium carbonate (51 mg, 0.365 mmol) and 1-(4-pyridyl)-piperazine (50 mg, 0.307 mmol) in acetonitrile (5 mL) was heated at reflux for 15 min. The solvent was evaporated in vacuo and the crude reaction mixture was purified by preparative LCMS to afford 2-(4-(pyridin-4-yl)piperazin-1-yl)-N-(3-(quinoxalin-2-yl)phenyl) acetamide (30 mg, 24% yield). LCMS calculated for $C_{25}H_{24}N_6O$ (M+H): 425.50. found 425.44. ¹H-NMR (DMSO-d6, 400 Mhz) $\delta_H$: 10.04 (1H, br.), 9.52 (1H, s), 8.58 (1H, m), 8.15-8.10 (4H, m), 8.05-8.08 (1H, m), 7.82-7.95 (3H, m), 7.55-7.60 (1H, m), 6.85 (2H, m), 3.45 (4H, m), 3.25 (2H, s), 2.72 (4H, m).

Example 34

2-(4-hydroxypiperidin-1-yl)-N-(3-(quinoxalin-2-yl)phenyl)acetamide

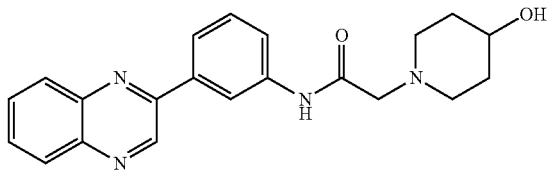 [SMILES: O=C(CN1CCC(O)CC1)Nc1cccc(-c2cnc3ccccc3n2)c1]

A mixture of 2-bromo-N-(3-(quinoxalin-2-yl)phenyl)acetamide (93 mg, 0.272 mmol) and 4-hydroxypiperidine (138 mg, 1.35 mmol) in isopropanol (5 mL) was heated at reflux for 1 h. The solvent was evaporated in vacuo and the crude reaction mixture was purified by preparative LCMS to afford 2-(4-hydroxypiperidin-1-yl)-N-(3-(quinoxalin-2-yl)phenyl)acetamide (26 mg, 26% yield). LCMS calculated for $C_{21}H_{22}N_4O_2$ (M+H): 363.43. found 363.40. $^1$H-NMR (CD$_3$CN, 400 Mhz) $\delta_H$: 9.55 (1H, br.), 9.25 (1H, s), 8.40 (1H, m), 8.00-8.05 (2H, m), 7.85-7.90 (1H, m), 7.65-7.80 (3H, m), 7.40-7.48 (1H, m), 3.65 (1H, m), 3.22 (2H, s), 2.85-3.15 (OH and 2H, br. and m), 2.40-2.50 (2H, m), 1.82-1.92 (2H, m), 1.55-1.68 (2H, m).

Example 35

2-(piperazin-1-yl)-N-(3-(quinoxalin-2-yl)phenyl)acetamide

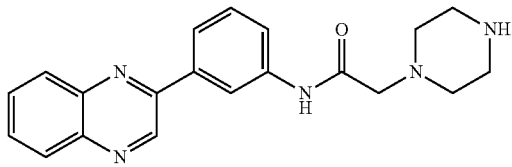 [SMILES: O=C(CN1CCNCC1)Nc1cccc(-c2cnc3ccccc3n2)c1]

A slurry of 2-chloro-N-(3-quinoxalin-2-ylphenyl)acetamide (100 mg, 0.336 mmol) and piperazine (58 mg, 0.672 mmol) in MeCN (5 mL) was heated at reflux for 48 hrs. The resulting precipitate was filtrated, washed with MeCN (10 mL) and submitted to preparative LCMS to afford 2-(piperazin-1-yl)-N-(3-(quinoxalin-2-yl)phenyl)acetamide (46 mg, 39% yield). LCMS calculated for $C_{20}H_{21}N_5O$ (M+H): 348.42. found 348. $^1$H-NMR (DMSO-d6, 400 Mhz) $\delta_H$: 9.92 (1H, br.), 9.52 (1H, s), 8.55 (1H, m), 8.13-8.20 (2H, m), 8.05-8.08 (1H, m), 7.82-7.98 (3H, m), 7.55-7.60 (1H, m), 3.25-3.40 (NH and 6H, br.), 2.80-2.88 (4H, br.).

Example 36

3-(aminosulfonyl)-N-[3-(2-quinoxalinyl)phenyl]propanamide

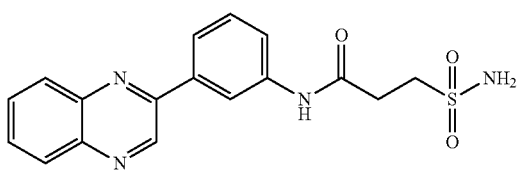 [SMILES: NS(=O)(=O)CCC(=O)Nc1cccc(-c2cnc3ccccc3n2)c1]

To a solution of (3-quinoxalin-2-ylphenyl)amine (120 mg, 0.545 mol) and 3-sulfamoylpropanoic acid (100 mg, 0.654 mmol) in dry DMF (3 mL), EDC (115 mg, 0.6 mmol) and HOBt hydrate (92 mg, 0.6 mmol) were added and the reaction mixture stirred at room temperature for 24 hrs. The solvent was evaporated in vacuo (45° C., 0.1 mbar) and the residue was triturated with DCM (10 mL) and filtered. The solid was triturated with hot acetonitrile, filtered hot and dried to afford 3-(aminosulfonyl)-N-[3-(2-quinoxalinyl)phenyl]propanamide (78 mg, 40%). LCMS calculated for $C_{17}H_{16}N_4O_3S$ (M+H): 357.41. found 357.24. $^1$H-NMR (DMSO-d6, 400 Mhz) $\delta_H$: 10.41 (1H, br.), 9.50 (1H, s), 8.53 (1H, m), 8.15 (2H, m), 8.02 (1H, m), 7.94-7.80 (3H, m), 7.55 (1H, m), 6.88 (2H, br.), 3.35 (2H, t, J=7.2 Hz), 2.85 (2H, t, J=7.2 Hz).

Example AA

In Vitro JAK Kinase Enzymatic Assay

The JAK3 kinase is recombinant human protein (catalytic domain, amino acids 781-1124 with GST-tag), expressed in insect cells (Invitrogen Catalog PV3855). The substrate is poly-glutamic acid-tyrosin peptide, Poly-(GT) (4:1) (Sigma-Aldrich, catalog P7244). [γ-$^{33}$P]-ATP is purchased from Perkin Elmer (catalog NEG602H001MC) (EasyTides). Kinase reaction buffer is 100 mM HEPES (pH 7.5), 20 mM MgCl$_2$, 2 mM EGTA, 0.02% Brij 35. The JAK1 (Invitrogen Catalog PV4774), JAK2 (Invitrogen Catalog PV4210) and TYK2 Invitrogen Catalog PV4790) enzymatic assays are performed in the similar way. JAK1 and JAK2 substrate is Poly-(GT) (4:1), but TYK2 substrate is peptide with sequences of KKSRGDYMTMQIG. The reaction is carried for 2 hours at room temperature. After the reactions are finished or stopped, portion or all the reaction mixtures are transferred onto filter paper P81 Phosphocellulose paper (Whatman catalog 3698-915) for binding the final radioisotope labeled products. The unreacted phosphate are washed away without interfering with the detection of real phosphorylated products. The final product can be detected by instruments such as scintillation counter, top counter or phosphoimager. The enzymatic assays can also performed in assays described those described in the art [e.g., Ma H et al, Expert Opin. Drug Discov. 3, 607-621 (2008); Olive D M, Expert Rev Proteomics, 1, 327-341 (2004)].

The IC$_{50}$ values (the concentrations needed to reach 50% inhibition), were determined by fitting the assay signal to the following equation using Graphpad Prizm.

Signal=Bottom+(Top−Bottom)/(1+10^((Log(IC50)−Log[I])*Hill Slope) Bottom and Top refer to the post and pre-transition baselines, respectively.

The IC$_{50}$ values for certain example compounds of invention with respect to JAK3 and other JAK family enzymes are provided in Table 1 as follows.

TABLE 1

| Example Number | Structure | JAK3 IC$_{50}$ | JAK2 IC$_{50}$ | JAK1 IC$_{50}$ | TYK2 IC$_{50}$ |
|---|---|---|---|---|---|
| Example 1 | 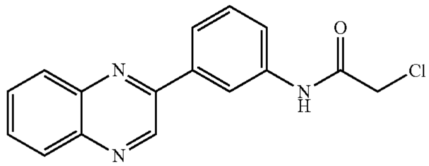 [SMILES: O=C(CCl)Nc1cccc(-c2cnc3ccccc3n2)c1] | 0.2 nM | >20 μM | >20 μM | >20 μM |
| Example 2 | 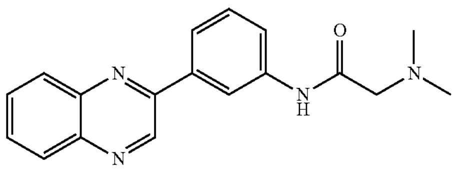 [SMILES: CN(C)CC(=O)Nc1cccc(-c2cnc3ccccc3n2)c1] | >50 μM | >50 μM | >50 μM | >50 μM |
| Example 3 | 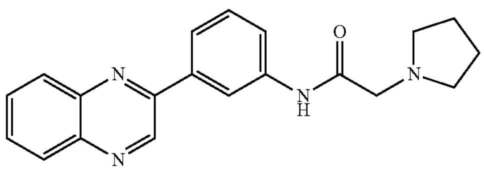 [SMILES: O=C(CN1CCCC1)Nc1cccc(-c2cnc3ccccc3n2)c1] | >20 μM | >20 μM | >20 μM | >20 μM |
| Example 4 | 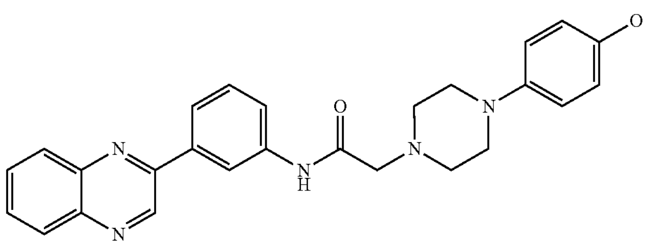 [SMILES: O=C(CN1CCN(c2ccc(O)cc2)CC1)Nc1cccc(-c2cnc3ccccc3n2)c1] | 2.7 μM | >20 μM | >20 μM | >20 μM |
| Example 5 | 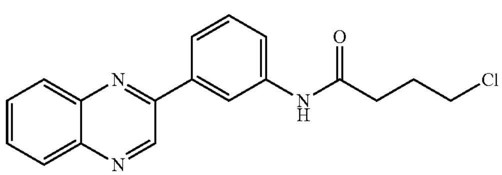 [SMILES: O=C(CCCCl)Nc1cccc(-c2cnc3ccccc3n2)c1] | >50 μM | >50 μM | >50 μM | >50 μM |
| Example 6 | 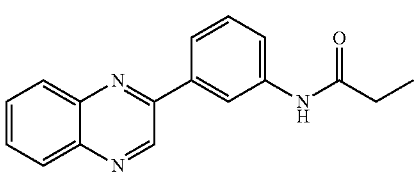 [SMILES: CCC(=O)Nc1cccc(-c2cnc3ccccc3n2)c1] | >50 μM | >50 μM | >50 μM | >50 μM |
| Example 7 | 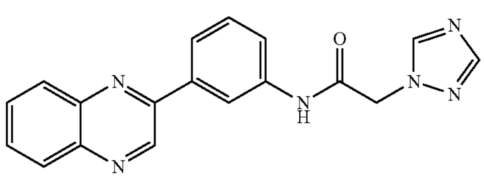 [SMILES: O=C(Cn1cncn1)Nc1cccc(-c2cnc3ccccc3n2)c1] | >50 μM | >50 μM | >50 μM | >50 μM |
| Example 8 | 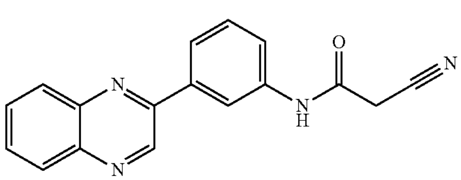 [SMILES: N#CCC(=O)Nc1cccc(-c2cnc3ccccc3n2)c1] | 136 nM | 18.1 μM | >20 μM | >20 μM |

TABLE 1-continued

| Example Number | Structure | JAK3 IC$_{50}$ | JAK2 IC$_{50}$ | JAK1 IC$_{50}$ | TYK2 IC$_{50}$ |
| --- | --- | --- | --- | --- | --- |
| Example 9 | 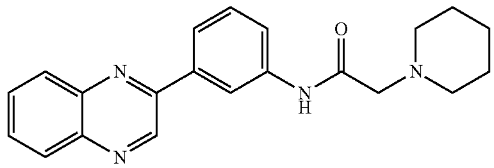 [SMILES: O=C(CN1CCCCC1)Nc1cccc(-c2cnc3ccccc3n2)c1] | 175 nM | >20 μM | >20 μM | >20 μM |
| Example 10 | 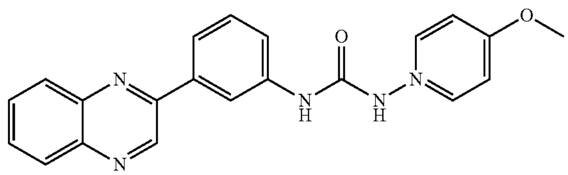 | >50 μM | >50 μM | >50 μM | >50 μM |
| Example 11 | 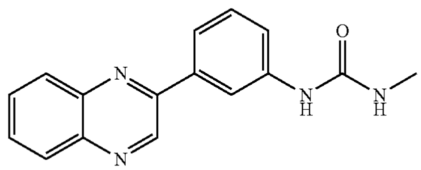 [SMILES: CNC(=O)Nc1cccc(-c2cnc3ccccc3n2)c1] | >50 μM | 25.5 μM | >50 μM | >50 μM |
| Example 12 | 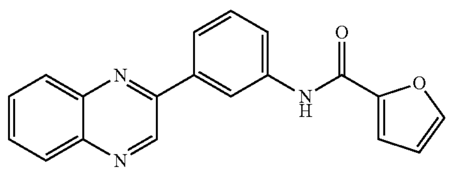 [SMILES: O=C(Nc1cccc(-c2cnc3ccccc3n2)c1)c1ccco1] | >50 μM | 24.58 μM | >50 μM | >50 μM |
| Example 13 | 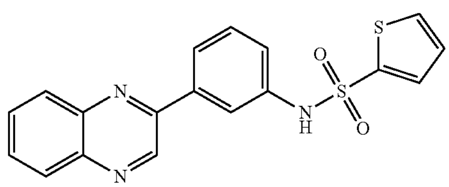 [SMILES: O=S(=O)(Nc1cccc(-c2cnc3ccccc3n2)c1)c1cccs1] | >50 μM | 55.5 μM | >50 μM | >50 μM |
| Example 14 | 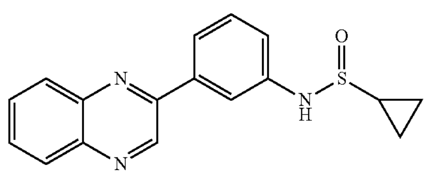 [SMILES: O=S(Nc1cccc(-c2cnc3ccccc3n2)c1)C1CC1] | >50 μM | 25.0 μM | >50 μM | >50 μM |
| Example 15 | 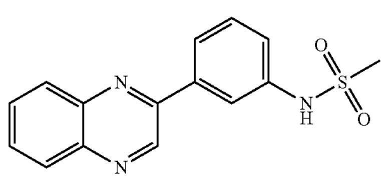 [SMILES: CS(=O)(=O)Nc1cccc(-c2cnc3ccccc3n2)c1] | >50 μM | 18.5 μM | >50 μM | >50 μM |
| Example 16 | 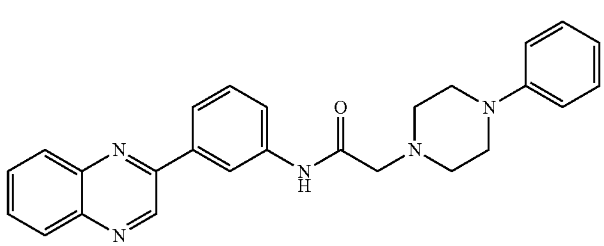 [SMILES: O=C(CN1CCN(c2ccccc2)CC1)Nc1cccc(-c2cnc3ccccc3n2)c1] | 270 nM | 18 μM | >20 μM | >20 μM |

TABLE 1-continued

| Example Number | Structure | JAK3 IC$_{50}$ | JAK2 IC$_{50}$ | JAK1 IC$_{50}$ | TYK2 IC$_{50}$ |
|---|---|---|---|---|---|
| Example 17 | 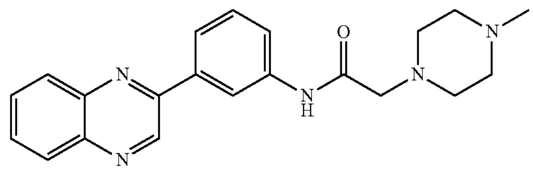 [SMILES: CN1CCN(CC(=O)Nc2cccc(-c3cnc4ccccc4n3)c2)CC1] | >50 μM | >50 μM | >50 μM | >50 μM |
| Example 18 | 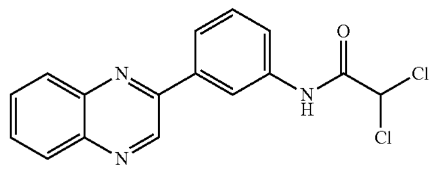 [SMILES: O=C(Nc1cccc(-c2cnc3ccccc3n2)c1)C(Cl)Cl] | 500 nM | >10 μM | >10 μM | >10 μM |
| Example 19 | 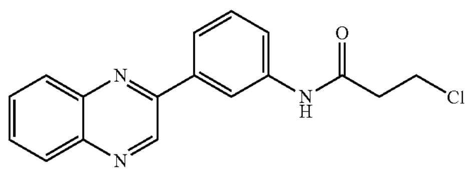 [SMILES: O=C(CCCl)Nc1cccc(-c2cnc3ccccc3n2)c1] | >50 μM | >50 μM | >50 μM | >50 μM |
| Example 20 | 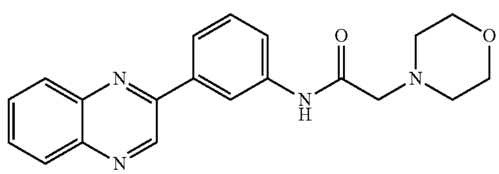 [SMILES: O=C(CN1CCOCC1)Nc1cccc(-c2cnc3ccccc3n2)c1] | 34 μM | >50 μM | >50 μM | >50 μM |
| Example 21 | 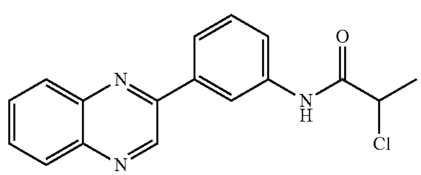 [SMILES: CC(Cl)C(=O)Nc1cccc(-c2cnc3ccccc3n2)c1] | 0.33 μM | >50 μM | >50 μM | >50 μM |
| Example 22 | 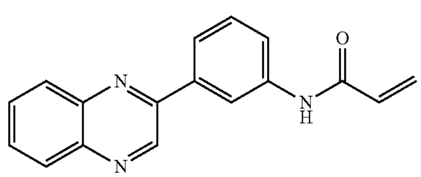 [SMILES: C=CC(=O)Nc1cccc(-c2cnc3ccccc3n2)c1] | 45 nM | >10 μM | >10 μM | >10 μM |
| Example 23 | 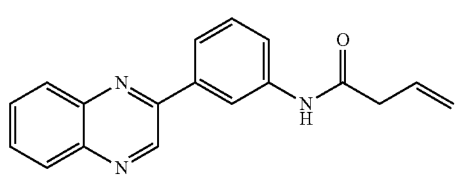 [SMILES: C=CCC(=O)Nc1cccc(-c2cnc3ccccc3n2)c1] | >10 μM | >10 μM | >10 μM | >10 μM |
| Example 24 | 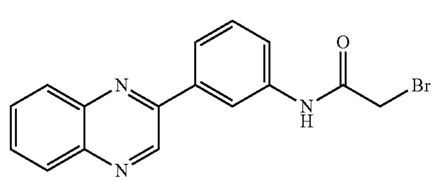 [SMILES: O=C(CBr)Nc1cccc(-c2cnc3ccccc3n2)c1] | 0.3 nM | >10 μM | >10 μM | >10 μM |

TABLE 1-continued
| Example Number | Structure | JAK3 IC$_{50}$ | JAK2 IC$_{50}$ | JAK1 IC$_{50}$ | TYK2 IC$_{50}$ |
|---|---|---|---|---|---|
| Example 25 | 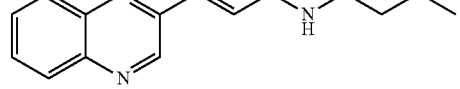 | >10 μM | >10 μM | >10 μM | >10 μM |
| Example 26 | 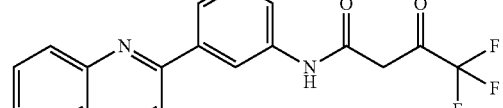 | >10 μM | >10 μM | >10 μM | >10 μM |
| Example 27 | 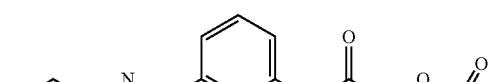 | 0.6 nM | >10 μM | >10 μM | >10 μM |
| Example 28 | 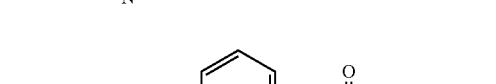 | 150 μM | >10 μM | >10 μM | >10 μM |
| Example 29 | 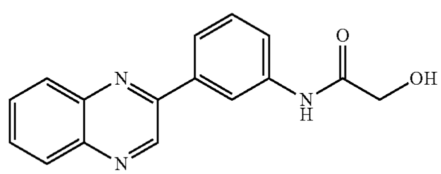 | >10 μM | >10 μM | >10 μM | >10 μM |
| Example 30 | 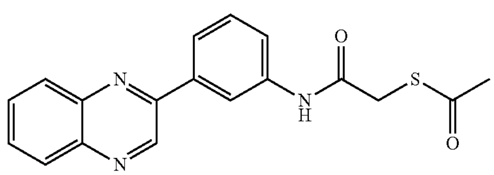 [SMILES: CC(=O)OCC(=O)Nc1cccc(-c2cnc3ccccc3n2)c1] | >10 μM | >10 μM | >10 μM | >10 μM |
| Example 31 | 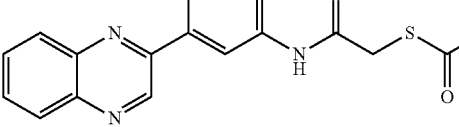 | >10 μM | >10 μM | >10 μM | >10 μM |
| Example 32 | 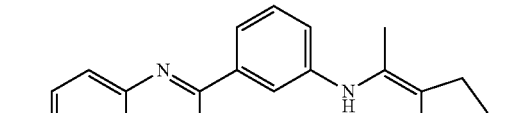 | >10 μM | >10 μM | >10 μM | >10 μM |

TABLE 1-continued

| Example Number | Structure | JAK3 IC$_{50}$ | JAK2 IC$_{50}$ | JAK1 IC$_{50}$ | TYK2 IC$_{50}$a |
|---|---|---|---|---|---|
| Example 33 | 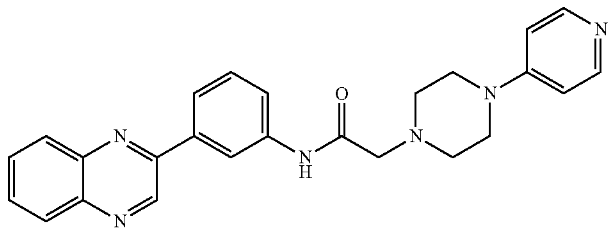 [SMILES: O=C(CN1CCN(c2ccncc2)CC1)Nc1cccc(-c2cnc3ccccc3n2)c1] | >10 μM | >10 μM | >10 μM | >10 μM |
| Example 34 | 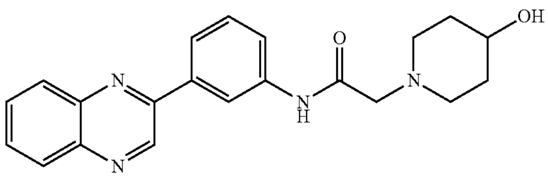 [SMILES: O=C(CN1CCC(O)CC1)Nc1cccc(-c2cnc3ccccc3n2)c1] | >10 μM | >10 μM | >10 μM | >10 μM |
| Example 35 | 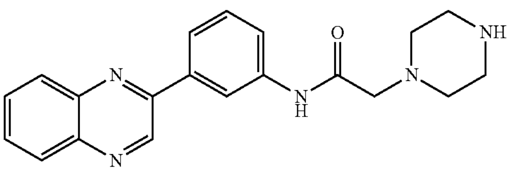 [SMILES: O=C(CN1CCNCC1)Nc1cccc(-c2cnc3ccccc3n2)c1] | 13 μM | >20 μM | >20 μM | >20 μM |
| Example 36 | | >10 μM | >10 μM | >10 μM | >10 μM | a. when the experiment limit is set as "a" and the IC$_{50}$ measurement of the example compound exceeds the limit, then the IC$_{50}$ data is shown as ">a"

Example BB

Inhibition of Human IL-2 Dependent JAK3 Phosphorylation in Cellular Based Assays The screen is measuring the inhibitory effect of compounds on human IL-2 dependent T-cell proliferation and JAK3 phosphorylation in vitro. One or more compounds herein were tested for inhibitory activity of JAK targets according to at least one of the following cellular assays.

Cell lines: The SZ-4 cell line is derived from a Sézary patient (Abrams, et al., 1991, J Investig Dermatol. 96, 31-37), and the growth of this cell line is IL-2 dependent. The cells are grown in RPMI 1640 medium supplemented with 10% fetal calf serum, 2 mM L-glutamine, penicillin 100 U/ml, streptomycin 100 ug/ml, and 10 I.U/ml IL-2 in a 5% CO$_2$ humidified incubator at 37° C.

Cell Proliferation assays: The above cell line is used for determination of cell proliferation activities upon adding compounds with the treatment of IL-2 or other cytokines. Briefly, SZ-4 cells (6×10$^3$/well) are seeded in flat-bottom, 96-well microtiter plates in 200 μL RPMI 1640 media, cells will be starved for 12 hours without IL-2, then will be treated for 72 hr with compounds in the absence or present of 100 I.U/ml IL-2 (Cell Signaling, Beverly, Mass.). Cell proliferation assay were determined by MTT assay. MTT [3-(4,5-dimethylthiazol-2-yl)-2,5-diphenyltetrazolium bromide] assay (Mosmann, T R 1983, J. Immunol. Methods 65, 55-63.), is based on the ability of a mitochondrial dehydrogenase enzyme from viable cells to cleave the tetrazolium rings of the pale yellow MTT and form a dark blue formazan crystals which is largely impermeable to cell membranes, thus resulting in its accumulation within healthy cells. Solubilization of the cells by the addition of a detergent results in the liberation of the crystals which are solubilized. The number of surviving cells is directly proportional to the level of the formazan product created. Reagent Preparation: Dissolve the MTT powder 5 mg/mL in Hank's in brown color tubes to avoid light and store in 4° C. Stop Mix Solution: 20% SDS in 50% dimethylformamide. Assay Protocol: 1) Adding test compounds to the cells. Include replicates for a range of concentrations. Include negative controls (including vehicle control) and a positive control. The final volume will be 100 μL per well. 2) At different testing time points, adding MTT reagent (10 μL/100 μL per well of the 96 well plate) and incubate for 3 hours. 3) Adding 1 volume (100 μL) of the stop mix solution and rock the plate at room temperature for a minimum of 1 hour. (Allows time for the formazan precipitate to dissolve). A purple color should be visible at this stage and should deepen over the 1 hour incubation period. 4) After the 1 hour incubation, ensure the formazan precipitate is dissolved by pipetting each well up and down until not precipitate is visible. 5) Read the plate on a plate reader using 550 nM as test wavelength and 630 nM as the reference wavelength. % Viability=(Mean Absorbance of Sample)/(Mean Absorbance of Control)×100. The data is analyzed by plotting the % inhibition of proliferation verses the concentration of test compound. An IC50 values is determined from the plot. For instance, compound Example 1 is found to have $IC_{50}$ values of 0.3 nM, and compound Example 16 is found to have $IC_{50}$ values of 270 nM.

Protein and phosphorylation detection by immunoprecipitation and Western Blot: the above cells is used to evaluate the compounds activities of inhibiting JAK/STAT phosphorylations. After the cells are treated as described above, cells are collected and pelleted by centrifuging, cell pellets are then lysed with PI/RIPA lysis buffer (1% NP40, 1% Deoxycholic Acid, 0.1% SDS, 0.15M NaCl, 10 mM Sodium Phosphate, 1 mM PMSF, 2 mM EDTA, 10 mM NaF, 10 mM Napyrophosphate, 0.4 mM $Na_3VO_4$, 10 mM Indoacetamide, PH, 8.0) on ice. The lysed cells are centrifuged at 15,000 rpm to remove cell debris, add 5 ul of Anti-Phosphotyrosine, 4G10® Platinum (Upstate Biotechnology, Lake Placid, N.Y.), and incubate for 90 min on ice. Then, the protein A-Sepharose (Invitrogen, Carlsbad, Calif.) is added to precipitate the immune complexes for 1 hr at 4° C. The immunoprecipitates are washed 3× with lysis buffer, and suspended in loading buffer. For Western blot analyses, the immunoprecipitates then are resolved on SDS-PAGE, transferred to nitrocellulose membrane, and probed with Anti-JAK3 and Anti-STATS (Cell Signaling, Beverly, Mass.). In brief, membranes are be blocked in 5% nonfat milk in TBS (pH 7.4) containing 0.1% Tween 20 for 1 h and subsequently probed with primary antibodies at 4° C. overnight. Membranes are probed with horseradish peroxidase-conjugated secondary antibodies (GE Healthcare, Piscataway, N.J.) and then visualized by Enhanced Chemiluminescence Reagent (GE Healthcare, Piscataway, N.J.). For instance, IL-2 can increase the JAK3 phosphorylation level more than 12-fold above background level, with 0.8 μM of compound Example 1 added, the JAK3 phosphorylation level is only increased about 2-fold above background level.

Example CC

Murine Collagen-Induced Arthritis (CIA) Model and Adjuvant-Induced Arthritis (AIA) Model for Evaluating Rheumatoid Arthritis Compounds herein can be tested in murine collagen-induced arthritis (CIA) model and adjuvant-induced arthritis (AIA) model to measure the efficacy of therapeutic or prophylactic treatments in reducing the signs of arthritic condition in mice.

For example in CIA mice model, male DBA/J1 mice are shaved at the base of the tail and injected with 0.1 ml emulsion consisting of a 1 to 1 (1 mg/1 mg) mixture of type II chicken collagen with *Mycobacterium butyricum* (Difco lot #147539, Voigt Global Distribution, Lawrence, Kans.) as an adjuvant. Three weeks later, the mice will be boosted with another 0.1 ml injection of emulsion at the base of the tail to induce disease. Three days following this injection, the animals will be randomized and administrated the compounds though variety route, such as IV and Alzet osmotic minipumps (28-day pumps, model 2004, Durect Corporation, Cupertino, Calif.) were implanted subcutaneously on the back of each mouse [Milici A J et al, *Arthritis Research & Therapy* 2008, 10:R14 (doi:10.1186/ar2365), available online at http://arthritis-research.com/content/10/1/R14]. The mice were scored in a blinded manner (0-12) twice weekly for 3 weeks for signs of arthritis in each paw according to the following scale: 0=no swelling or redness/normal paw; 1=swelling and/or redness in one digit; 2=swelling and/or redness in two or more digits; and 3=entire paw is swollen or red. The mice can also be scored in a blinded manner on a 0-20 scale twice weekly for 3 weeks for signs of arthritis in each paw (n=10 for all groups except naïve where n=5). Clinical signs are evaluated using the following scale: 0=normal; 1=one joint affected or mild diffuse erythema and swelling; 2=two joints affected or mild diffuse erythema and swelling; 3=three joints affected or mild diffuse erythema and swelling; 4=four joint affected or marked diffuse erythema and swelling; and 5=severe erythema and severe swelling. Upon study completion (day 28), mice were killed with $CO_2$. Blood samples were immediately taken via cardiac puncture and serum analyzed for compounds levels. The paws and/or knees were removed and processed for histological analyses.

For AA rat model, male Lewis rats are shaved at the base of the tail and injected once intradermally with 100 μl of a 10 mg/ml *Mycobacterium butyricum* (Difco lot #147539) mineral oil suspension. Ten days after this injection, the foot volumes of both the right and left paws are measured with a Stoelting plethysmometer and the rats are administrated the compounds though variety route, such as IV and Alzet osmotic minipumps (14-day pumps, model 2M L2, Stoeling Company, Wood Dale, Ill.) were implanted subcutaneously on the back of each rat (Milici A J et al, *Arthritis Research & Therapy* 2008, 10:$R^{14}$ (doi:10.1186/ar2365)). Swelling in the paws of the rats was measured in a blinded manner with a plethysmometer twice weekly for 2 weeks. At the completion of the study (day 24), rats were killed with anesthesia. Blood samples were immediately taken via cardiac puncture and serum analyzed for compounds levels. Following this, the hind paws were removed and processed for histological analyses.

Various modifications of the invention, in addition to those described herein, will be apparent to those skilled in the art from the foregoing description. Such modifications are also intended to fall within the scope of the appended claims. Each reference cited in the present application is herein incorporated by reference in its entirety.

What is claimed is:
1. A method of inhibiting an activity of JAK3 in a patient in need thereof, the method comprising contacting said JAK3 with a compound of Formula I:

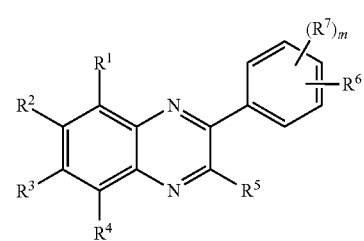

or pharmaceutically acceptable salt thereof, wherein:
$R^1$, $R^2$, $R^3$, and $R^4$ are each, independently, selected from H, halo, $C_{1-6}$ alkyl, $C_{1-6}$ haloalkyl, CN, $NO_2$, OH, $C_{1-6}$ alkoxy, $C_{1-6}$ haloalkoxy, amino, $C_{1-6}$ alkylamino, and $C_{2-8}$ dialkylamino, wherein each of the $C_{1-6}$ alkyl, $C_{1-6}$ haloalkyl, is optionally substituted by 1, 2, 3, 4, or 5 substituents independently selected from halo, CN, $NO_2$, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, $OR^a$, $OC(O)R^b$, $OC(O)NR^cR^d$, $C(O)R^b$, $C(O)NR^cR^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$;

R$^5$ is selected from H, halo, CN, NO$_2$, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, CN, NO$_2$, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$;

—NR$^8$—C(O)—C$_2$-C$_6$ alkenyl;

each R$^7$ is independently selected from halo, CN, NO$_2$, —NR$^8$—W$^1$—(CR$^9$R$^{10}$)$_n$R$^{11}$, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, CN, NO$_2$, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, N$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$;

each R$^8$ is independently selected from H, C$_{1-4}$ alkyl, and C$_{1-4}$ haloalkyl; C$_{2-6}$ alkenyl, C$_{2-6}$ alkynyl, aryl, cycloalkyl, heteroaryl, heterocycloalkyl, arylalkyl, heteroarylalkyl, cycloalkylalkyl, heterocycloalkylalkyl, wherein each of the C$_{1-4}$ alkyl, C$_{1-4}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, CN, NO$_2$, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$;

R$^9$ and R$^{10}$ are each, independently, selected from H, C$_{1-4}$ alkyl, and C$_{1-4}$ haloalkyl;

each R$^{11}$ is independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, heterocycloalkylalkyl, halo, CN, NO$_2$, OR$^{a11}$, NR$^{c11}$R$^{d11}$, NR$^{c11}$C(O)R$^{d11}$, NR$^{c11}$C(O)OR$^{a11}$, NR$^{c11}$C(O)NR$^{c11}$R$^{d11}$, NR$^{c11}$S(O)R$^{b11}$, NR$^{c11}$S(O)$_2$R$^{b11}$, NR$^{c11}$S(O)NR$^{c11}$R$^{d11}$, and NR$^{c11}$S(O)$_2$NR$^{c11}$R$^{d11}$, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, CN, NO$_2$, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SC(O)R$^b$, —S(O)—C$_{1-6}$ alkyl, —S—C$_{1-6}$ alkyl, and —O—S(O)$_2$—C$_{1-6}$ alkyl;

R$^{12}$ and R$^{13}$ are each, independently, selected from H, C$_{1-4}$ alkyl, and C$_{1-4}$ haloalkyl;

R$^{14}$ and R$^{15}$ are each, independently, selected from H, C$_{1-4}$ alkyl, and C$_{1-4}$ haloalkyl;

each W$^1$ is independently selected from —C(R$^{12}$)(R$^{13}$)—, —C(R$^{12}$)=C(R$^{16}$)—, —C(O)—, —S(O)—, —S(O)$_2$—, and —C(S)—;

R$^{16}$ is selected from H, C$_{1-4}$ alkyl, and C$_{1-4}$ haloalkyl;

or R$^{16}$ and —(CR$^9$R$^{10}$)$_n$R$^{11}$ together with the C atom to which they are attached form a 4-, 5-, 6- or 7-membered cycloalkyl or heterocycloalkyl group, each optionally substituted with 1, 2, 3, 4, or 5 substituents each independently selected from OH, C$_{1-6}$ alkoxy, oxo, C$_{1-6}$ haloalkoxy, amino, C$_{1-6}$ alkylamino, C$_{2-8}$ dialkylamino, halo, C$_{1-6}$ alkyl, C$_{1-6}$ haloalkyl, aryl, arylalkyl, heteroaryl, heteroarylalkyl, cycloalkyl or heterocycloalkyl;

each R$^{a11}$ is independently selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl and heterocycloalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, and heterocycloalkyl is optionally substituted with 1, 2, 3, 4, or 5 substituents each independently selected from OH, CN, amino, halo, C$_{1-6}$ alkyl, C$_{1-6}$ haloalkyl, C$_{1-6}$ alkoxy, C$_{1-6}$ haloalkyl, aryl, arylalkyl, heteroaryl, heteroarylalkyl, cycloalkyl and heterocycloalkyl;

each R$^{b11}$ is independently selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, and heterocycloalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl and heterocycloalkyl is optionally substituted with 1, 2, 3, 4, or 5 substituents each independently selected from OH, CN, amino, halo, C$_{1-6}$ alkyl, C$_{1-6}$ haloalkyl, C$_{1-6}$ alkoxy, C$_{1-6}$ haloalkyl, aryl, arylalkyl, heteroaryl, heteroarylalkyl, cycloalkyl and heterocycloalkyl;

R$^{c11}$ and R$^{d11}$ are independently selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, and heterocycloalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, and heterocycloalkyl is optionally substituted with 1, 2, 3, 4, or 5 substituents independently selected from halo, CN, NO$_2$, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, —Y$^1$—Z$^1$, OR$^a$, OC(O)R$^b$, OC(O)NR$^c$R$^d$, C(O)R$^b$, C(O)NR$^c$R$^d$, C(O)OR$^a$, NR$^c$R$^d$, NR$^c$C(O)R$^d$, NR$^c$C(O)OR$^a$, NR$^c$C(O)NR$^c$R$^d$, NR$^c$S(O)$_2$R$^b$, NR$^c$S(O)$_2$NR$^c$R$^d$, SR$^a$, S(O)$_2$R$^b$, and S(O)$_2$NR$^c$R$^d$;

or $R^{c11}$ and $R^{d11}$ together with the N atom to which they are attached form a 4-, 5-, 6- or 7-membered heterocycloalkyl group or heteroaryl group, each optionally substituted with 1, 2, 3, 4, or 5 substituents each independently selected from halo, CN, $NO_2$, $C_{1-6}$ alkyl, $C_{2-6}$ alkenyl, $C_{2-6}$ alkynyl, $C_{1-6}$ haloalkyl, —$Y^1$—$Z^1$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$;

each $Y^1$ is independently selected from absent, $C_{1-6}$ alkylenyl, $C_{2-6}$ alkenylenyl, $C_{2-6}$ alkynylenyl, —$(CR^{14}R^{15})_{p1}$—O—$(CR^{14}R^{15})_{p2}$—, —$(CR^{14}R^{15})_{p1}$—S—$(CR^{14}R^{15})_{p2}$—, —$(CR^{14}R^{15})_{p1}$—$NR^e$—$(CR^{14}R^{15})_{p2}$—, —$(CR^{14}R^{15})_{p1}$—C(O)—$(CR^{14}R^{15})_{p2}$—, —$(CR^{14}R^{15})_{p1}$—C(O)O—$(CR^{14}R^{15})_{p2}$—, —$(CR^{14}R^{15})_{p1}$—C(O)$NR^e$—$(CR^{14}R^{15})_{p2}$—, —$(CR^{14}R^{15})_{p1}$, —$S(O)_2$—$(CR^{14}R^{15})_{p2}$—, —$(CR^{14}R^{15})_{p1}$—$S(O)NR^e$—$(CR^{14}R^{15})_{p2}$—, —$(CR^{14}R^{15})_{p1}$—$S(O)_2NR^e$—$(CR^{14}R^{15})_{p2}$—, and —$(CR^{14}R^{15})_{p1}$—$NR^eC(O)NR^f$—$(CR^{14}R^{15})_{p2}$—, wherein each of the $C_{1-6}$ alkylenyl, $C_{2-6}$ alkenylenyl and $C_{2-6}$ alkynylenyl is optionally substituted by 1, 2, or 3 substituents independently selected from halo, OH, CN, amino, $C_{1-6}$ alkylamino, $C_{2-8}$ dialkylamino, $C_{1-6}$ alkyl, $C_{1-6}$ haloalkyl, $C_{1-6}$ alkoxy, $C_{1-6}$ haloalkyl, aryl, arylalkyl, heteroaryl, heteroarylalkyl, cycloalkyl and heterocycloalkyl;

each $Z^1$ is independently selected from $C_{1-6}$ alkyl, $C_{1-6}$ haloalkyl, $C_{2-6}$ alkenyl, $C_{2-6}$ alkynyl, arylalkyl, cycloalkylalkyl, heteroarylalkyl, heterocycloalkylalkyl, aryl, cycloalkyl, heteroaryl, and heterocycloalkyl, each optionally substituted by 1, 2, 3, 4, or 5 substituents independently selected from $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, halo, CN, $NO_2$, $OR^a$, $OC(O)R^b$, $OC(O)NR^cR^d$, $C(O)R^b$, $C(O)NR^cR^d$, $C(O)OR^a$, $NR^cR^d$, $NR^cC(O)R^d$, $NR^cC(O)OR^a$, $NR^cC(O)NR^cR^d$, $NR^cS(O)_2R^b$, $NR^cS(O)_2NR^cR^d$, $SR^a$, $S(O)_2R^b$, and $S(O)_2NR^cR^d$;

each $R^a$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents each independently selected from OH, CN, amino, $C_{1-6}$ alkylamino, $C_{2-8}$ dialkylamino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

each $R^b$ is independently selected from H, $NH_2$, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents each independently selected from OH, $C_{1-6}$ alkoxy, $C_{1-6}$ haloalkoxy, amino, $C_{1-6}$ alkylamino, $C_{2-8}$ dialkylamino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^c$ and $R^d$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents each independently selected from OH, $C_{1-6}$ alkoxy, $C_{1-6}$ haloalkoxy, amino, $C_{1-6}$ alkylamino, $C_{2-8}$ dialkylamino, halo, $C_{1-6}$ alkyl, $C_{1-6}$ haloalkyl, aryl, arylalkyl, heteroaryl, heteroarylalkyl, cycloalkyl and heterocycloalkyl;

or $R^c$ and $R^d$ together with the N atom to which they are attached form a 4-, 5-, 6- or 7-membered heterocycloalkyl group that is optionally substituted with 1, 2, 3, 4, or 5 substituents each independently selected from OH, $C_{1-6}$ alkoxy, $C_{1-6}$ haloalkoxy, amino, $C_{1-6}$ alkylamino, $C_{2-8}$ dialkylamino, halo, $C_{1-6}$ alkyl, $C_{1-6}$ haloalkyl, aryl, arylalkyl, heteroaryl, heteroarylalkyl, cycloalkyl or heterocycloalkyl;

$R^e$ and $R^f$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, and heterocycloalkyl is optionally substituted with 1, 2, 3, 4, or 5 substituents each independently selected from OH, $C_{1-6}$ alkoxy, $C_{1-6}$ haloalkoxy, amino, $C_{1-6}$ alkylamino, $C_{2-8}$ dialkylamino, halo, $C_{1-6}$ alkyl, $C_{1-6}$ haloalkyl, aryl, arylalkyl, heteroaryl, heteroarylalkyl, cycloalkyl, and heterocycloalkyl;

m is 0, 1, 2, 3, or 4;

each n is independently 0, 1, 2, 3, or 4;

each p1 is independently 0, 1, 2, or 3; and each p2 is independently 0, 1, 2, or 3.

2. The method of claim 1 wherein $R^1$, $R^2$, $R^3$, and $R^4$ are each, independently, selected from H, halo, $C_{1-6}$ alkyl, and $C_{1-6}$ haloalkyl.

3. The method of claim 1 wherein $R^5$ is selected from H, halo, $C_{1-6}$ alkyl, $C_{1-6}$ haloalkyl, CN, $NO_2$, $C_{1-6}$ alkoxy, and $C_{1-6}$ haloalkoxy.

4. The method of claim 1 wherein $R^5$ is selected from H, halo, $C_{1-6}$ alkyl, and $C_{1-6}$ haloalkyl.

5. The method of claim 1 wherein each $W^1$ is —C(O)—.

6. The method of claim 1 wherein each $R^7$ is independently selected from halo, $C_{1-6}$ alkyl, $C_{1-6}$ haloalkyl, CN, $NO_2$, —$NR^8$—C(O)—$(CR^9R^{10})_n R^{11}$, OH, $C_{1-6}$ alkoxy, $C_{1-6}$ haloalkoxy, amino, $C_{1-6}$ alkylamino, and $C_{2-8}$ dialkylamino.

7. The method of claim 1 wherein each $R^8$ is H or methyl.

8. The method of claim 1 wherein each $R^8$ is H.

9. The method of claim 1 wherein the compound of Formula I is a compound of Formula II:

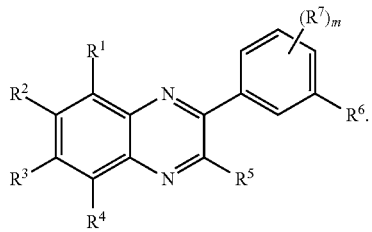

10. The method of claim 1 wherein the compound of Formula I is:

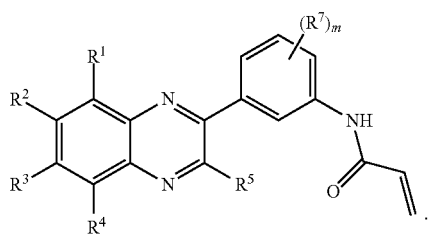

11. The method of claim 1 wherein n is 0.
12. The method of claim 1 wherein n is 1.
13. The method of claim 1 wherein each $R^{11}$ is independently selected from $C_{1-6}$ alkyl, $C_{1-6}$ haloalkyl, aryl, cycloalkyl, heteroaryl, heterocycloalkyl, halo, CN, $OR^{a11}$, and $NR^{c11}R^{d11}$, wherein each of the $C_{1-6}$ alkyl, $C_{1-6}$ haloalkyl, aryl, cycloalkyl, heteroaryl, and heterocycloalkyl is optionally substituted by 1, 2, 3, 4, or 5 substituents independently selected from halo, CN, $NO_2$, $C_{1-6}$ alkyl, $C_{1-6}$ haloalkyl, OH, $C_{1-6}$ alkoxy, and $C_{1-6}$ haloalkoxy.

14. The method of claim 1, wherein the compound of Formula I or pharmaceutically acceptable salt thereof is N-(3-(quinoxalin-2-yl)phenyl)acrylamide.

15. A method of inhibiting an activity of JAK3 comprising contacting said JAK3 with

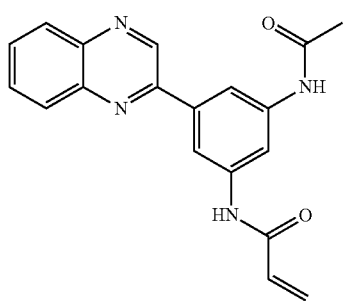 [SMILES: C=CC(=O)Nc1cc(NC(C)=O)cc(-c2cnc3ccccc3n2)c1]

N-(3-acetamido-5-(quinoxalin-2-yl)phenyl)acrylamide, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,592,415 B2 | Page 1 of 1 |
| APPLICATION NO. | : 12/704404 | |
| DATED | : November 26, 2013 | |
| INVENTOR(S) | : Haiching Ma et al. | |

It is certified that error appears in the above-identified patent and that said Letters Patent is hereby corrected as shown below:

On the title page, inventorship item (75) should read as follows:

(75) Inventors: Haiching Ma, Malvern, PA (US); Sorin Vasile Filip, Wadebridge (GB); Matthew Alexander Henry Stent, Camelford (GB); James Alexander Dolan, Truro (GB); Bartosz Dietrich, Plymouth (GB)

Signed and Sealed this
Twenty-fifth Day of March, 2014

Michelle K. Lee
*Deputy Director of the United States Patent and Trademark Office*